US009895077B2

(12) United States Patent
Shahaf et al.

(10) Patent No.: US 9,895,077 B2
(45) Date of Patent: Feb. 20, 2018

(54) METHOD FOR DIAGNOSING A BRAIN RELATED DISORDER USING BRAIN NETWORK ACTIVITY PATTERNS

(75) Inventors: Goded Shahaf, Haifa (IL); Amit Reches, Haifa (IL); Amir B. Geva, Tel-Aviv (IL); Noga Pinchuk, Zikhron-Yaakov (IL); Guy Ben-Bassat, Kibbutz Beit Zera (IL); Ayelet Kanter, Yokneam Ilit (IL); Revital Shani-Hershkovich, Mazkeret Batia (IL); Ronen Gadot, Tzur-Yigal (IL); Yaki Stern, Moshav Sde Yaakov (IL)

(73) Assignee: Elminda Ltd., Herzliya (IL)

( * ) Notice: Subject to any disclaimer, the term of this patent is extended or adjusted under 35 U.S.C. 154(b) by 0 days.

(21) Appl. No.: 13/522,747

(22) PCT Filed: Jan. 18, 2011

(86) PCT No.: PCT/IL2011/000055

§ 371 (c)(1),
(2), (4) Date: Jul. 18, 2012

(87) PCT Pub. No.: WO2011/086563

PCT Pub. Date: Jul. 21, 2011

(65) Prior Publication Data

US 2012/0296569 A1 Nov. 22, 2012

Related U.S. Application Data

(60) Provisional application No. 61/295,797, filed on Jan. 18, 2010, provisional application No. 61/300,886, filed on Feb. 3, 2010.

(51) Int. Cl.

| | |
|---|---|
| ***G01N 33/48*** | (2006.01) |
| ***A61B 5/048*** | (2006.01) |
| ***A61B 5/0484*** | (2006.01) |
| ***A61B 5/00*** | (2006.01) |
| ***G06F 19/00*** | (2018.01) |

(52) U.S. Cl.
CPC ............ *A61B 5/048* (2013.01); *A61B 5/0484* (2013.01); *A61B 5/4064* (2013.01); *G06F 19/3431* (2013.01); *G06F 19/3443* (2013.01)

(58) Field of Classification Search
None
See application file for complete search history.

(56) References Cited

U.S. PATENT DOCUMENTS

| | | | | |
|---|---|---|---|---|
| 6,792,304 | B1 | 9/2004 | Silberstein | |
| 7,720,530 | B2 | 5/2010 | Causevic | |
| 8,320,649 | B2 * | 11/2012 | Shahaf et al. | 382/128 |
| 2004/0059241 | A1 | 3/2004 | Suffin | |
| 2004/0152995 | A1 | 8/2004 | Cox et al. | |
| 2005/0165327 | A1 | 7/2005 | Thibault et al. | |
| 2005/0177058 | A1 | 8/2005 | Sobell | |
| 2006/0004422 | A1 | 1/2006 | De Ridder | |
| 2008/0103547 | A1 | 5/2008 | Okun et al. | |
| 2008/0208073 | A1 | 8/2008 | Causevic | |
| 2009/0297000 | A1 | 12/2009 | Shahaf et al. | |
| 2010/0022907 | A1 | 1/2010 | Perez-Velazquez | |
| 2010/0191139 | A1 | 7/2010 | Jacquin et al. | |
| 2011/0060266 | A1 | 3/2011 | Streeter et al. | |
| 2014/0163328 | A1 | 6/2014 | Geva et al. | |

FOREIGN PATENT DOCUMENTS

| | | |
|---|---|---|
| CN | 101155548 | 4/2008 |
| CN | 102014742 | 4/2011 |
| CN | 102906752 | 1/2013 |
| JP | 07-040445 | 2/1995 |
| JP | 2002-507940 | 3/2002 |
| JP | 2004-530475 | 10/2004 |
| JP | 2008-098280 | 4/2008 |
| JP | 2009-528103 | 8/2009 |
| JP | 2009-542351 | 12/2009 |
| WO | WO 98/56566 | 12/1998 |
| WO | WO 00/47278 | 8/2000 |
| WO | WO 02/091119 | 11/2002 |
| WO | WO 2005/079332 | 9/2005 |
| WO | WO 2006/094797 | 9/2006 |
| WO | WO 2007/098957 | 9/2007 |
| WO | WO 2007/138579 | 12/2007 |
| WO | WO 2008/005513 | 1/2008 |
| WO | WO 2009/069134 | 6/2009 |
| WO | WO 2009/069135 | 6/2009 |
| WO | WO 2009/069136 | 6/2009 |
| WO | WO 2009/129279 | 10/2009 |
| WO | WO 2011/086563 | 7/2011 |
| WO | WO 2013/011515 | 1/2013 |

OTHER PUBLICATIONS

Stam et al. (Nonlinear Biomedical Physics 2007, 1:3, pp. 1-19).*
International Preliminary Report on Patentability dated Aug. 2, 2012 From the International Bureau of WIPO Re. Application No. PCT/IL2011/000055.
International Search Report and the Written Opinion dated Nov. 7, 2012 From the International Searching Authority Re. Application No. PCT/IL2012/050262.
International Search Report and the Written Opinion dated Feb. 7, 2012 From the International Searching Authority Re. Application No. PCT/IL2011/000055.
Doyle et al. "Attention-Deficit/Hyperactivity Disorder Endophenotypes", Biological Psychiatry, XP004932899, 57(11): 1324-1335, Jun. 1, 2005. Section 'Electrophysiology: Association With ADHD', p. 1330.
Reijneveld et al. "The Application of Graph Theoretical Analysis to Complex Networks in the Brain", Clinical Neurophysiology, XP022295008, 118(11): 2317-2331, Oct. 11, 2007.

(Continued)

*Primary Examiner* — Pablo S Whaley

(57) ABSTRACT

A method of analyzing neurophysiological data is disclosed. The method comprises: identifying activity-related features in the data, constructing a brain network activity (BNA) pattern having a plurality of nodes, each representing a feature of the activity-related features, and assigning a connectivity weight to each pair of nodes in the BNA pattern.

32 Claims, 37 Drawing Sheets
(34 of 37 Drawing Sheet(s) Filed in Color)

(56) References Cited

OTHER PUBLICATIONS

International Preliminary Report on Patentability dated Jan. 30, 2014 From the International Bureau of WIPO Re. Application No. PCT/IL2012/050262.
Lirdprapamongkol et al. "A Flavonoid Chrysin Suppresses Hypoxic Survival and Metastatic Growth of Mouse Breast Cancer Cells", Oncology Reports, 30: 2357-2364, 2013.
Notice of Reasons for Refusal dated Sep. 24, 2014 From the Japanese Patent Office Re. Application No. 2012-548537 and Its Translation Into English.
Notificaiton of Office Action and Search Report dated Dec. 1, 2014 From The State Intellectual Property Office of the People's Republic of China Re. Application No. 201180014613.5.
Notification of Office Action dated Sep. 29, 2015 From The State Intellectual Property Office of the People's Republic of China Re. Application No. 201180014613.5 and Its Translation Into English.
Translation dated Dec. 16, 2014 of Notification of Office Action and Search Report dated Dec. 1, 2014 From The State Intellectual Property Office of the People's Republic of China Re. Application No. 201180014613.5.
Communication Pursuant to Article 94(3) EPC dated May 4, 2015 From the European Patent Office Re. Application No. 12750826.5.
Notification of Office Action and Search Report dated Apr. 9, 2015 From The State Intellectual Property Office of the People's Republic of China Re. Application No. 201280045473.2 and Its Translation Into English.
Office Action dated Apr. 29, 2015 From the Israel Patent Office Re. Application No. 221019.
Translation dated May 18, 2015 of Office Action dated Apr. 29, 2015 From the Israel Patent Office Re. Application No. 221019.
Notice of Reasons for Refusal dated Jun. 19, 2015 From the Japanese Patent Office Re. Application No. 2012-548537 and Its Translation Into English.
Notice of Reason for Rejection dated Apr. 26, 2016 From the Japanese Patent Office Re. Application No. 2014-520791 and Its Translation Into English.
Notification of Office Action and Search Report dated May 5, 2016 From The State Intellectual Property Office of the People's Republic of China Re. Application No. 201180014613.5 and its Translation into English.
Request for Examination dated May 4, 2016 From the ROSPATENT, Federal Government Institution, Federal Institute of Industrial Property of the Federal Service of Intellectual Property, Patent and Trademarks of the Russian Federation Re. Application No. 2014105665 and Its Translation Into English.
Notification of Office Action and Search Report dated Nov. 10, 2015 From The State Intellectual Property Office of the People's Republic of China Re. Application No. 201280045473.2.
Translation dated Nov. 24, 2015 of Notification of Office Action and Search Report dated Nov. 10, 2015 From The State Intellectual Property Office of the People's Republic of China Re. Application No. 201280045473.2.
Notice of Reasons for Rejection dated Dec. 15, 2015 From the Japanese Patent Office Re. Application No. 2012-548537 and Its Translation Into English.
Notification of Office Action and Search Report dated Mar. 3, 2016 From The State Intellectual Property Office of the People's Republic of China Re. Application No. 201280045473.2 and Its Translation Into English.
Patent Examination Report dated Apr. 20, 2016 From the Australian Government, IP Australia Re. Application No. 2012285379.
Communication Pursuant to Article 94(3) EPC dated Mar. 9, 2016 From the European Patent Office Re. Application No. 12750826.5.
Pre-Examination Processing Notice dated Feb. 16, 2016 From the Australian Government, IP Australia Re. Application No. 2012285379.
Restriction Official Action dated Feb. 17, 2016 From the US Patent and Trademark Office Re. U.S. Appl. No. 14/233,788.
Official Action dated May 27, 2016 From the US Patent and Trademark Office Re. U.S. Appl. No. 14/233,788.
Communication Pursuant to Article 94(3) EPC dated Mar. 31, 2017 From the European Patent Office Re. Application No. 11705277.9. (11 Pages).
Office Action dated Apr. 5, 2017 From the Israel Patent Office Re. Application No. 230502 and Its Translation Into English. (7 Pages).
Notice of Reason for Rejection dated Dec. 16, 2016 From the Japanese Patent Office Re. Application No. 2014-520791 and Its Translation Into English. (5 Pages).
Notification of Office Action and Search Report dated Nov. 7, 2016 From The State Intellectual Property Office of the People's Republic of China Re. Application No. 201180014613.5. (5 Pages).
Office Action dated Apr. 29, 2015 From the Israel Patent Office Re. Application No. 221019 and Its Translation Into English. (6 Pages).
Official Action dated Jan. 5, 2017 From the US Patent and Trademark Office Re. U.S. Appl. No. 14/233,788. (36 pages).
Requisition by the Examiner dated Jan. 9, 2017 From the Canadian Intellectual Property Office Re. Application No. 2,786,380. (12 Pages).
Translation of Notification of Office Action and Search Report dated Nov. 7, 2016 From The State Intellectual Property Office of the People's Republic of China Re. Application No. 201180014613.5. (5 Pages).
Notice of Reasons for Refusal dated May 22, 2015 From the Japan Patent Office Re. Application No. 2016-114846 and Its Translation Into English. (7 Pages).
Request for Examination Dated Aug. 24, 2017 From the ROSPATENT, Federal Government Institution, Federal Institute of Industrial Property of the Federal Service of Intellectual Property, Patent and Trademarks of the Russian Federation Re. Application No. 2014105665 and Its Translation Into English. (15 Pages).
Requisition by the Examiner Dated Nov. 20, 2017 From the Innovation, Science and Economic Development Canada, Canadian Intellectual Property Office Re. Application No. 2,786,380. (12 Pages).

* cited by examiner

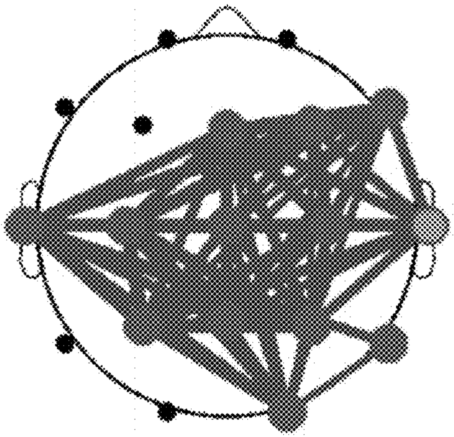
FIG. 14A
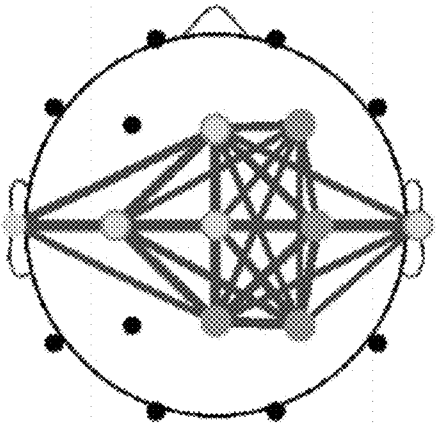
FIG. 14B
*Control* *ADHD*
FIG. 15A
*Group*
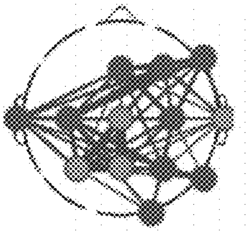
FIG. 15B
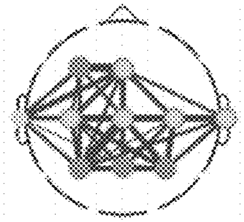
FIG. 15D
*Single Control*
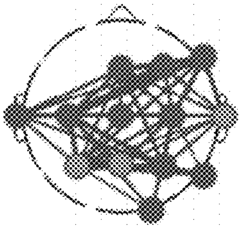
FIG. 15C
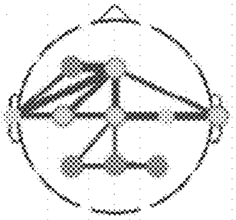
FIG. 15E
*Single ADHD*
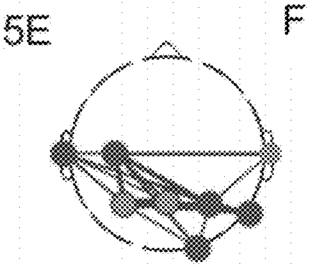
FIG. 15F
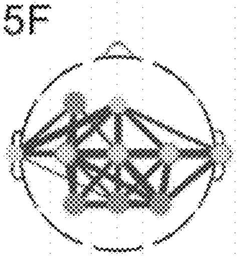

FIG. 17A
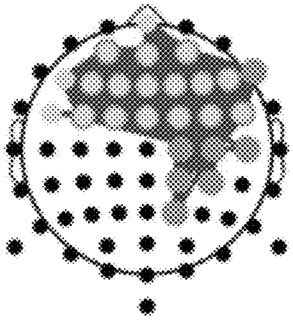
FIG. 17B
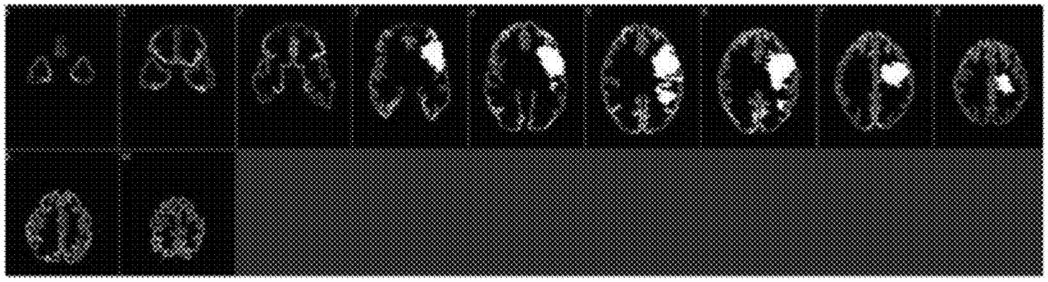
FIG. 18

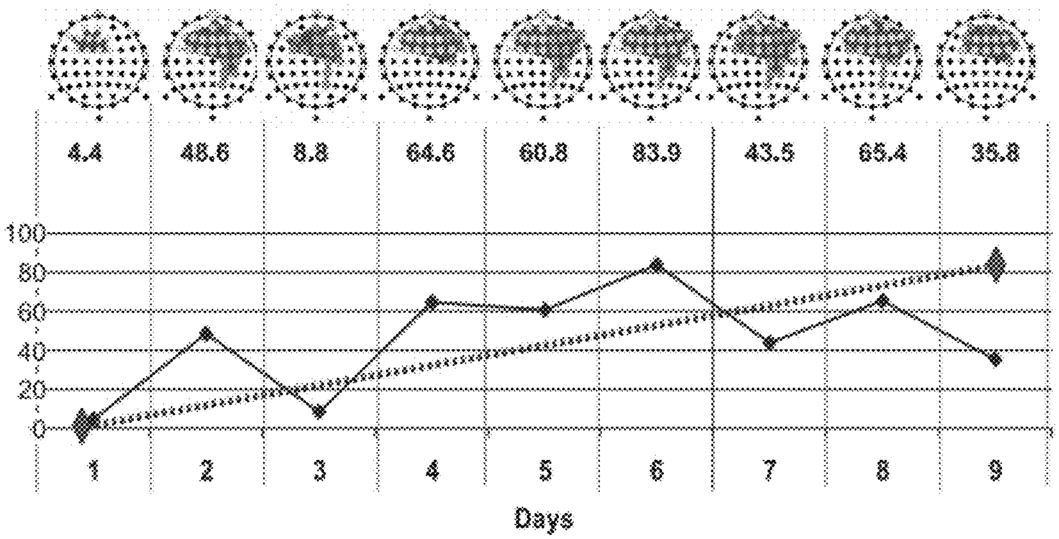
FIG. 19
FIG. 20
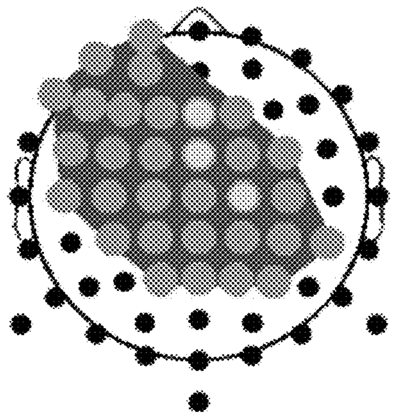

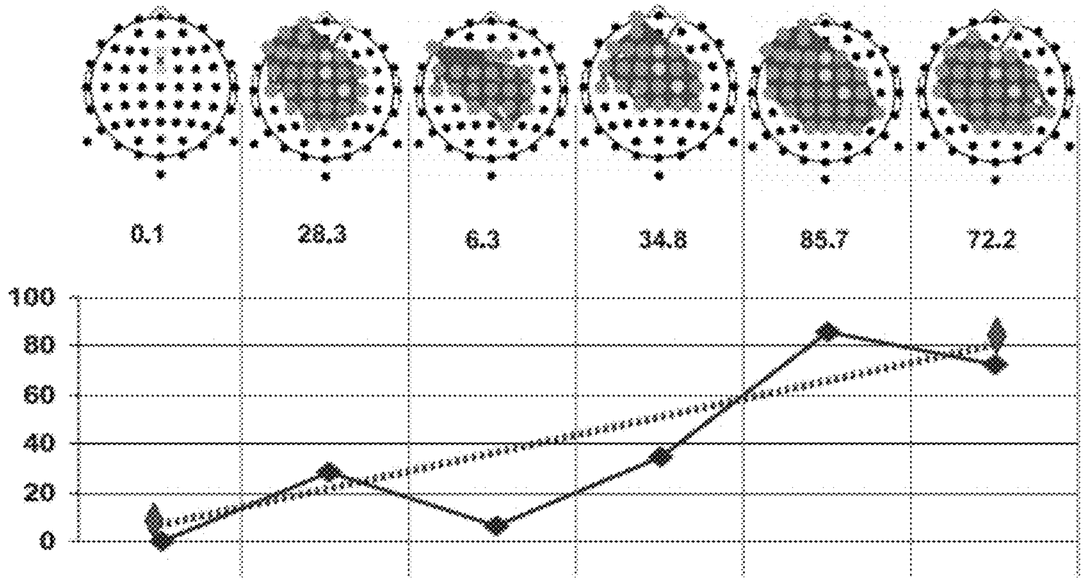
FIG. 21
FIG. 22
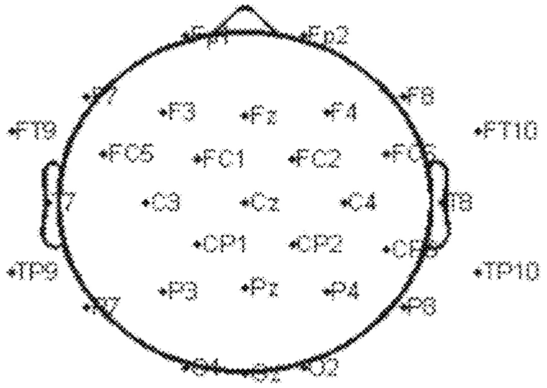

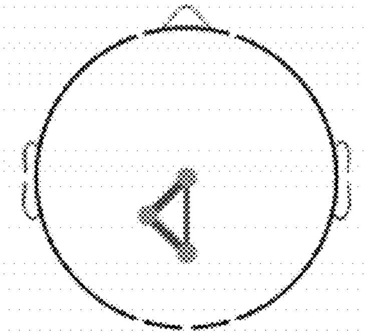
FIG. 23A
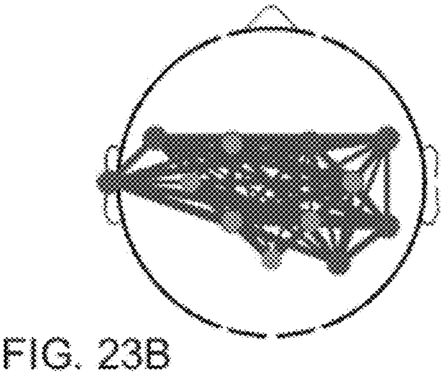
FIG. 23B
FIG. 24A
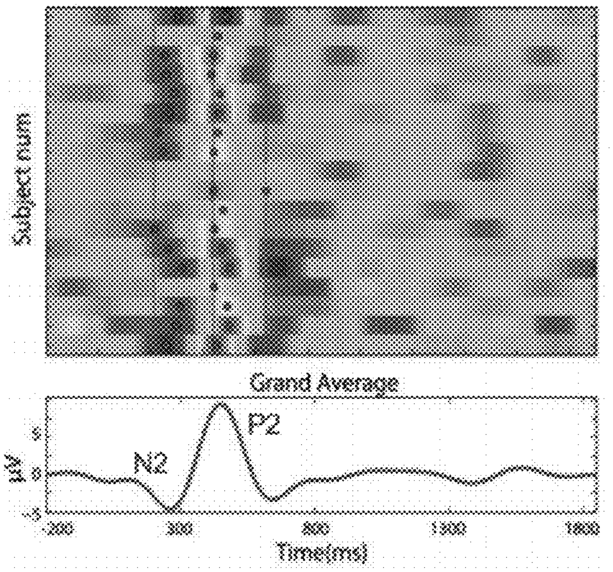
FIG. 24B
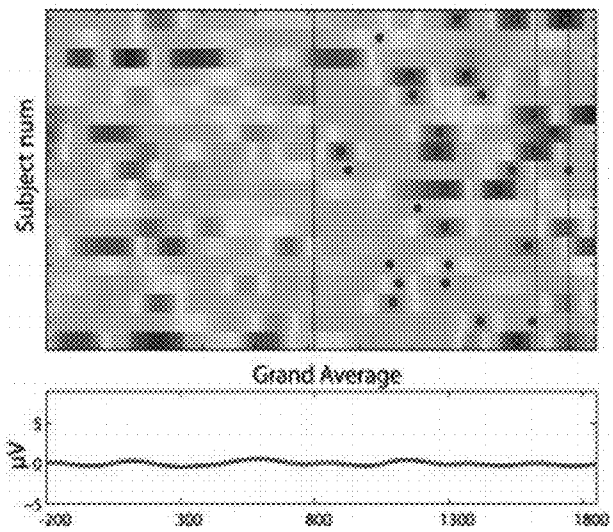

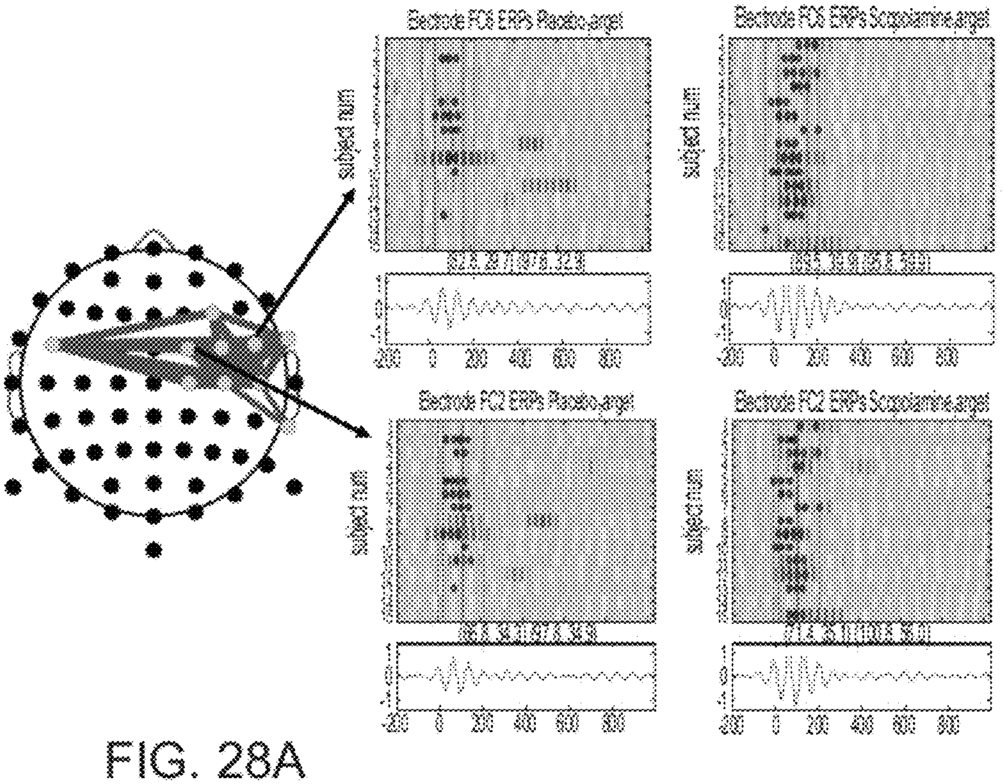
FIG. 28A
FIG. 28B
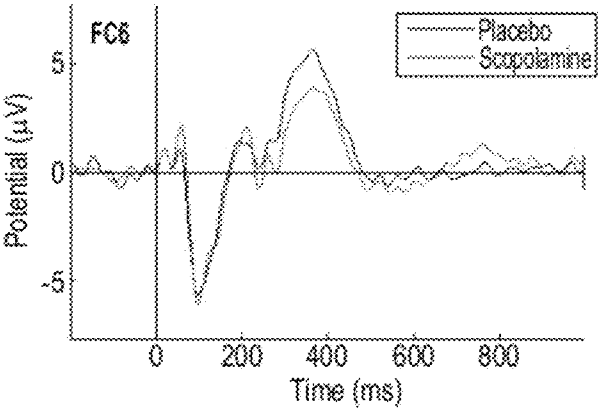
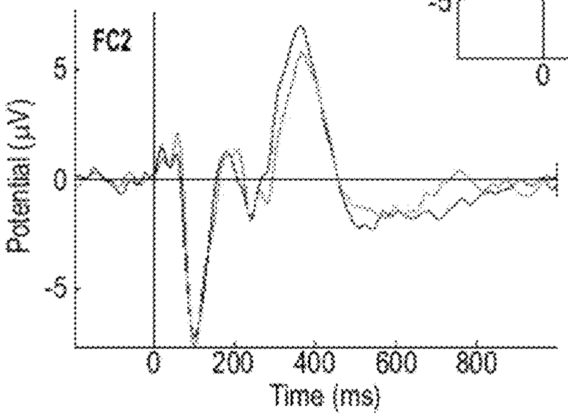
FIG. 28C

FIG. 36A
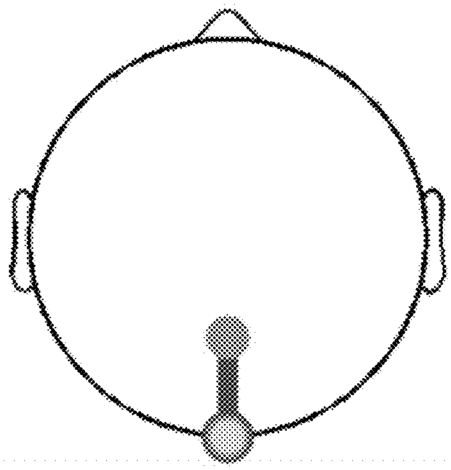
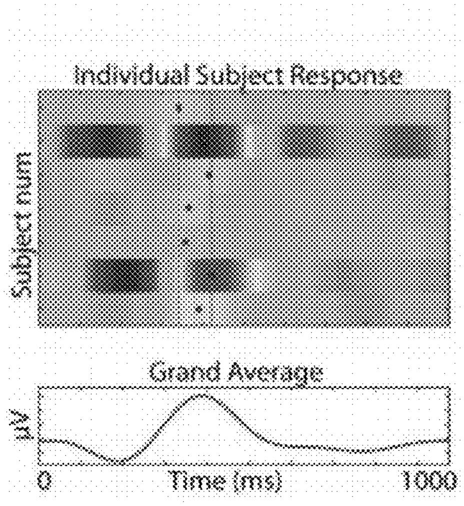
FIG. 36B
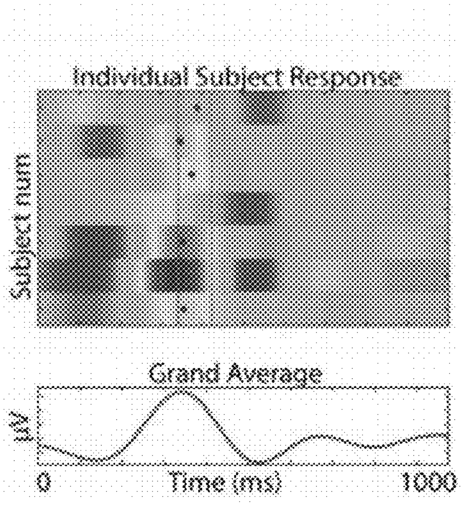
FIG. 36C

FIG. 37A
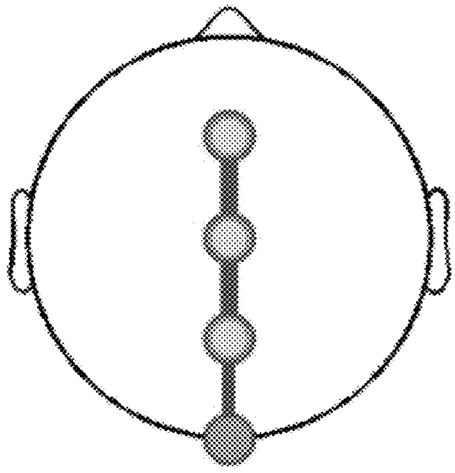
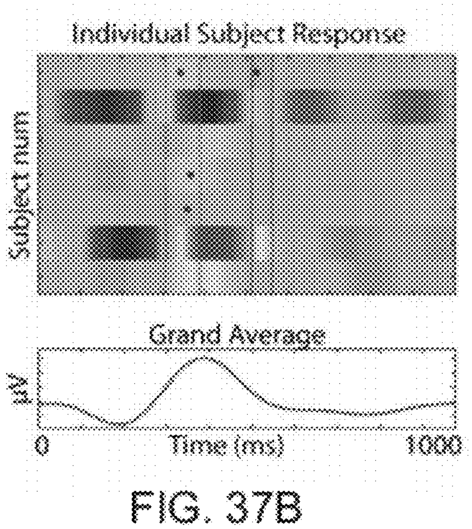
FIG. 37B
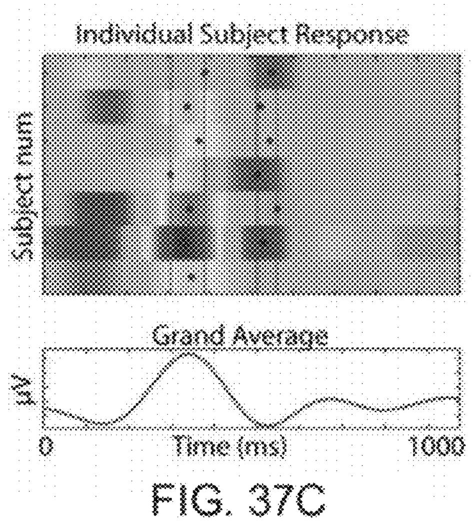
FIG. 37C

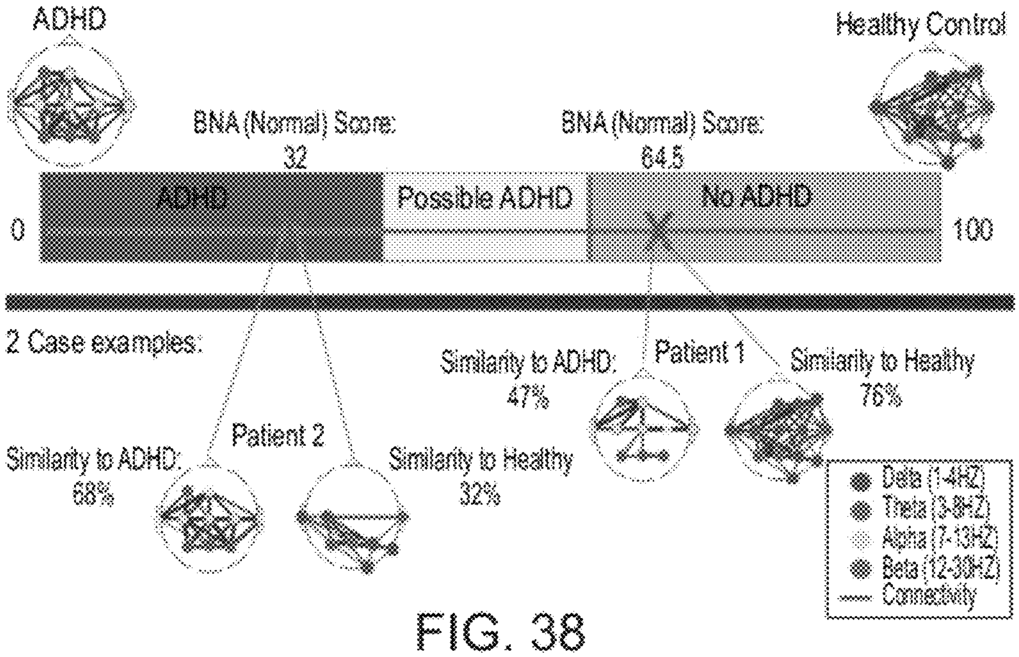
FIG. 38
FIG. 39
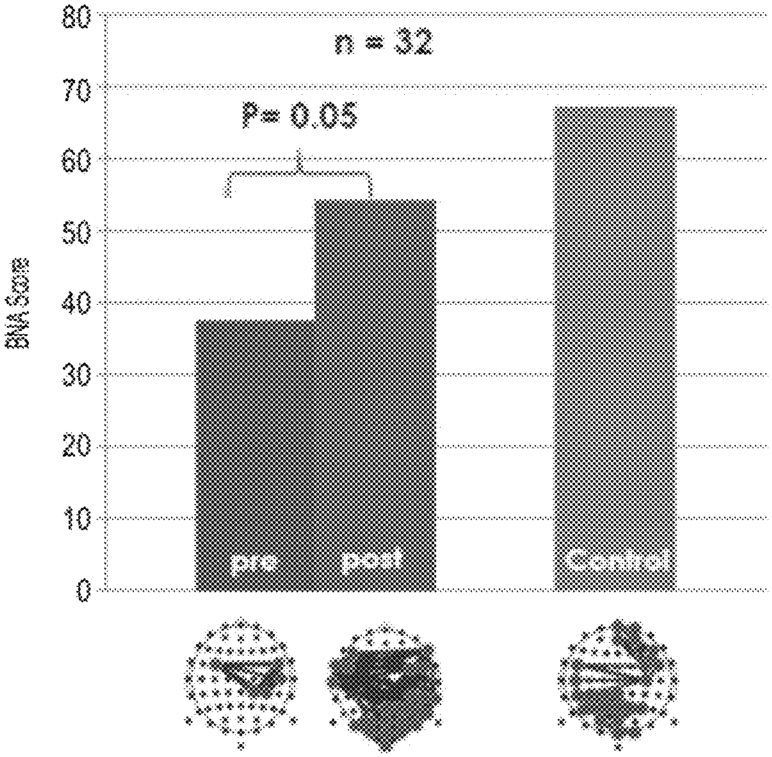

FIG. 41A
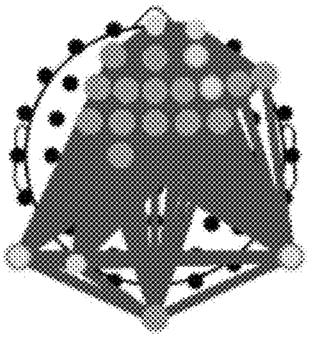
FIG. 41B
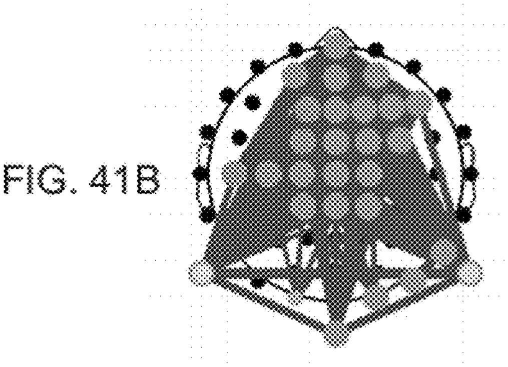
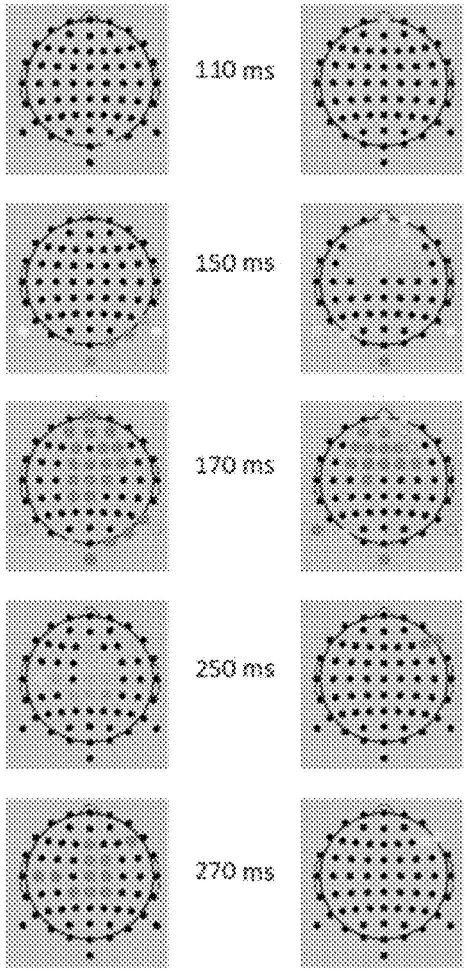
FIG. 41C
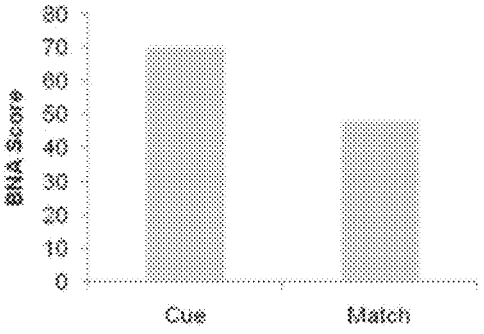
FIG. 41D FIG. 43A
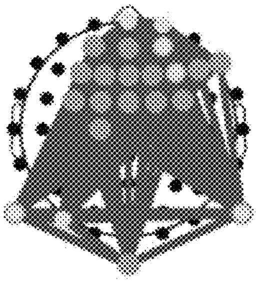
FIG. 43B
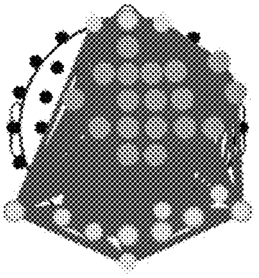
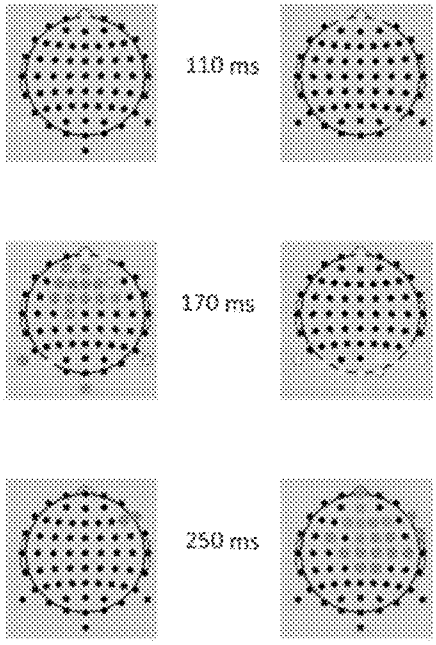
FIG. 43C
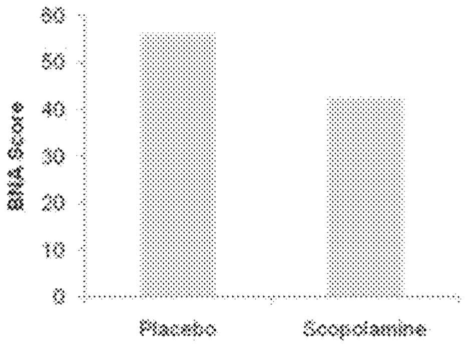
FIG. 43D

METHOD FOR DIAGNOSING A BRAIN RELATED DISORDER USING BRAIN NETWORK ACTIVITY PATTERNS

RELATED APPLICATIONS

This Application is a National Phase of PCT Patent Application No. PCT/IL2011/000055 having International filing date of Jan. 18, 2011, which claims the benefit of priority under 35 USC § 119(e) of U.S. Provisional Patent Application Nos. 61/295,797 filed on Jan. 18, 2010 and U.S. Application No. 61/300,886 filed on Feb. 3, 2010. The contents of the above applications are all incorporated by reference as if fully set forth herein in their entirety.

FIELD AND BACKGROUND OF THE INVENTION

The present invention, in some embodiments thereof, relates to neurophysiology and, more particularly, but not exclusively, to method and system for analyzing data.

Little is known about the mechanisms that allow the brain to selectively improve the neural representations of behaviorally important stimuli while ignoring irrelevant stimuli. The brain is a complex structure of nerve cells that produce signals called action potentials. These action potentials move from one cell to another across a gap called the synapse. These potentials summate in the cortex and extend through the coverings of the brain to the scalp, where they can be measured using appropriate electrodes. Rhythmical measured activity represents postsynaptic cortical neuronal potentials which are synchronized by the complex interaction of large populations of cortical cells.

Behavioral functions are based upon flow among various functional regions in the brain, involving specific spatiotemporal flow patterns. A specific spatiotemporal pattern underlying a certain behavioral function is composed of functional brain regions, which are often active for at least several tens of milliseconds and more. The flow of activity among those regions is often synchronization-based.

Known in the art are methods that identify discrete participating regions for the purpose of relating behavioral functions to their underlying localized brain activities. Other techniques employ analysis of the flow from one region to another.

U.S. Pat. No. 6,792,304 discloses a method and a system for mass communication assessment. A cognitive task is transmitted from a central control site to a plurality of remote test sites via Internet. The brain response of the subjects at the remote sites in response to the task is recorded and transmitted back to the central control site via the Internet. The central control site then computes the variations in the brain activities for the subjects at each of the selected sites.

U.S. Published Application No. 20040059241 discloses a method for classifying and treating physiologic brain imbalances. Neurophysiologic techniques are used for obtaining a set of analytic brain signals from a subject, and a set of digital parameters is determined from the signals. The digital parameters are quantitatively mapped to various therapy responsivity profiles. The signals and parameters for a subject are compared to aggregate neurophysiologic information contained in databases relating to asymptomatic and symptomatic reference populations, and the comparison is used for making treatment recommendations. Treatment response patterns are correlated as a dependent variable to provide a connection to successful outcomes for clinical treatment of afflicted subjects.

International Publication No. WO 2007/138579, the contents of which are hereby incorporated by reference, describes a method for establishing a knowledge base of neuropsychological flow patterns. Signals from multiple research groups for a particular behavioral process are obtained, and sources of activity participating in the particular behavioral functions are localized. Thereafter, sets of patterns of brain activity are identified, and neuropsychological analysis is employed for analyzing the localized sources and the identified patterns. The analysis includes identification and ranking of possible pathways. A set of flow patterns is then created and used as a knowledge base. The knowledge base is then used as a constraint for reducing the number of ranked pathways.

International Publication Nos. WO 2009/069134, WO 2009/069135 and WO 2009/069136, the contents of which are hereby incorporated by reference, describe a technique in which neurophysiological data are collected before and after the subject has performed a task and/or action that forms a stimulus. The stimulus is used for defining features in the data, and the data are decomposed according to the defined features. Thereafter, the features are analyzed to determine one or more patterns in the data. The decomposition can employ clustering for locating one or more important features in the data, wherein a collection of clusters forms an activity network. The data patterns can be analyzed for defining a neural model which can be used for simulating the effect of a particular pathology and/or treatment on the brain.

Additional background art includes U.S. Published Application No. 20050177058, which discloses a system in which EEG readings from more than one subject at the same or different locations are collected, analyzed and compared, when they are exposed to a common set of stimuli. The compatibility of the subjects is studied using their EEG readings, and concealed information is discovered or verified from.

SUMMARY OF THE INVENTION

According to an aspect of some embodiments of the present invention there is provided a method of analyzing neurophysiological data. The method comprises: identifying activity-related features in the data, constructing a brain network activity (BNA) pattern having a plurality of nodes, each representing a feature of the activity-related features, and assigning a connectivity weight to each pair of nodes in the BNA pattern.

According to some embodiments of the invention the nodes represent clusters of vectors of data characteristics.

According to some embodiments of the invention for each cluster, each vector of data characteristics corresponds to data obtained from a different subject.

According to some embodiments of the invention for each cluster, all vectors of data characteristics correspond to data obtained from the same subject but in response to a separate stimulus.

According to some embodiments of the invention the connectivity weight comprises a weight index calculated based on at least one cluster property selected from the group consisting of: (i) a number of vectors in a corresponding pair of clusters; (ii) a variability among numbers of vectors in the corresponding pair of clusters; (iii) a width of time windows associated with each cluster of the corresponding pair of clusters; (iv) a latency difference separating the corresponding pair of clusters; (v) amplitude of a signal associated with the corresponding pair of clusters; (vi) frequency of a signal associated with the corresponding pair of clusters; and (vii) the width of a spatial window defining the clusters.

According to an aspect of some embodiments of the present invention there is provided a method of analyzing neurophysiological data of a subject. The method comprises: identifying features and relations among features in the data; comparing the features and the relations among features to features and relations among features of reference neurophysiological data so as to identify activity-related features in the data of the subject; constructing a brain network activity (BNA) pattern having a plurality of nodes, each representing a feature of the activity-related features; and assigning a connectivity weight to each pair of nodes in the BNA pattern.

According to some embodiments of the invention the reference neurophysiological data corresponds to data acquired from a group or a sub-group of subjects.

According to some embodiments of the invention the reference neurophysiological data corresponds to history data previously acquired from the same subject.

According to some embodiments of the invention the features and relations among features of the reference data are provided as at least one previously annotated BNA pattern.

According to some embodiments of the invention the at least one previously annotated BNA pattern is at least one entry in a database of previously annotated BNA patterns, and the method further comprises constructing a BNA pattern in relation to each entry of the database.

According to some embodiments of the invention the method further comprises extracting prognostic information regarding a brain condition, responsively to the comparison.

According to some embodiments of the invention the at least one previously annotated BNA pattern comprises at least one BNA pattern annotated as normal, and at least one BNA pattern annotated as abnormal.

According to some embodiments of the invention the method comprises acquiring the neurophysiological data from the brain of the subject, before, during and/or after the subject is performing or conceptualizing performing a task.

According to some embodiments of the invention the method comprises presenting to the subject a feedback regarding similarity between the BNA pattern of the subject and the previously annotated BNA patterns.

According to some embodiments of the invention the method comprises stimulating the brain so as to enhance similarity between the BNA pattern of the subject and the BNA pattern annotated as normal.

According to some embodiments of the invention the at least one BNA pattern annotated as abnormal comprises at least one BNA pattern annotated as corresponding to an attention deficit hyperactivity disorder (ADHD).

According to some embodiments of the invention the at least one BNA pattern annotated as abnormal comprises at least one BNA pattern annotated as corresponding to Alzheimer's disease (AD).

According to some embodiments of the invention the at least one BNA pattern annotated as abnormal comprises at least one BNA pattern annotated as corresponding to mild cognitive impairment (MCI).

According to some embodiments of the invention the at least one BNA pattern annotated as abnormal comprises at least one BNA pattern annotated as corresponding to memory deficiency.

According to some embodiments of the invention the at least one BNA pattern annotated as abnormal comprises at least one BNA pattern annotated as corresponding to pain.

According to some embodiments of the invention the at least one previously annotated BNA pattern comprises a set of annotated BNA pattern.

According to some embodiments of the invention the at least one previously annotated BNA pattern is a baseline annotated BNA pattern characterizing a group of subjects identified as having the same brain disorder.

According to some embodiments of the invention the at least one previously annotated BNA pattern is a baseline annotated BNA pattern characterizing a group of subjects identified as having normal brain function.

According to some embodiments of the invention the at least one previously annotated BNA pattern comprises at least one BNA pattern annotated as corresponding to a treated brain related disorder, and at least one baseline BNA pattern annotated as corresponding to an untreated brain related disorder.

According to some embodiments of the invention the at least one previously annotated BNA pattern is a baseline annotated BNA pattern being larger than the constructed BNA pattern in terms of at least one of: (i) an order, and (ii) a size of the BNA pattern.

According to some embodiments of the invention the method comprises calculating BNA pattern similarity based on the connectivity weights.

According to some embodiments of the invention the method comprises determining a brain-disorder index responsively to the BNA pattern similarity, wherein the brain-disorder corresponds to the annotation.

According to some embodiments of the invention the method comprises comparing the BNA pattern to at least one previously constructed BNA pattern of the same individual, and using the comparison for determining presence, absence and/or level of neural plasticity.

According to some embodiments of the invention the connectivity weight comprises a statistical score characterizing a relation between the pair and corresponding features in the reference data, the relation pertaining to at least one of latency, latency difference, amplitude and frequency.

According to some embodiments of the invention the method comprises constructing several BNA patterns corresponding to different time intervals, and displaying the BNA patterns on a time axis.

According to an aspect of some embodiments of the present invention there is provided a method of assessing a condition of a subject from neurophysiological data acquired from the brain of the subject. The method comprises: identifying activity-related features in the data; constructing a brain network activity (BNA) pattern having a plurality of nodes, each representing a feature of the activity-related features; calculating a first BNA pattern similarity describing a comparison between the constructed BNA pattern and a first baseline BNA pattern being annotated as normal; calculating a second BNA pattern similarity describing a comparison between the constructed BNA pattern and a second baseline BNA pattern being annotated as abnormal; and assessing the likelihood of abnormal brain function responsively to both the first and the second BNA pattern similarities.

According to some embodiments of the invention the method comprises assigning a connectivity weight to each pair of nodes in the BNA pattern, wherein the calculation of the first and the second BNA pattern similarities is based in part on the connectivity weight.

According to some embodiments of the invention the second baseline BNA pattern comprises at least one BNA pattern annotated as corresponding to an attention deficit hyperactivity disorder (ADHD).

According to some embodiments of the invention the method further comprises determining a brain-disorder index responsively to the first and the second BNA pattern similarities, wherein the brain-disorder corresponds to the annotation of the second baseline BNA pattern.

According to some embodiments of the invention the brain-disorder is ADHD.

According to an aspect of some embodiments of the present invention there is provided a method of assessing a likelihood of ADHD. The method comprises: identifying activity-related features in neurophysiological data acquired from the brain of a subject; constructing a brain network activity (BNA) pattern having a plurality of nodes, each representing a feature of the activity-related features; and calculating a BNA pattern similarity describing a comparison between the constructed BNA pattern and a baseline BNA pattern, the baseline BNA pattern having nodes representing event related potentials, predominantly at theta and alpha frequency bands, at a plurality of frontocentral locations within a characteristic time window of from about 100 ms to about 200 ms; wherein a BNA pattern similarity which is above a predetermined threshold indicates a likelihood of the subject having ADHD.

According to some embodiments of the invention the neurophysiological data comprises data acquired before, during and/or after a treatment.

According to some embodiments of the invention the method comprises assessing the effect of the treatment by comparing a BNA pattern corresponding to data acquired before a treatment to a BNA pattern corresponding to data acquired during and/or after a treatment.

According to some embodiments of the invention the treatment comprises a pharmacological treatment employing an active agent and a placebo treatment employing a placebo agent, and wherein the method comprises assessing the effect of the pharmacological treatment by comparing a BNA pattern corresponding to data acquired during and/or after the a placebo treatment to a BNA pattern corresponding to data acquired during and/or after the pharmacological treatment.

According to some embodiments of the invention the active agent comprises scopolamine. According to some embodiments of the invention the active agent comprises ketamine. According to some embodiments of the invention the active agent comprises methylphenidate. According to some embodiments of the invention the active agent comprises a neuroleptic agent.

According to some embodiments of the invention the active agent is selected from the group consisting of scopolamine, ketamine, methylphenidate, donepezil, physostigmine, tacrine, fluoxetine, carbamazepine, amantadine, apomorphine, bromocriptine, levodopa, pergolide, ropinirole, selegiline, trihexyphenidyl, atropine, scopolamine, glycopyrrolate, baclofen, diazepam, tizanidine and dantrolene.

According to some embodiments of the invention the treatment comprises a surgical intervention.

According to some embodiments of the invention the treatment comprises a rehabilitative treatment.

According to some embodiments of the invention the treatment comprises phototherapy.

According to some embodiments of the invention the treatment comprises hyperbaric therapy.

According to some embodiments of the invention the treatment comprises at least one treatment selected from the group consisting of neural feedback, EMG biofeedback, EEG neurofeedback, transcranial magnetic stimulation (TMS) and direct electrode stimulation.

According to an aspect of some embodiments of the present invention there is provided a system for analyzing neurophysiological data. The system comprises a data processor configured for receiving the neurophysiological data, and executing at least some of the operations described herein.

According to an aspect of some embodiments of the present invention there is provided a computer software product. The computer software product comprises a computer-readable medium in which program instructions are stored, which instructions, when read by a data processor, cause the data processor to receive the neurophysiological data and execute the at least some of the operations described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flowchart diagram of a method suitable for analyzing neurophysiological data, according to various exemplary embodiments of the present invention.

FIG. 2 is a schematic illustration showing a representative example of a Brain Network Activity (BNA) pattern which can be extracted from neurophysiological data, according to some embodiments of the present invention.

FIG. 3A is a flowchart diagram describing a procedure for identifying activity-related features for a group of subjects, according to some embodiments of the present invention.

FIG. 3B is schematic illustration of a procedure for determining relations between brain activity features, according to some embodiments of the present invention;

Figure 3A:
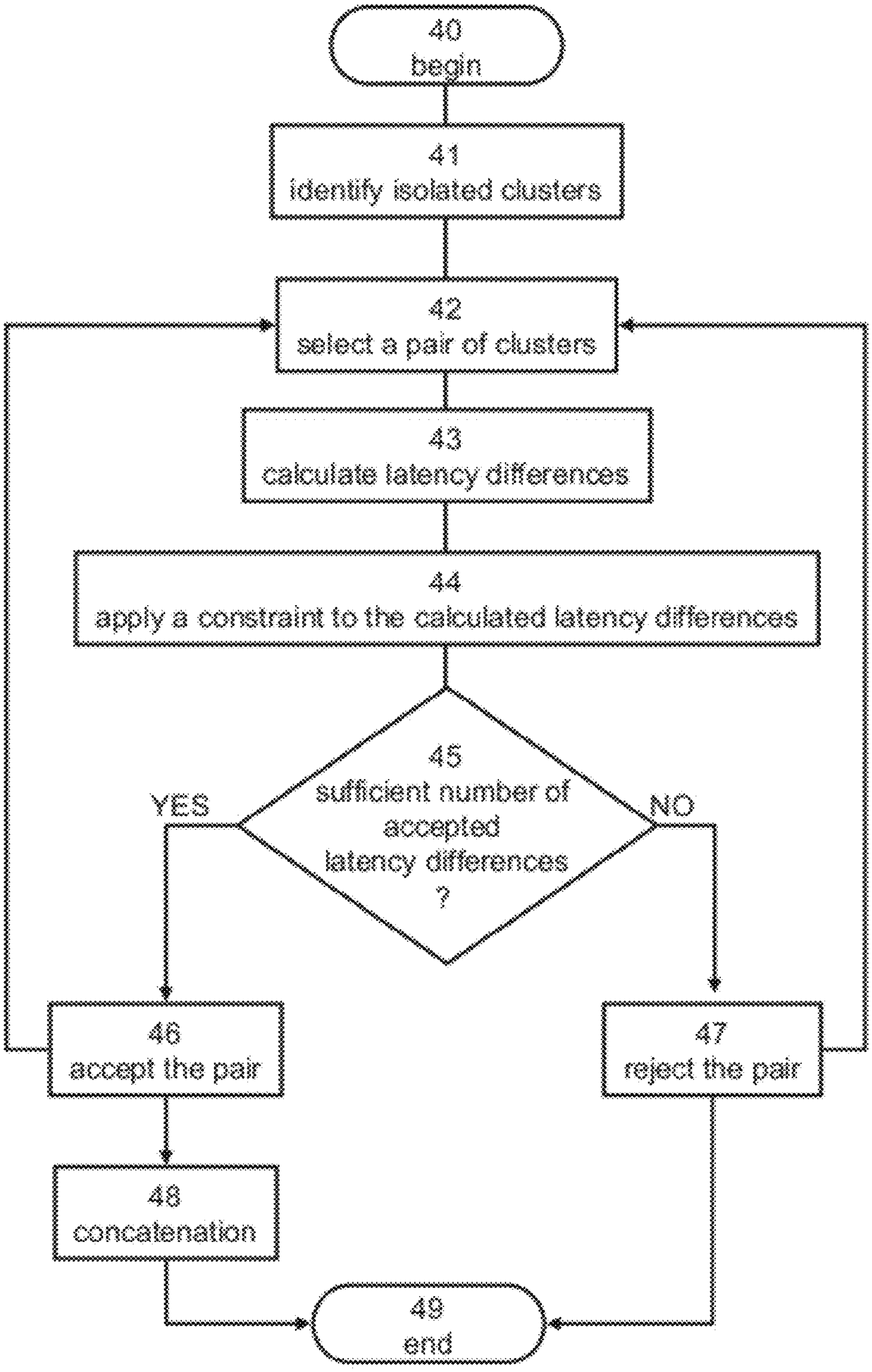
Figure 3B:
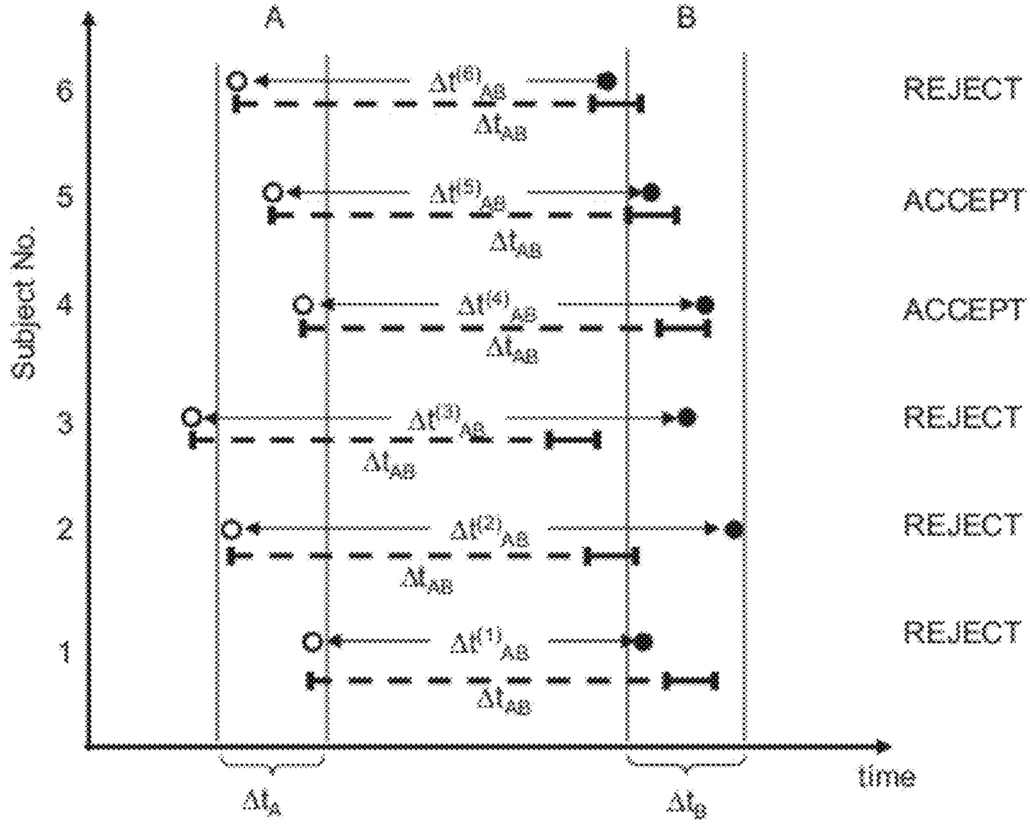
Figure 3C:
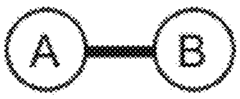
Figure 3D:
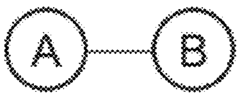
Figure 3E:
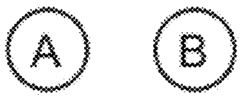
Figure 4:
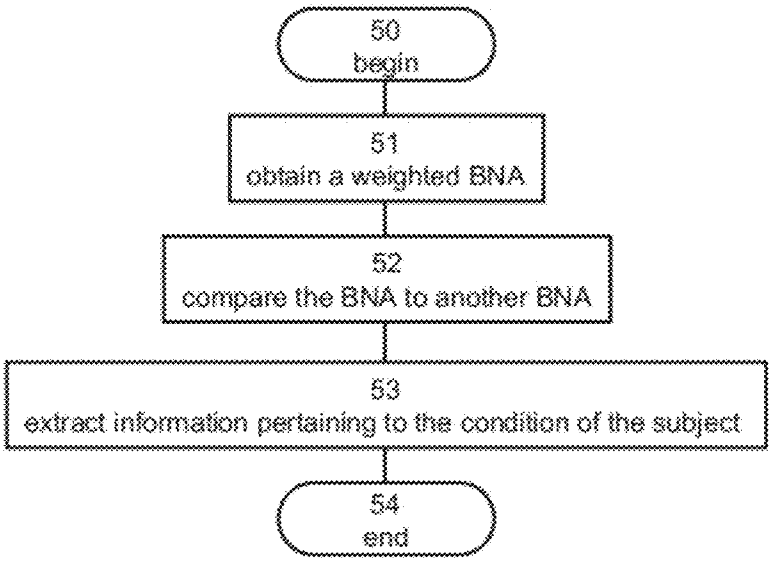

FIGS. 3C-E are abstract illustrations of a BNA patterns constructed according to some embodiments of the present invention using the procedure illustrated in FIG. 3B;

FIG. 4 is a flowchart diagram describing a method suitable for analyzing a subject-specific BNA pattern, according to various exemplary embodiments of the present invention.

FIGS. 5A-F are schematic illustrations showing a representative example for a process for determining a brain-disorder index, according to some embodiments of the present invention.

FIGS. 6A-F are schematic illustrations showing representative examples for a process for assessing the responsiveness of an ADHD subject to treatment, according to some embodiments of the present invention.

FIGS. 7A-D are schematic illustrations showing representative examples for a process for assessing the responsiveness of another ADHD subject to treatment, according to some embodiments of the present invention.

FIGS. 8A-E are schematic illustrations showing a representative example for a process for assessing the responsiveness of a subject to scopolamine, according to some embodiments of the present invention.

Figure 9A:
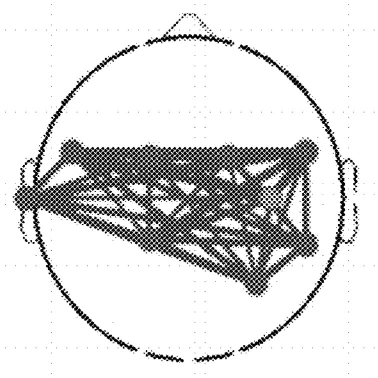
Figure 9B:
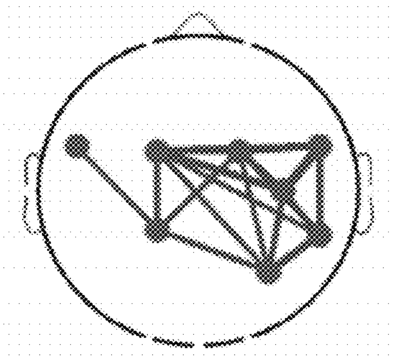

FIGS. 9A-B are schematic illustrations showing a representative example for use of the BNA pattern for measuring pain, according to some embodiments of the present invention.

FIGS. 10A-H are schematic illustrations of BNA patterns constructed according to some embodiments of the present invention from EEG data recorded during a working memory test.

Figure 11:
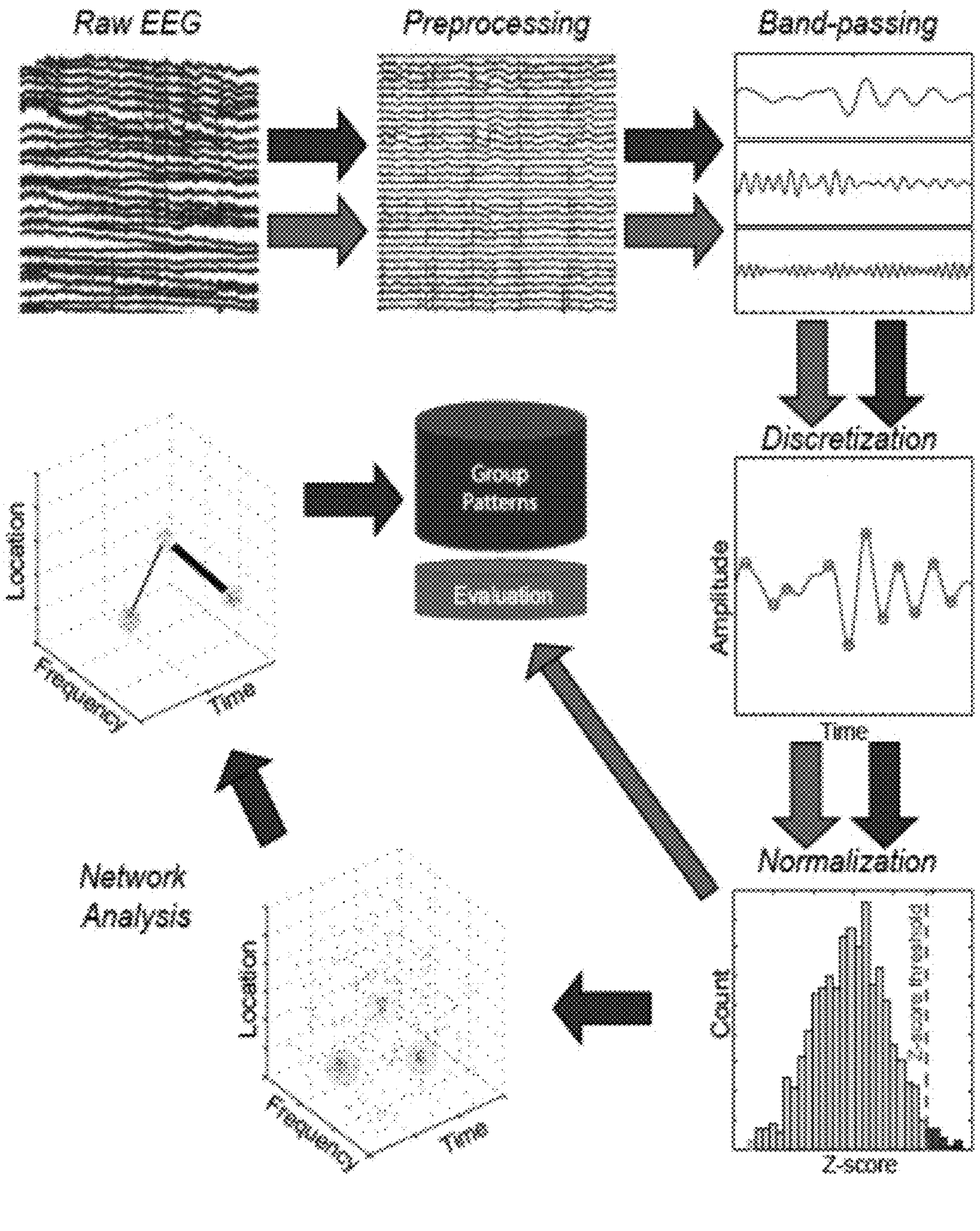

FIG. 11 is a scheme illustrating a method employed during experiments performed in accordance with some embodiments of the present invention.

Figure 12:
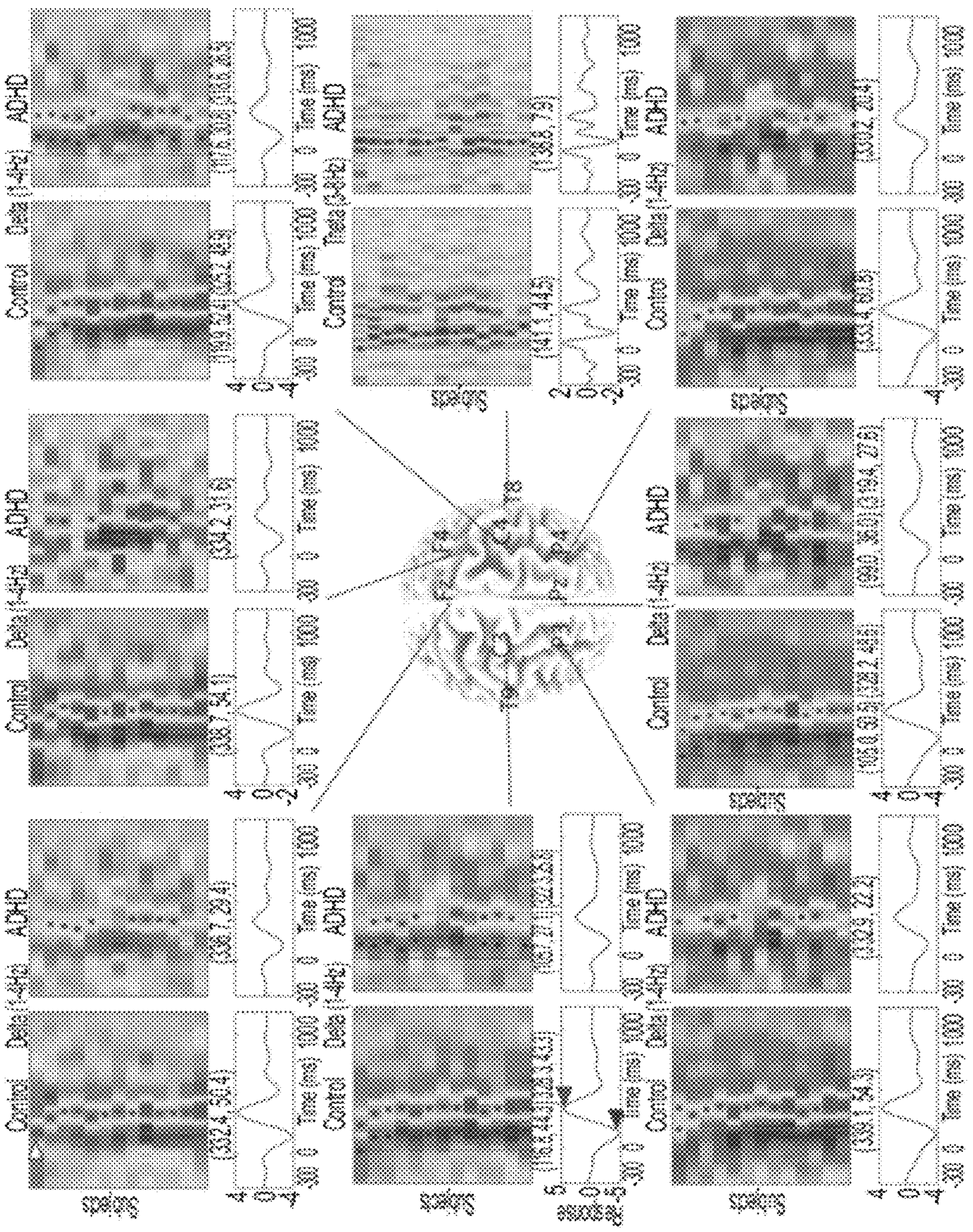

FIG. 12 shows patterns of electrode activity obtained in accordance with some embodiments of the present invention during a Go/No-go test, wherein the patterns are more characteristic to a Control group No-go activity and less characteristic to an ADHD group No-go activity.

Figure 13:
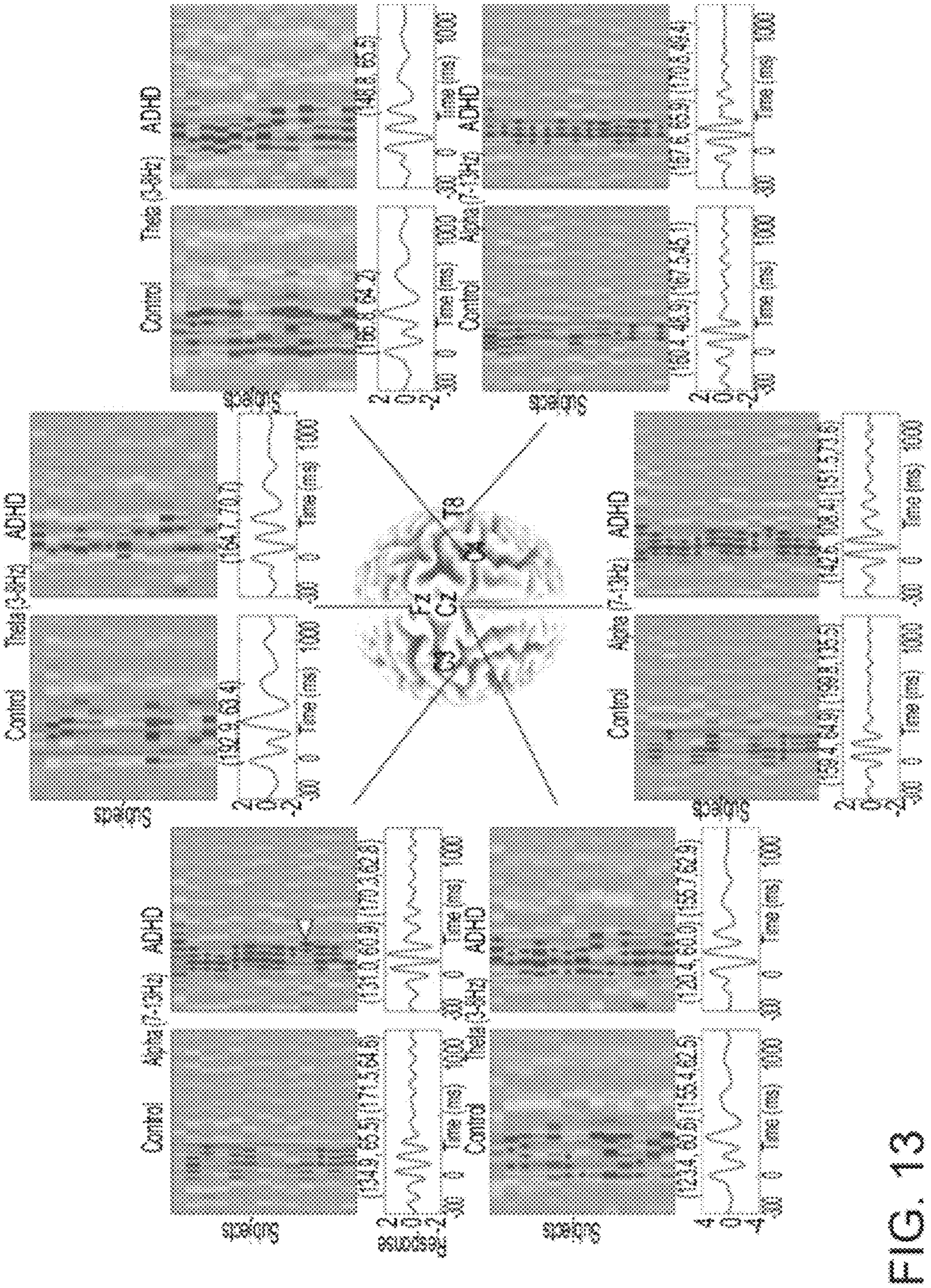

FIG. 13 shows patterns of electrode activity obtained in accordance with some embodiments of the present invention during a Go/No-go test, wherein the patterns are more characteristic to the ADHD group No-go activity and less characteristic to the Control group No-go activity.

FIGS. 14A-B are schematic illustrations of distinguishing BNA patterns corresponding to the patterns shown in FIGS. 12 and 13, respectively, as constructed according to some embodiments of the present invention.

FIGS. 15A-F are schematic illustrations showing classification of a novel subject as either ADHD or Control, according to some embodiments of the present invention.

Figure 16:
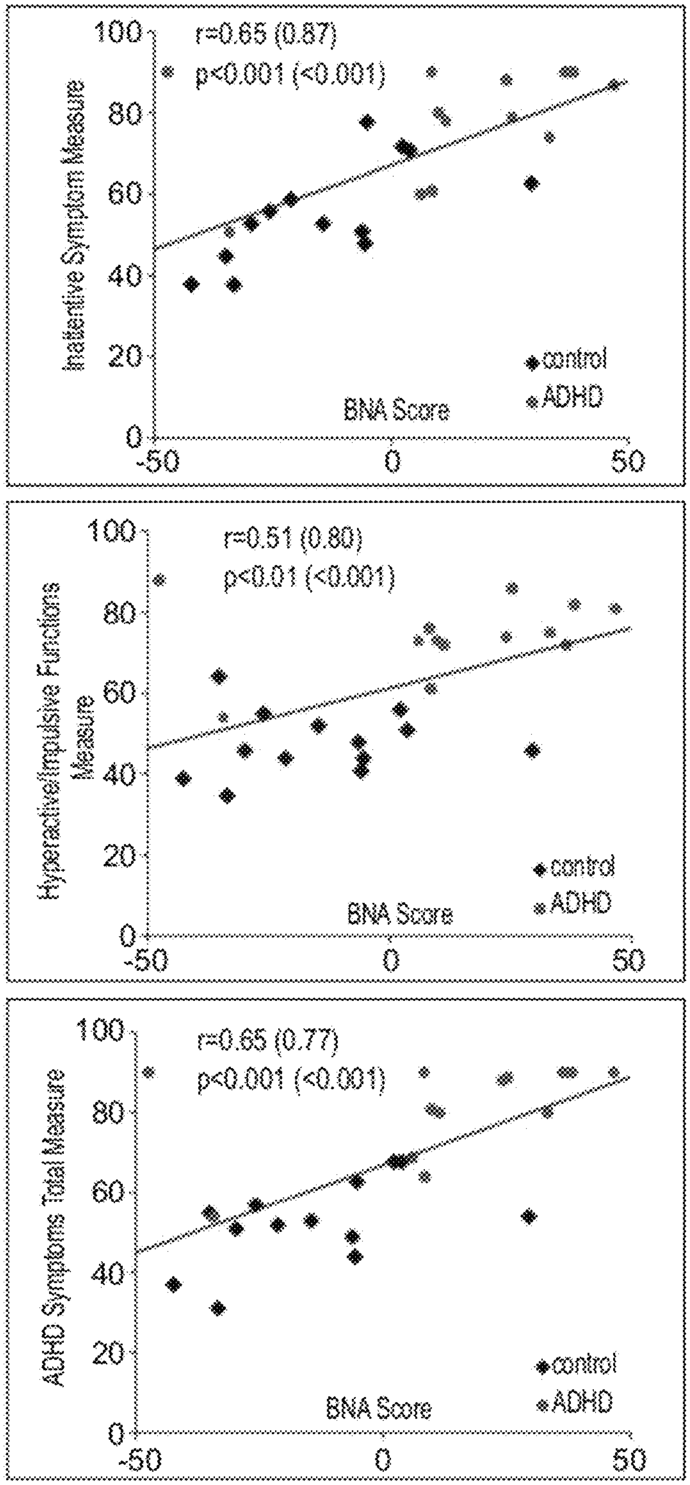

FIG. 16 shows correlations between conventional ADHD measures and ADHD indices calculated according to some embodiments of the present invention.

FIGS. 17A-B show a baseline BNA pattern (FIG. 17A) as constructed according to some embodiments of the present invention, and an fMRI (FIG. 17B) which are characteristic to a healthy control hand activation.

FIG. 18 is a conventional CT scan of a hemi-paresis subject following 9 treatment sessions.

FIG. 19 shows BNA pattern analysis of the hemi-paresis subject, wherein the analysis comprises comparison of a subject-specific BNA pattern to a group BNA pattern according to some embodiments of the present invention.

FIG. 20 is a schematic illustration of a late stage BNA pattern constructed hemi-paresis subject according to some embodiments of the present invention.

FIG. 21 shows BNA pattern analysis of the hemi-paresis subject, wherein the analysis comprises comparison of a subject-specific BNA pattern to a late stage BNA pattern according to some embodiments of the present invention.

FIG. 22 is a schematic illustration showing an arrangement of electrodes employed according to some embodiments of the present invention during an experiment for monitoring acute pain.

FIGS. 23A-B are schematic illustration showing group BNA patterns constructed for subjects following exposure to a baseline temperature (FIG. 23A) and a high temperature (FIG. 23A).

FIGS. 24A-B show representative examples of single electrode activities as measured during exposure to a high temperature (FIG. 24A) and a baseline temperature (FIG. 24B).

Figure 25:
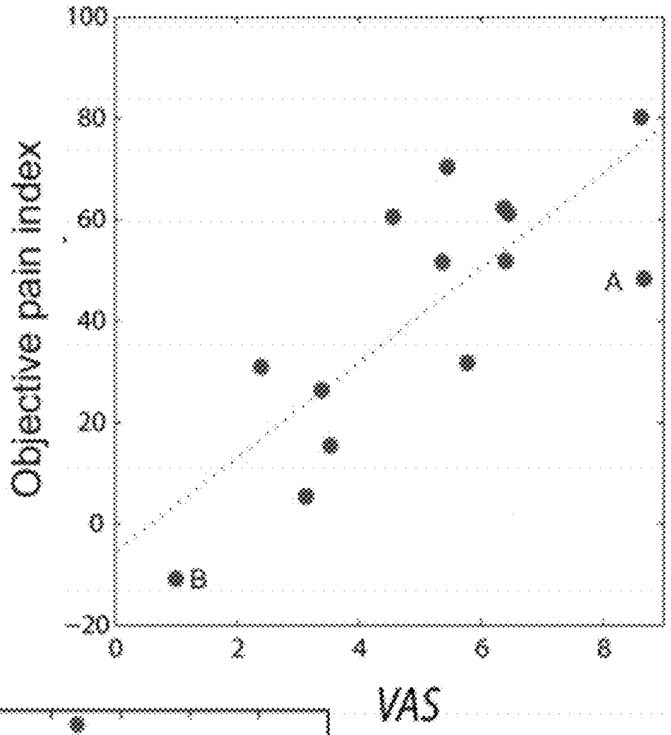

FIG. 25 shows correlation between objective pain index as calculated according to some embodiments of the present invention and a subjective pain score on a Visual Analog Scale.

Figure 26:
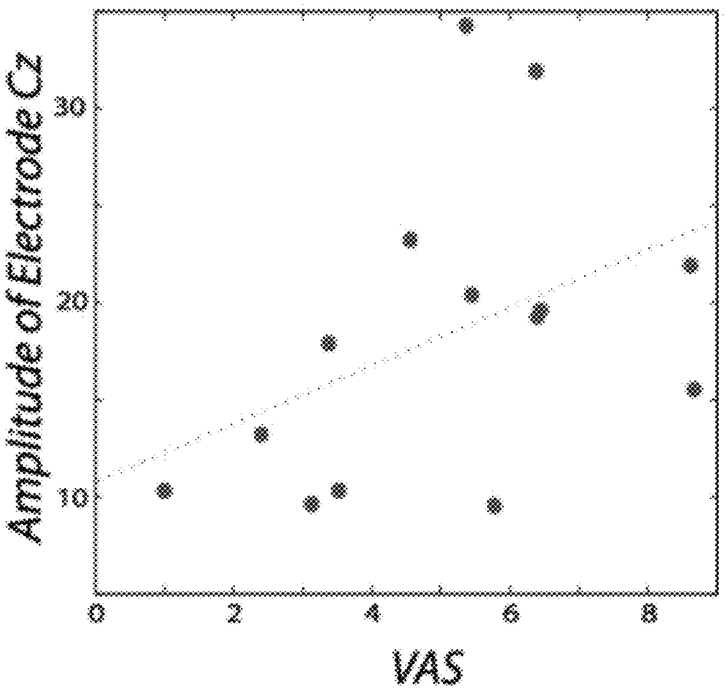

FIG. 26 shows correlation between an amplitude of a single electrode and the subjective pain score on a Visual Analog Scale.

FIGS. 27A-D show patterns of electrode activity obtained in accordance with some embodiments of the present invention during neural detection of target stimuli in an oddball test, wherein the patterns are more characteristic to a placebo group and less characteristic to a scopolamine group.

FIGS. 28A-C show patterns of electrode activity obtained in accordance with some embodiments of the present invention during neural detection of target stimuli, wherein the patterns are more characteristic to the scopolamine group and less characteristic to the placebo group.

FIGS. 29A-D show patterns of electrode activity obtained in accordance with some embodiments of the present invention during neural detection of novel stimuli in an oddball test, wherein the patterns are more characteristic to the placebo group and less characteristic to the scopolamine group.

Figure 30A:
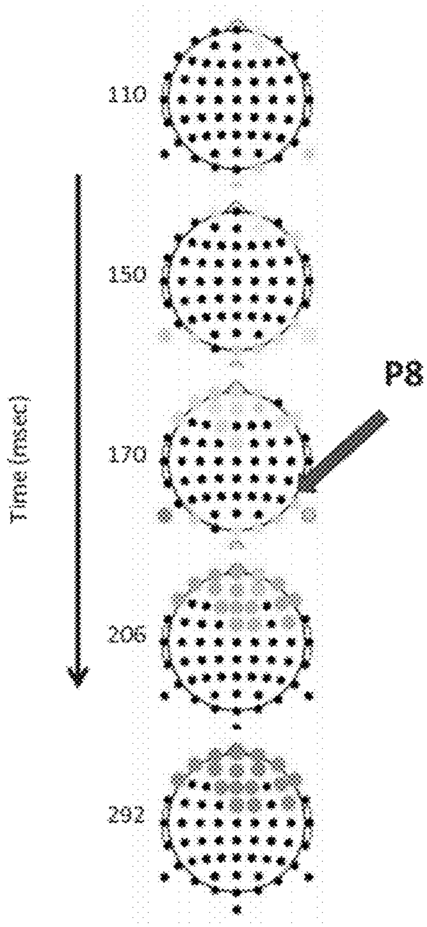
Figure 30B:
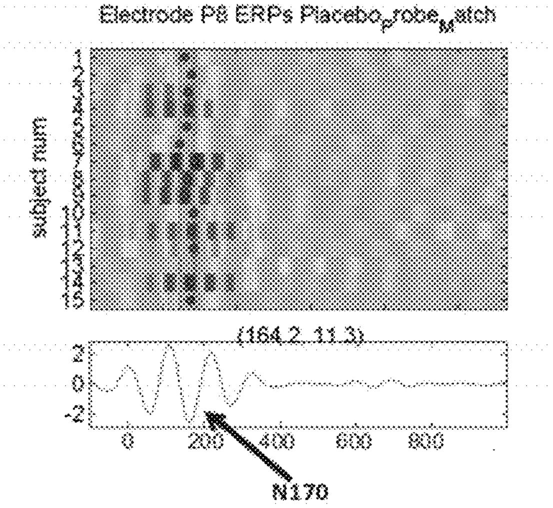
Figure 30C:
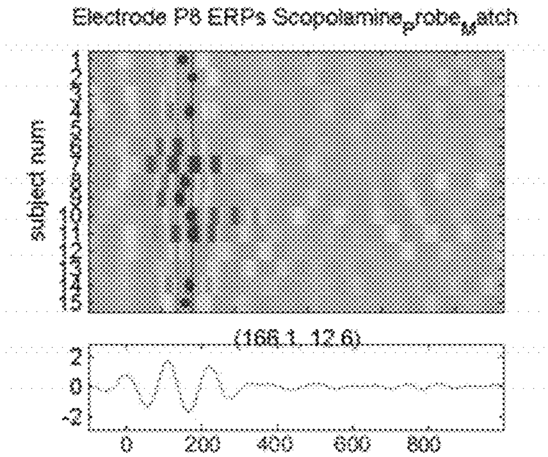

FIGS. 30A-C show patterns of electrode activity obtained in accordance with some embodiments of the present invention during the retrieval process in a working memory test, wherein the patterns are more characteristic to the placebo group and less characteristic to the scopolamine group.

FIGS. 31A-E show patterns of electrode activity obtained in accordance with some embodiments of the present invention during the retrieval process in a working memory test, wherein the patterns are more characteristic to the scopolamine group and less characteristic to the placebo group.

Figure 32A:
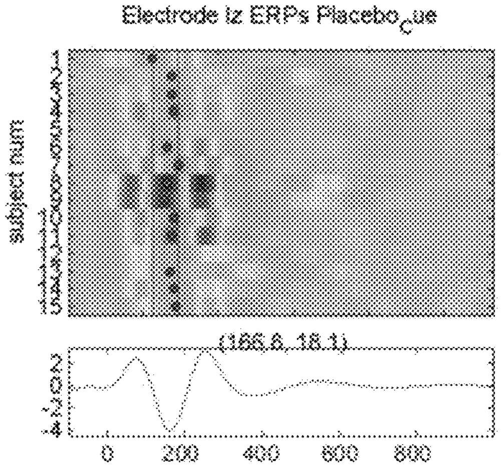
Figure 32B:
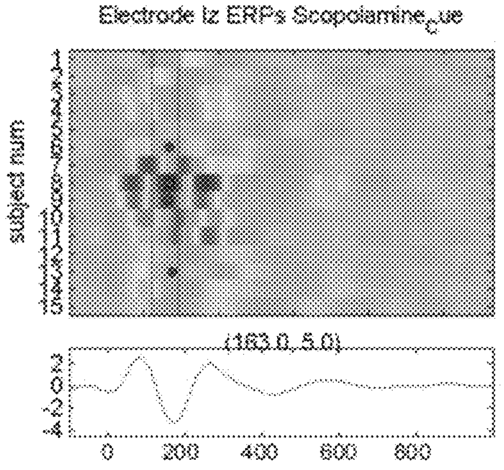

FIGS. 32A-B show IZ electrode activity patterns obtained in accordance with some embodiments of the present invention during neural memorizing process in a working memory test, wherein the patterns are more characteristic to the placebo group and less characteristic to the scopolamine group.

FIGS. 33A-D are the same as FIGS. 32A-B for a P9 electrode.

Figure 33A:
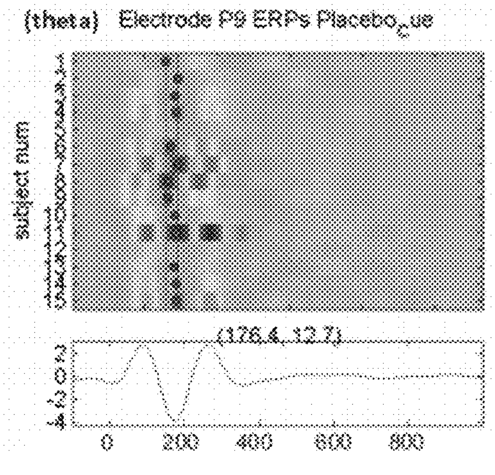
Figure 33B:
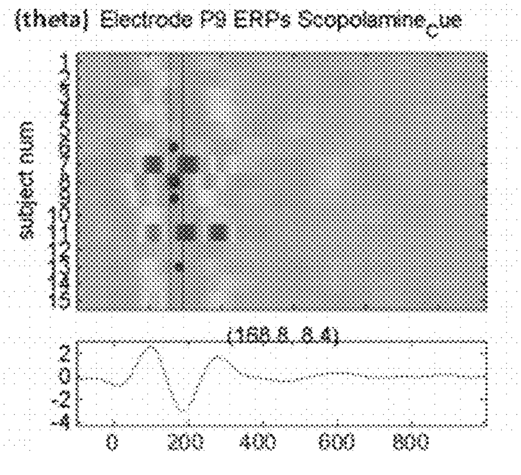
Figure 33C:
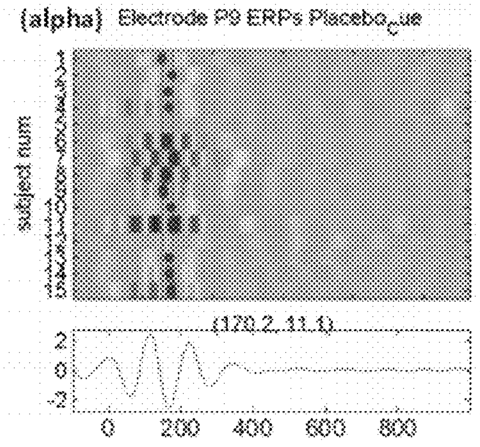
Figure 33D:
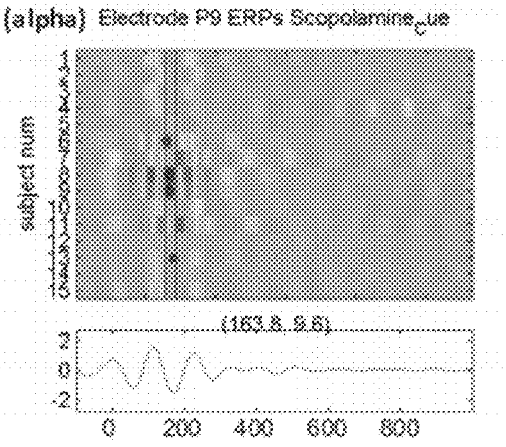
Figure 33E:
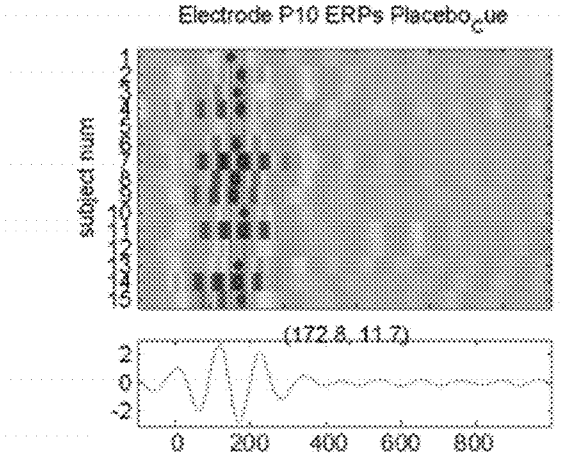
Figure 33F:
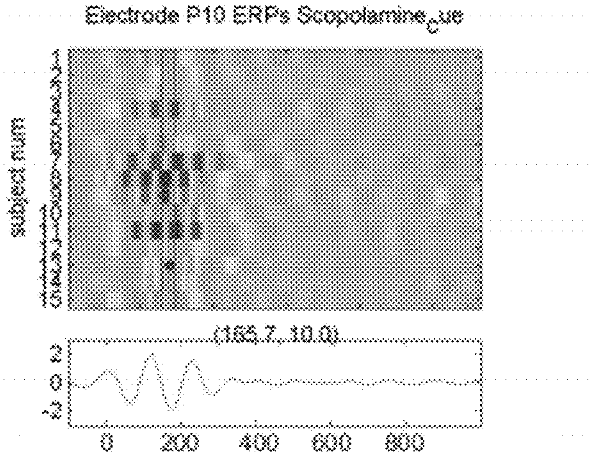

FIGS. 33E-F are the same as FIGS. 32A-B for a P10 electrode.

Figure 34A:
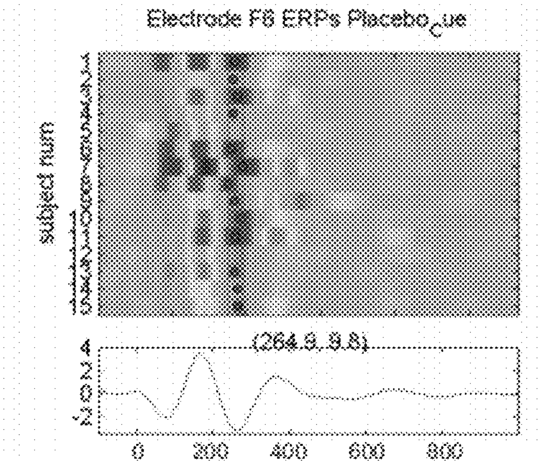
Figure 34B:
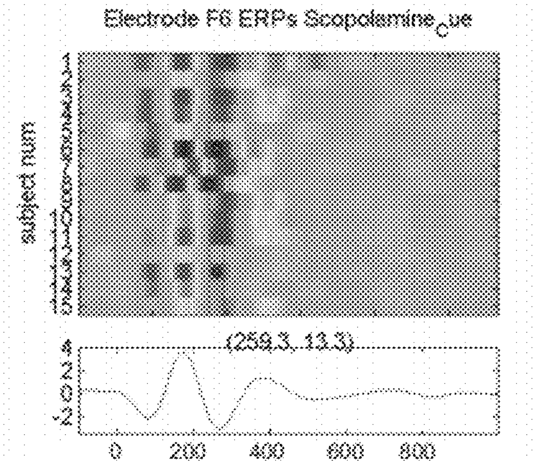

FIGS. 34A-B are the same as FIGS. 32A-B for an F6 electrode.

Figure 35A:
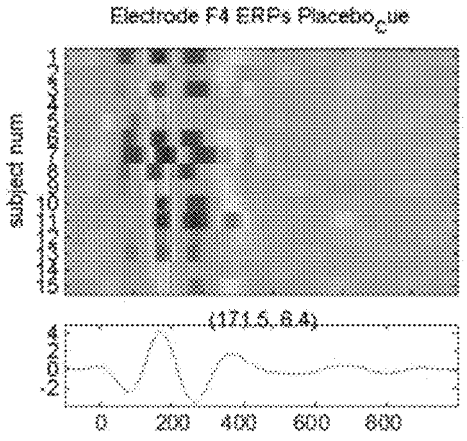
Figure 35B:
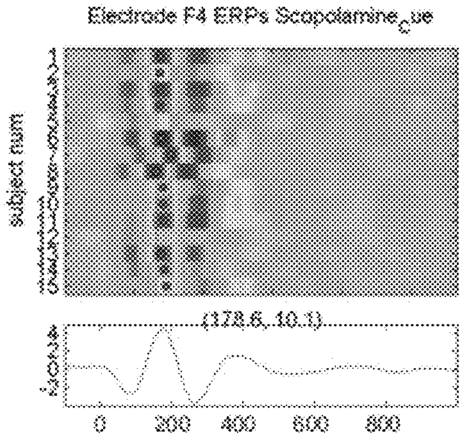

FIGS. 35A-B show F4 electrode activity patterns obtained in accordance with some embodiments of the present invention during neural memorizing process in a working memory test, wherein the patterns are more characteristic to the scopolamine group and less characteristic to the placebo group.

FIGS. 36A-C show patterns of electrode activity obtained in accordance with some embodiments of the present invention, wherein the patterns are more characteristic to subjects with Alzheimer's disease (AD) and less characteristic to subjects with mild cognitive impairment (MCI).

FIGS. 37A-C show patterns of electrode activity obtained in accordance with some embodiments of the present invention, wherein the patterns are more characteristic to subjects with MCI and less characteristic to subjects with AD.

FIG. 38 shows graphical presentation of a brain-disorder index according to some embodiments of the present invention.

FIG. 39 shows results of a methylphenidate (MPH) study performed according to some embodiments of the present invention.

Figure 40:
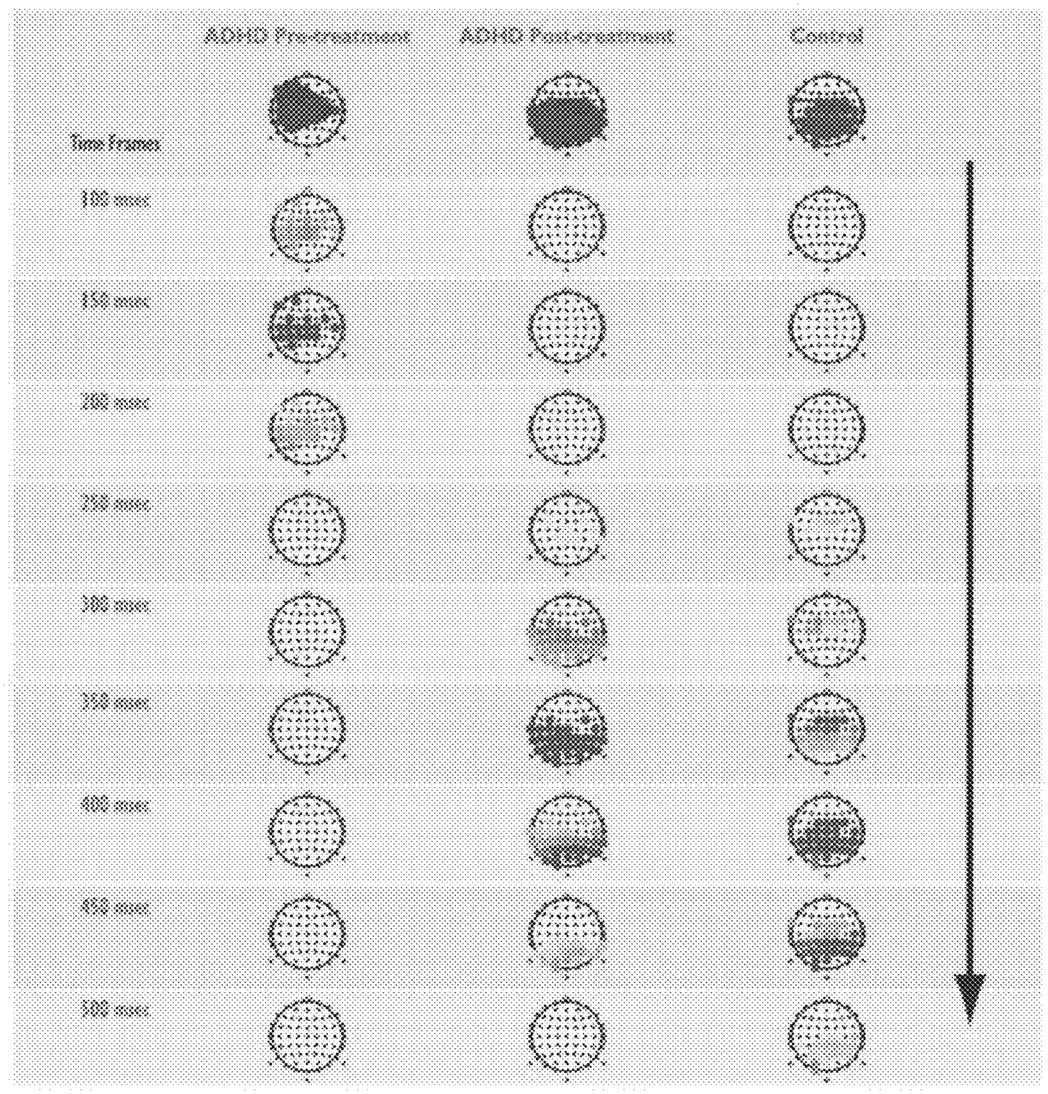

FIG. 40 shows evolutions of group BNA patterns of untreated ADHD subjects (left column), ADHD subjects following treatment with MPH (middle column), and control (right column).

FIGS. 41A-D show results obtained in a working memory study performed according to some embodiments of the present invention for two groups, where a first group included data collected during an encoding process from subjects treated with placebo, and a second group included data collected during the retrieval process from subjects treated with placebo.

FIGS. 42A-D show results obtained in a working memory study performed according to some embodiments of the present invention for two groups, where a first group included data collected during an encoding process from subjects treated with placebo, and a second group included data collected during the encoding process from subjects treated with Scopolamine.

FIGS. 43A-D show results obtained in a working memory study performed according to some embodiments of the present invention for two groups, where a first group included data collected during a retrieval process from subjects treated with placebo, and a second group included data collected during a retrieval process from subjects treated with Scopolamine.

DESCRIPTION OF SPECIFIC EMBODIMENTS OF THE INVENTION

The present invention, in some embodiments thereof, relates to neurophysiology and, more particularly, but not exclusively, to method and system for analyzing neurophysiological data.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Embodiments of the present invention are directed to a tool which can be used for an individual subject or a group of subjects, to analyze their brain activity so as to identify neuropsychological patterns related to behavior, and to construct brain network activity (BNA) pattern. The BNA pattern can be classified, optionally and preferably by comparing it to one or more previously annotated BNA patterns. The BNA pattern can aid both for diagnostics and for therapy for treating pathologies associated with the BNA pattern.

Figure 1:
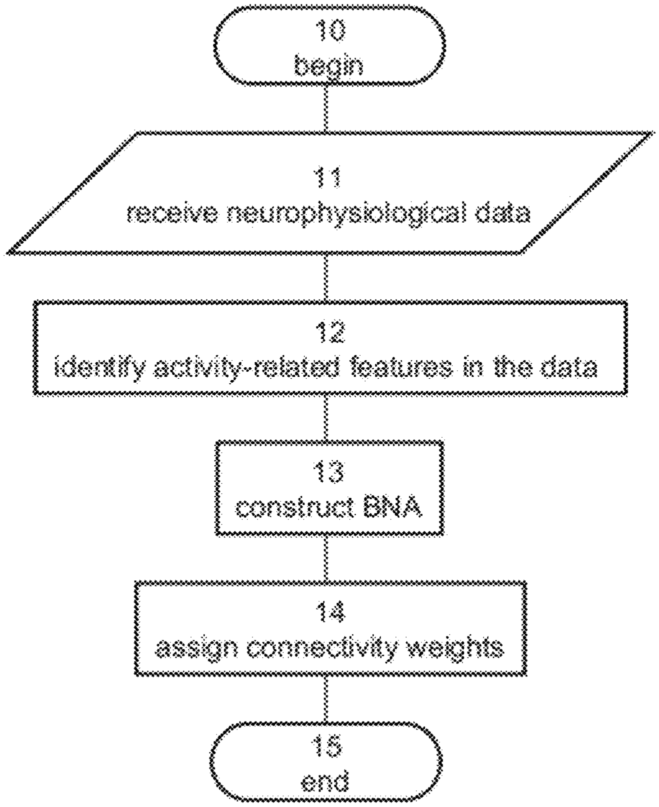

FIG. 1 is a flowchart diagram of a method suitable for analyzing neurophysiological data, according to various exemplary embodiments of the present invention. It is to be understood that, unless otherwise defined, the operations described hereinbelow can be executed either contemporaneously or sequentially in many combinations or orders of execution. Specifically, the ordering of the flowchart diagrams is not to be considered as limiting. For example, two or more operations, appearing in the following description or in the flowchart diagrams in a particular order, can be executed in a different order (e.g., a reverse order) or substantially contemporaneously. Additionally, several operations described below are optional and may not be executed.

At least part of the operations can be can be implemented by a data processing system, e.g., a dedicated circuitry or a general purpose computer, configured for receiving the data and executing the operations described below.

Computer programs implementing the method of the present embodiments can commonly be distributed to users on a distribution medium such as, but not limited to, a floppy disk, a CD-ROM, a flash memory device and a portable hard drive. From the distribution medium, the computer programs can be copied to a hard disk or a similar intermediate storage medium. The computer programs can be run by loading the computer instructions either from their distribution medium or their intermediate storage medium into the execution memory of the computer, configuring the computer to act in accordance with the method of this invention. All these operations are well-known to those skilled in the art of computer systems.

The method of the present embodiments can be embodied in many forms. For example, it can be embodied in on a tangible medium such as a computer for performing the method operations. It can be embodied on a computer readable medium, comprising computer readable instructions for carrying out the method operations. In can also be embodied in electronic device having digital computer capabilities arranged to run the computer program on the tangible medium or execute the instruction on a computer readable medium.

The neurophysiological data to be analyzed can be any data acquired directly from the brain of the subject under investigation. The data acquired "directly" in the sense that it shows electrical, magnetic, chemical or structural features of the brain tissue itself. The neurophysiological data can be data acquired directly from the brain of a single subject or data acquired directly from multiple brains of respective multiple subjects (e.g., a research group), not necessarily simultaneously.

Analysis of data from multiple brains can be done by performing the operations described below separately for each portion of the data that correspond to a single brain. Yet, some operations can be performed collectively for more than one brain. Thus, unless explicitly state otherwise, a reference to "subject" or "brain" in the singular form does not necessarily mean analysis of data of an individual subject. A reference to "subject" or "brain" in the singular form encompasses also analysis of a data portion which corresponds to one out of several subjects, which analysis can be applied to other portions as well.

The data can be analyzed immediately after acquisition ("online analysis"), or it can be recorded and stored and thereafter analyzed ("offline analysis").

Representative example of neurophysiological data types suitable for the present invention, including, without limitation, electroencephalogram (EEG) data, magnetoencephalography (MEG) data, computer-aided tomography (CAT) data, positron emission tomography (PET) data, magnetic resonance imaging (MRI) data, functional MRI (fMRI) data, ultrasound data, single photon emission computed tomography (SPECT) data, Brain Computer Interface (BCI) data, and data from neuroprostheses at the neural level. Optionally, the data include combination of two or more different types of data.

In various exemplary embodiments of the invention the neurophysiological data are associated with signals collected using a plurality of measuring devices respectively placed at a plurality of different locations on the scalp of the subject. In these embodiments, the data type is preferably EEG or MEG data. The measuring devices can include electrodes, superconducting quantum interference devices (SQUIDs), and the like. The portion of the data that is acquired at each such location is also referred to as "channel." In some embodiments, the neurophysiological data are associated with signals collected using a plurality of measuring devices placed in the brain tissue itself. In these embodiments, the data type is preferably invasive EEG data, also known as electrocorticography (ECoG) data.

Optionally and preferably, the neurophysiological data is collected at least before and after the subject has performed a task and/or action. In some embodiments of the present invention the neurophysiological data is collected at least before and after the subject has conceptualized a task and/or action but has not actually performed the task. These embodiments are useful when the subject is suffering from some type of physical and/or cognitive deficit that may prevent actual execution of a task and/or action, as for example may be seen in response to various brain injuries such as stroke. Nevertheless, these embodiments can be employed for any subject, if desired.

Neurophysiological data which is associated with a task and/or action (whether actually performed or conceptualized) can be used as event related measures, such as event related potentials (ERPs) or event related fields (ERFs). The task and/or action (whether actually performed or conceptualized) is preferably in response to a stimulus or stimuli, and the acquisition of data is synchronized with the stimulus to establish a timeline of the response and extract data features responsively to this timeline. Typically, but not necessarily, the data collection is on-going such that neurophysiological data are collected continuously before, during and after performance or conceptualization of the task and/or action.

Various types of tasks are contemplated, both lower-level and higher-level cognitive tasks and/or actions. The task/action can be single, serial or on-going. An example of an on-going lower-level cognitive task/action includes, without limitation, watching a movie; an example of a single lower-level cognitive task/action includes, without limitation, providing an audible signal (e.g., a simple sound) to the subject; and an example of a serial lower-level cognitive task/action includes, without limitation, playing an audible signal repeatedly. It is appreciated that for a repetitive task the subject may eventually be conditioned and will pay less attention (a process known as habituation), but there still will be a response from the brain. An example of a higher-level cognitive task/action includes, without limitation, the so called "Go/NoGo task" in which the subject is requested to push a button if a high pitch sound is heard, wherein if a low pitch sound is heard then the subject is not to push the button. This task is known in the art and is used in many cognitive studies.

Many protocols of stimuli and stimuli-responses are known in the art, all of which are contemplated by some embodiments of the present invention. Stimulus-response neuropsychological tests include, without limitation, the Stroop task, the Wisconsin card sorting test, and the like; stimulus-only based tests include, without limitation, mismatch negativity, brain-stem-evoked response audiometry (BERA), and the like. Also contemplated are response-only based tests, such as, but not limited to, saccade analysis, movement related potentials (MRP), N-back memory tasks and other working memory tasks, the "serial seven" test (counting back from 100 in jumps of seven), the Posner attention tasks and the like.

It is to be understood that it is not intended to limit the scope of the present invention only to neurophysiological data associated with stimulus, task and/or action. Embodiments of the present invention can be applied also to neurophysiological data describing spontaneous brain activity. Also contemplated are embodiments in which the neurophysiological data are acquired during particular activities, but the acquisition is not synchronized with a stimulus.

Referring now to FIG. 1, the method begins at 10 and optionally and preferably continues to 11 at which the neurophysiological data are received. The data can be recorded directly from the subject or it can be received from an external source, such as a computer readable memory medium on which the data are stored.

The method continues to 12 at which relations between features of the data are determined so as to identify activity-related features. This can be done using any procedure known in the art. For example, procedures as described in International Publication Nos. WO 2007/138579, WO 2009/069134, WO 2009/069135 and WO 2009/069136, the contents of which are hereby incorporated by reference, can be employed. Broadly speaking, the extraction of activity-related features includes multidimensional analysis of the data, wherein the data is analyzed to extract spatial and non-spatial characteristics of the data.

The spatial characteristics preferably describe the locations from which the respective data were acquired. For example, the spatial characteristics can include the locations of the measuring devices (e.g., electrode, SQUID) on the scalp of the subject.

Also contemplated are embodiments in which the spatial characteristics estimate the locations within the brain tissue at which the neurophysiological data were generated. In these embodiments, a source localization procedure, which may include, for example, low resolution electromagnetic tomography (LORETA), is employed. A source localization procedure suitable for the present embodiments is described in the aforementioned international publications which are incorporated by reference. Other source localization procedure suitable for the present embodiments are found in Greenblatt et al., 2005, "Local Linear Estimators for the Bioelectromagnetic Inverse Problem," IEEE Trans. Signal Processing, 53(9):5430; Sekihara et al., "Adaptive Spatial Filters for Electromagnetic Brain Imaging (Series in Biomedical Engineering)," Springer, 2008; and Sekihara et al., 2005, "Localization bias and spatial resolution of adaptive and non-adaptive spatial filters for MEG source reconstruction," NeuroImage 25:1056; the contents of which are hereby incorporated by reference.

Additionally contemplated are embodiments in which the spatial characteristics estimate locations on the epicortical surface. In these embodiments, data collected at locations on the scalp of the subject are processed so as to map the scalp potential distribution onto the epicortical surface. The technique for such mapping is known in the art and referred to in the literature as Cortical Potential Imaging (CPI) or Cortical Source Density (CSD). Mapping techniques suitable for the present embodiments are found in Kayser et al., 2006, "Principal Components Analysis of Laplacian Waveforms as a Generic Method for Identifying ERP Generator Patterns: I. Evaluation with Auditory Oddball Tasks," Clinical Neurophysiology 117(2):348; Zhang et al., 2006, "A Cortical Potential Imaging Study from Simultaneous Extra- and Intra-cranial Electrical Recordings by Means of the Finite Element Method," Neuroimage, 31(4): 1513; Perrin et al., 1987, "Scalp Current Density Mapping: Value and Estimation from Potential Data," IEEE transactions on biomedical engineering, BME-34(4):283; Ferree et al., 2000, "Theory and Calculation of the Scalp Surface Laplacian"; and Babiloni et al., 1997, "High resolution EEG: a new model-dependent spatial deblurring method using a realistically-shaped MR-constructed subject's head model," Electroencephalography and clinical Neurophysiology 102:69

In any of the above embodiments, the spatial characteristics can be represented using a discrete or continuous spatial coordinate system, as desired. When the coordinate system is discrete, it typically corresponds to the locations of the measuring devices (e.g., locations on the scalp, epicortical surface, cerebral cortex or deeper in the brain). When the coordinate system is continuous, it preferably describes the approximate shape of the scalp or epicortical surface, or some sampled version thereof. A sampled surface can be represented by a point-cloud which is a set of points in a three-dimensional space, and which is sufficient for describing the topology of the surface. For a continuous coordinate system, the spatial characteristics can be obtained by piecewise interpolation between the locations of the measuring devices. The piecewise interpolation preferably utilizes a smooth analytical function or a set of smooth analytical functions over the surface.

In some embodiments of the invention the non-spatial characteristics are obtained separately for each spatial characteristic. For example, the non-spatial characteristics can be obtained separately for each channel. When the spatial characteristics are continuous, the non-spatial characteristics are preferably obtained for a set of discrete points over the continuum. Typically, this set of discrete points includes at least the points used for the piecewise interpolation, but may also include other points over the sampled version of the surface.

The non-spatial characteristics preferably include temporal characteristics, which are obtained by segmenting the data according to the time of acquisition. The segmentation results in a plurality of data segments each corresponding to an epoch over which the respective data segment was acquired. The length of the epoch depends on the temporal resolution characterizing the type f neurophysiological data. For example, for EEG or MEG data, a typical epoch length is approximately 1000 ms.

Other non-spatial characteristics can be obtained by data decomposing techniques. In various exemplary embodiments of the invention the decomposition is performed separately for each data segment of each spatial characteristic. Thus, for a particular data channel, decomposition is applied, e.g., sequentially to each data segment of this particular channel (e.g., first to the segment that corresponds to the first epoch, then to the segment that correspond to the second epoch and so on). Such sequential decomposition is performed for other channels as well.

The neurophysiological data can be decomposed by identifying a pattern of peaks in the data, or, more preferably by means of waveform analysis, such as, but not limited to, wavelet analysis. In some embodiments of the present invention the peak identification is accompanied by a definition of a spatiotemporal neighborhood of the peak. The neighborhood can be defined as a spatial region (two- or three-dimensional) in which the peak is located and/or a time-interval during which the peak occurs. Preferably, both a spatial region and time-interval are defined, so as to associate a spatiotemporal neighborhood for each peak. The advantage of defining such neighborhoods is that they provide information regarding the spreading structure of the data over time and/or space. The size of the neighborhood (in terms of the respective dimension) can be determined based on the property of the peak. For example, in some embodiments, the size of the neighborhood equals the full width at half maximum (FWHM) of the peak. Other definitions of the neighborhood are not excluded from the scope of the present invention.

The waveform analysis is preferably accompanied by filtering (e.g., bandpass filtering) such that the wave is decomposed to a plurality of overlapping sets of signal peaks which together make up the waveform. The filters themselves may optionally be overlapping.

When the neurophysiological data comprise EEG data, one or more of the following frequency bands can be employed during the filtering: delta band (typically from about 1 Hz to about 4 Hz), theta band (typically from about 3 to about 8 Hz), alpha band (typically from about 7 to about 13 Hz), low beta band (typically from about 12 to about 18 Hz), beta band (typically from about 17 to about 23 Hz), and high beta band (typically from about 22 to about 30 Hz). Higher frequency bands, such as, but not limited to, gamma band (typically from about 30 to about 80 Hz), are also contemplated.

Following the waveform analysis, waveform characteristics, such as, but not limited to, time (latency), frequency and optionally amplitude are preferably extracted. These waveform characteristics are preferably obtained as discrete values, thereby forming a vector whose components are the individual waveform characteristics. Use of discrete values is advantageous since it reduces the amount of data for further analysis. Other reduction techniques, such as, but not limited to, statistical normalization (e.g., by means of standard score, or by employing any statistical moment) are also contemplated. Normalization can be used for reducing noise and is also useful when the method is applied to data acquired from more than one subject and/or when the interfaces between the measuring device and the brain vary among different subjects or among different locations for a single subject. For example, statistical normalization can be useful when there is non-uniform impedance matching among EEG electrodes.

The extraction of characteristics results in a plurality of vectors, each of which includes, as the components of the vector, the spatial characteristics (e.g., the location of the respective electrode or other measuring device), and one or more non-spatial characteristics as obtained from the segmentation and decomposition. Each of these vectors is a feature of the data, and any pair of vectors whose characteristics obey some relation (for example, causal relation wherein the two vectors are consistent with flow of information from the location associated with one vector to the location associated with the other vector) constitutes two activity-related features.

The extracted vectors thus define a multidimensional space. For example, when the components include location, time and frequency, the vectors define a three-dimensional space, and when the components include location, time, frequency and amplitude, the vectors define a four-dimensional space. Higher number of dimensions is not excluded from the scope of the present invention.

When the analysis is applied to neurophysiological data of one subject, each feature of the data is represented as a point within the multidimensional space defined by the vectors, and each set of activity-related features is represented as a set of points such that any point of the set is within a specific distance along the time axis (also referred to hereinbelow as "latency-difference") from one or more other points in the set.

When the analysis is applied to neurophysiological data acquired from a group or sub-group of subjects, a feature of the data is preferably represented as a cluster of discrete points in the aforementioned multidimensional space. A cluster of points can also be defined when the analysis is applied to neurophysiological data of a single subject. In these embodiments, vectors of waveform characteristics are extracted separately for separate stimuli presented to the subject, thereby defining clusters of points within the multidimensional space, where each point within the cluster corresponds to a response to a stimulus applied at a different time. The separate stimuli optionally and preferably form a set of repetitive presentations of the same or similar stimulus, or a set of stimuli which are not necessarily identical but are of the same type (e.g., a set of not-necessarily identical visual stimuli). Use of different stimuli at different times is not excluded from the scope of the present invention.

Also contemplated are combinations of the above representations, wherein data are collected from a plurality of subjects and for one or more of the subjects, vectors of waveform characteristics are extracted separately for time-separated stimuli (i.e., stimuli applied at separate times). In these embodiments, a cluster contains points that correspond to different subjects as well as points that correspond to a response to a separated stimulus. Consider, for example, a case in which data were collected from 10 subjects, wherein each subject was presented with 5 stimuli during data acquisition. In this case, the dataset includes 5×10=50 data segment, each corresponding to a response of one subject to one stimulus. Thus, in a cluster within the multidimensional space may include up to 5×10 points, each representing a vector of characteristics extracted from one of the data segments.

Whether representing characteristics of a plurality of subjects and/or characteristics of a plurality of responses to stimuli presented to a single subject the width of a cluster along a given axis of the space describes a size of an activity window for the corresponding data characteristic (time, frequency, etc). As a representative example, consider the width of a cluster along the time axis. Such width is optionally and preferably used by the method to describe the latency range within which the event occurs across multiple subjects. Similarly, the width of a cluster along the frequency axis can be used for describing the frequency band indicating an occurrence of an event occurring across multiple subjects; the widths of a cluster along the location axes (e.g., two location axes for data corresponding to a 2D location map, and three location axes for data corresponding to a 3D location map) can be used to define a set of adjoining electrodes at which the event occurs across multiple subjects, and the width of a cluster along the amplitude axis can be used to define an amplitude range indicating an occurrence of event across multiple subjects.

For a group or sub-group of subjects, activity-related features can be identified as follows. A single cluster along the time axis is preferably identified as representing a unitary event occurring within a time window defined, as stated, by the width of the cluster. This window is optionally and preferably narrowed to exclude some outlier points, thereby redefining the latency range characterizing the respective data feature. For a succession of clusters along the time axis, wherein each cluster in the series has a width (along the time axis) within a particular constraint, a pattern extraction procedure is preferably implemented for identifying those clusters which obey connectivity relations thereamongst. Broadly speaking such procedure can search over the clusters for pairs of clusters in which there are connectivity relations between a sufficient number of points between the clusters.

The pattern extraction procedure can include any type of clustering procedures, including, without limitation, a density-based clustering procedure, a nearest-neighbor-based clustering procedure, and the like. A density-based clustering procedure suitable for the present embodiments is described in Cao et al., 2006, "Density-based clustering over an evolving data stream with noise," Proceedings of the Sixth SIAM International Conference on Data Mining Bethesda, Md., p. 328-39. A nearest-neighbor clustering procedure suitable for the present embodiments is described in [R. O. Duda, P. E. Hart and D. G. Stork, "Pattern Classification" (2nd Edition), A Wiley-Interscience Publication, 2000]. When nearest-neighbor clustering procedure is employed, clusters are identified and thereafter gathered to form meta-clusters based on spatiotemporal distances among the clusters. The meta-clusters are, therefore, clusters of the identified clusters. In these embodiments, the meta-clusters are the features of the data, and activity-related features are identified among the meta-clusters.

FIG. 3A is a flowchart diagram describing a procedure for identifying activity-related features for a group of subjects, according to some embodiments of the present invention. The procedure begins at 40 and continues to 41 at which isolated clusters are identified. The present embodiments contemplate both subspace clustering, wherein clusters are identified on a particular projection of the multidimensional space, and full-space clustering wherein clusters are identified on the entire multidimensional space. Subspace clustering is preferred from the standpoint of computation time, and full-space clustering is preferred from the standpoint of features generality.

One representative example of subspace clustering includes identification of clusters along the time axis, separately for each predetermined frequency band and each predetermined spatial location. The identification optionally and preferably features a moving time-window with a fixed and predetermined window width. A typical window width for EEG data is about 200 ms for the delta band. A restriction on a minimal number of points in a cluster is optionally applied so as not to exclude small clusters from the analysis. Typically cluster with less than X points, where X equals about 80% of the subjects in the group, are excluded. The minimal number of points can be updated during the procedure. Once an initial set of clusters is defined, the width of the time window is preferably lowered.

Another representative example of subspace clustering includes identification of clusters over a space-time subspace, preferably separately for each predetermined frequency band. In this embodiment, the extracted spatial characteristics are represented using a continuous spatial coordinate system, e.g., by piecewise interpolation between the locations of the measuring devices, as further detailed hereinabove. Thus, each cluster is associated with a time window as well as a spatial region, wherein the spatial region may or may not be centered at a location of a measuring device. In some embodiments, at least one cluster is associated with a spatial region which is centered at a location other than a location of a measuring device. The space-time subspace is typically three-dimensional with one temporal dimension and two spatial dimensions, wherein each cluster is associated with a time-window and a two-dimensional spatial region over a surface which may correspond, e.g., to the shape of the scalp surface, the epicortical surface and the like. Also contemplated is a four-dimensional space-time space wherein each cluster is associated with a time-window and a three-dimensional spatial region over a volume corresponding, at least in part, to internal brain.

Another representative example of subspace clustering includes identification of clusters over a frequency-space-time subspace. In this embodiment, instead of searching for clusters separately for each predetermined frequency band, the method allows identification of clusters also at frequencies which are not predetermined. Thus, the frequency is considered as a continuous coordinate over the subspace. As in the embodiment of space-time subspace, the extracted spatial characteristics are represented using a continuous spatial coordinate system. Thus, each cluster is associated with a time window, a spatial region and a frequency band. The spatial region can be two- or three-dimensional as further detailed hereinabove. In some embodiments, at least one cluster is associated with a spatial region which is centered at a location other than a location of a measuring device, and at least one cluster is associated with a frequency band which includes frequencies of two or more of the delta, theta, alpha, low beta, beta, high beta and gamma bands. For example, a cluster can be associated with a frequency band spanning over part of the delta band and part of the theta band, or part of the theta band and part of the alpha band, or part of the alpha band and part of the low beta band, etc.

The procedure optionally and preferably continues to 42 at which, a pair of clusters is selected. The procedure optionally and preferably continues to 43 at which, for each subject that is represented in the selected pair, latency difference (including zero difference) between the corresponding events is optionally calculated. The procedure continues to 44 at which a constraint is applied to the calculated latency differences such that latency differences which are outside a predetermined threshold range (e.g., 0-30 ms) are rejected while latency differences which are within the predetermined threshold range are accepted. The procedure continues to decision 45 at which the procedure determines whether the number of accepted differences is sufficiently large (i.e., above some number, e.g., above 80% of the subjects in the group). If the number of accepted differences is not sufficiently large the procedure proceeds to 46 at which the procedure accepts the pair of clusters and identifies it as a pair of activity-related features. If the number of accepted differences is sufficiently large the procedure proceeds to 47 at which the procedure reject the pair. From 46 or 47 the procedure of the present embodiments loops back to 42.

An illustrative example for determining relations among the data features and identification of activity-related features is shown in FIG. 3B. The illustration is provided in terms of a projection onto a two-dimensional space which includes time and location. The present example is for an embodiment in which the spatial characteristics are discrete, wherein the identification of clusters is along the time axis, separately for each predetermined frequency band and each predetermined spatial location. The skilled person would know how to adapt the description for the other dimensions, e.g., frequency, amplitude, etc. FIG. 3B illustrates a scenario in which data are collected from 6 subjects (or from a single subject, present with 6 stimuli at different times), enumerated 1 through 6. For clarity of presentation, different data segments data (e.g., data collected from different subjects, or from the same subject but for stimuli of different times) are separated along a vertical axis denoted "Data Segment No." For each segment, an open circle represents an event recorded at one particular location (by means of a measuring device, e.g., EEG electrode) denoted "A", and a solid disk represents an event recorded at another particular location denoted "B".

The time axis represents the latency of the respective event, as measured, e.g., from a time at which the subject was presented with a stimulus. The latencies of the events are denoted herein $t^{(i)}_A$ and $t^{(i)}_B$, where i represents the segment index (i=1, . . . , 6) and A and B represent the location. For clarity of presentation, the latencies are not shown in FIG. 3B, but one of ordinary skills in the art, provided with the details described herein would know how to add the latencies to the drawing.

For each of locations A and B, a time window is defined. These time windows, denoted $\Delta t_A$ and $\Delta t_B$, correspond to the width of the clusters along the time axis and they can be the same or different from one another, as desired. Also defined is a latency difference window $\Delta t_{AB}$, between the two unitary events. This window corresponds to the separation along the time axis between the clusters (e.g., between their centers). The window $\Delta t_{AB}$ is illustrated as an interval having a dashed segment and a solid segment. The length of the dashed segment represents the lower bound of the window and the overall length of the interval represents the upper bound of the window. $\Delta t_A$, $\Delta t_B$ and $\Delta t_{AB}$ are part of the criteria for determining whether to accept the pair of events recorded at A and B as activity-related features.

The time windows $\Delta t_A$ and $\Delta t_B$ are preferably used for identifying unitary events in the group. As shown, for each of segment Nos. 1, 2, 4 and 5 both events fall within the respective time windows (mathematically, this can be written as follows: $t^{(i)}_A \in \Delta t_A$, $t^{(i)}_B \in \Delta t_A$, i=1, 2, 4, 5). On the other hand, for segment No. 3 the event recorded at A falls outside $\Delta t_A$ ($t^{(3)}_A \notin \Delta t_A$) while the event recoded at B falls within $\Delta t_B$ ($t^{(3)}_B \Delta \Delta t_B$), and for segment No. 6 the event recorded at A falls within $\Delta t_A$ ($t^{(6)}_A \in \Delta t_A$) while the event recoded at B falls outside $\Delta t_B$($t^{(6)} \notin \Delta t_B$). Thus, for location A, a unitary event is defined as a cluster of data points obtained from segment Nos. 1, 2, 4, 5 and 6, and for location B, a unitary event is defined as a cluster of data points obtained from segment Nos. 1-5.

The latency difference window $\Delta t_{AB}$ is preferably used for identifying activity-related features. In various exemplary embodiments of the invention the latency difference $\Delta t^{(i)}_{AB}$ (i=1, 2, . . . , 5) of each segment is compared to the latency difference window $\Delta t_{AB}$. In various exemplary embodiments of the invention a pair of features is accepted as an activity-related pair if (i) each of the features in the pair belongs to a unitary event, and (ii) the corresponding latency difference falls within $\Delta t_{AB}$. In the illustration of FIG. 3B, each of the pairs recorded from segment Nos. 4 and 5 is accepted as a pair of activity-related features, since both criteria are met for each of those segment ($\Delta t^{(i)}_{AB} \in \Delta t_{AB}$, $t^{(i)}_{A} \in \Delta t_{A}$, $t^{(i)}_{B} \in \Delta t_{A}$, i=4, 5). The pairs recorded from segment Nos. 1-3 do not pass the latency difference criterion since each of $\Delta t^{(1)}_{AB}$, $\Delta t^{(2)}_{AB}$ and $\Delta t^{(3)}_{AB}$ is outside $\Delta t_{AB}$ ($\Delta t^{(i)}_{AB} \notin \Delta t_{AB}$, i=1, 2, 3). These pairs are, therefore, rejected. Notice that in the present embodiment, even though the pair obtained from segment No. 6 passes the latency difference criterion, the pair is rejected since it fails to pass the time-window criterion ($\Delta t^{(6)}_{AB} \notin \Delta t_{AB}$).

In various exemplary embodiments of the invention the procedure also accepts pairs corresponding to simultaneous events of the data that occur at two or more different locations. Although such events are not causal with respect to each other (since there is no flow of information between the locations), the corresponding features are marked by the method. Without being bounded to any particular theory, the present inventors consider that simultaneous events of the data are causally related to another event, although not identified by the method. For example, the same physical stimulus can generate simultaneous events in two or more locations in the brain.

The identified pairs of activity-related features, as accepted at 46, can be treated as elementary patterns which can be used as elementary building blocks for constructing complex patterns within the feature space. In various exemplary embodiments of the invention, the method proceeds to 48 at which two or more pairs of activity-related features are joined (e.g., concatenated) to form a pattern of more than two features. The criterion for the concatenation can be similarity between the characteristics of the pairs, as manifested by the vectors. For example, in some embodiments, two pairs of activity-related features are concatenated if they have a common feature. Symbolically, this can be formulated as follows: the pairs "A-B" and "B-C" have "B" as a common feature and are concatenated to form a complex pattern A-B-C.

Preferably, the concatenated set of features is subjected to a thresholding procedure, for example, when X % or more of the subjects in the group are included in the concatenated set, the set is accepted, and when less than X % of the subjects in the group are included in the concatenated set, the set is rejected. A typical value for the threshold X is about 80.

Each pattern of three or more features thus corresponds to a collection of clusters defined such that any cluster of the collection is within a specific latency-difference from one or more other clusters in the collection. Once all pairs of clusters are analyzed the procedures continues to terminator 49 at which it ends.

Referring again to FIG. 1, at 13 a brain network activity (BNA) pattern is constructed.

Figure 2:
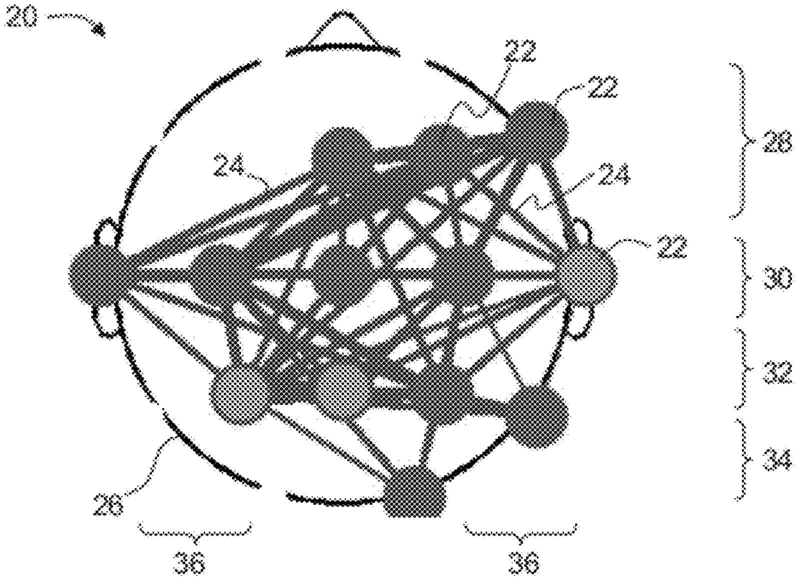

The concept of BNA pattern can be better understood with reference to FIG. 2 which is a representative example of a BNA pattern 20 which may be extracted from neurophysiological data, according to some embodiments of the present invention. BNA pattern 20 has a plurality of nodes 22, each representing one of the activity-related features. For example, a node can represent a particular frequency band (optionally two or more particular frequency bands) at a particular location and within a particular time-window or latency range, optionally with a particular range of amplitudes.

Some of nodes 22 are connected by edges 24 each representing the causal relation between the nodes at the ends of the respective edge. Thus, the BNA pattern is a represented as a graph having nodes and edges. In various exemplary embodiments of the invention the BNA pattern includes plurality of discrete nodes, wherein information pertaining to features of the data is represented only by the nodes and information pertaining to relations among the features is represented only by the edges.

FIG. 2 illustrates BNA pattern 20 within a template 26 of a scalp, allowing relating the location of the nodes to the various lobes of the brain (frontal 28, central 30, parietal 32, occipital 34 and temporal 36). The nodes in the BNA pattern can be labeled by their various characteristics. A color coding or shape coding visualization technique can also be employed, if desired. For example, nodes corresponding to a particular frequency band can be displayed using one color or shape and nodes corresponding to another frequency band can be displayed using another color or shape. In the representative example of FIG. 2, two colors are presented. Red nodes correspond to Delta waves and green nodes correspond to Theta waves.

BNA pattern 20 can describe brain activity of a single subject or a group or sub-group of subjects. A BNA pattern which describes the brain activity of a single subject is referred to herein as a subject-specific BNA pattern, and BNA pattern which describes the brain activity of a group or sub-group of subjects is referred to herein as a group BNA pattern.

When BNA pattern 20 is a subject-specific BNA pattern, only vectors extracted from data of the respective subject are used to construct the BNA pattern. Thus, each node corresponds to a point in the multidimensional space and therefore represents an activity event in the brain. When BNA pattern 20 is a group BNA pattern, some nodes can correspond to a cluster of points in the multidimensional space and therefore represents an activity event which is prevalent in the group or sub-group of subjects. Due to the statistical nature of a group BNA pattern, the number of nodes (referred to herein as the "order") and/or edges (referred to herein as the "size") in a group BNA pattern is typically, but not necessarily, larger than the order and/or size of a subject-specific BNA pattern.

As a simple example for constructing a group BNA pattern, the simplified scenario illustrated in FIG. 3B is considered, wherein a "segment" corresponds to a different subject in a group or sub-group of subjects. The group data include, in the present example, two unitary events associated with locations A and B. Each of these events forms a cluster in the multidimensional space. In various exemplary embodiments of the invention each of the clusters, referred to herein as clusters A and B, is represented by a node in the group BNA. The two clusters A and B are identified as activity-related features since there are some individual points within these clusters that pass the criteria for such relation (the pairs of Subject Nos. 4 and 5, in the present example). Thus, in various exemplary embodiments of the invention the nodes corresponding to clusters A and B are connected by an edge. A simplified illustration of the resulting group BNA pattern is illustrated in FIG. 3C.

A subject-specific BNA pattern is optionally and preferably constructed by comparing the features and relations among features of the data collected from the respective subject to the features and relations among features of reference data, which, in some embodiments of the present invention comprise group data. In these embodiments, points and relations among points associated with the subject's data are compared to clusters and relations among clusters associated with the group's data. Consider, for example, the simplified scenario illustrated in FIG. 3B, wherein a "segment" corresponds to a different subject in a group or sub-group of subjects. Cluster A does not include a contribution from Subject No. 3, and cluster B does not include a contribution from Subject No. 6, since for these subjects the respective points fail to pass the time-window criterion. Thus, in various exemplary embodiments of the invention when a subject-specific BNA pattern is constructed for Subject No. 3 it does not include a node corresponding to location A, and when a subject-specific BNA pattern is constructed for Subject No. 6 it does not include a node corresponding to location B. On the other hand, both locations A and B are represented as nodes in the subject-specific BNA patterns constructed for any of Subject Nos. 1, 2, 4 and 5.

For those subjects for which the respective points are accepted as a pair of activity-related features (Subject Nos. 4 and 5, in the present example), the corresponding nodes are preferably connected by an edge. A simplified illustration of a subject-specific BNA pattern for such a case is shown in FIG. 3D.

Note that for this simplified example of only two nodes, the subject-specific BNA of FIG. 3D is similar to the group BNA of FIG. 3C. For a larger number of nodes, the order and/or size of the group BNA pattern is, as stated, typically larger than the order and/or size of the subject-specific BNA pattern. An additional difference between the subject-specific and group BNA patterns can be manifested by the degree of relation between the activity-related features represented by the edges, as further detailed hereinbelow.

For subjects for which the respective points were rejected (Subject Nos. 1 and 2, in the present example), the corresponding nodes are preferably not connected by an edge. A simplified illustration of a subject-specific BNA pattern for such case is shown in FIG. 3E.

It is to be understood, however, that although the above technique for constructing a subject-specific BNA pattern is described in terms of the relation between the data of a particular subject to the data of a group of subjects, this need not necessarily be the case, since in some embodiments, a subject-specific BNA pattern can be constructed only from the data of a single subject. In these embodiments, vectors of waveform characteristics are extracted separately for time-separated stimuli, to define clusters of points where each point within the cluster corresponds to a response to a stimulus applied at a different time, as further detailed hereinabove. The procedure for constructing subject-specific BNA pattern in these embodiments is preferably the same as procedure for constructing a group BNA pattern described above. However, since all data are collected from a single subject, the BNA pattern is subject-specific.

Thus, the present embodiments contemplate two types of subject-specific BNA patterns: a first type that describes the association of the particular subject to a group or sub-group of subjects, which is a manifestation of a group BNA pattern for the specific subject, and a second type that describes the data of the particular subject without associating the subject to a group or sub-group of subjects. The former type of BNA pattern is referred to herein as an associated subject-specific BNA pattern, and the latter type of BNA pattern is referred to herein as an unassociated subject-specific BNA pattern.

For unassociated subject-specific BNA pattern, the analysis is preferably performed on the set of repetitive presentations of a single stimulus, namely on a set of single trials, optionally and preferably before averaging the data and turning it to one single vector of the data. For group BNA patterns, on the other hand, the data of each subject of the group is optionally and preferably averaged and thereafter turned into vectors of the data.

Note that while the unassociated subject-specific BNA pattern is generally unique for a particular subject (at the time the subject-specific BNA pattern is constructed), the same subject may be characterized by more than one associated subject-specific BNA patterns, since a subject may have different associations to different groups. Consider for example a group of healthy subjects and a group of non-healthy subjects all suffering from the same brain disorder. Consider further a subject Y which may or may not belong to one of those groups. The present embodiments contemplate several subject-specific BNA patterns for subject Y. A first BNA pattern is an unassociated subject-specific BNA pattern, which, as stated is generally unique for this subject, since it is constructed from data collected only from subject Y. A second BNA pattern is an associated subject-specific BNA pattern constructed in terms of the relation between the data of a subject Y to the data of the healthy group. A third BNA pattern is an associated subject-specific BNA pattern constructed in terms of the relation between the data of a subject Y to the data of the non-healthy group. Each of these BNA patterns are useful for assessing the condition of subject Y. The first BNA pattern can be useful, for example, for monitoring changes in the brain function of the subject over time (e.g., monitoring brain plasticity or the like) since it allows comparing the BNA pattern to a previously constructed unassociated subject-specific BNA pattern. The second and third BNA pattern can be useful for determining the level of association between subject Y and the respective group, thereby determining the likelihood of brain disorder for the subject.

Also contemplated are embodiments in which the reference data used for constructing the subject-specific BNA pattern corresponds to history data previously acquired from the same subject. These embodiments are similar to the embodiments described above regarding the associated subject-specific BNA pattern, except that the BNA pattern is associated to the history of the same subject instead of to a group of subjects.

Additionally contemplated are embodiments in which the reference data corresponds to data acquired from the same subject at some later time. These embodiments allow investigating whether data acquired at an early time evolve into the data acquired at the later time. A particular and non limiting example is the case of several treatment sessions, e.g., N sessions, for the same subject. Data acquired in the first several treatment sessions (e.g., from session 1 to session $k_1<N$) can be used as reference data for constructing a first associated subject-specific BNA pattern corresponding to mid sessions (e.g., from session $k_2>k_1$ to session $k_3>k_2$), and data acquired in the last several treatment sessions (e.g., from session $k_4$ to session N) can be used as reference data for constructing a second associated subject-specific BNA pattern corresponding to the aforementioned mid sessions, where $1<k_1<k_2<k_3<k_4$. Such two associated subject-specific BNA patterns for the same subject can be used for determining data evolution from the early stages of the treatment to the late stages of the treatment.

The method proceeds to 14 at which a connectivity weight is assigned to each pair of nodes in the BNA pattern (or, equivalently, to each edge in the BNA) pattern, thereby providing a weighted BNA pattern. The connectivity weight is represented in FIGS. 2, 3C and 3D by the thickness of the edges connecting two nodes. For example, thicker edges can correspond to higher weights and thinner edges can correspond to lower weights.

In various exemplary embodiments of the invention the connectivity weight comprises a weight index WI calculated based on at least one of the following cluster properties: (i) the number of subjects participating in the corresponding cluster pair, wherein greater weights are assigned for larger number of subjects; (ii) the difference between the number of subjects in each cluster of the pair (referred to as the "differentiation level" of the pair), wherein greater weights are assigned for lower differentiation levels; (iii) the width of the time windows associated with each of the corresponding clusters (see, e.g., $\Delta t_A$ and $\Delta t_B$ in FIG. 3A), wherein greater weights are assigned for narrower windows; (iv) the latency difference between the two clusters (see $\Delta t_{AB}$ in FIG. 3A), wherein greater weights are assigned for narrower windows; (v) the amplitude of the signal associated with the corresponding clusters; (vi) the frequency of the signal associated with the corresponding clusters; and (vii) the width of a spatial window defining the cluster (in embodiments in which the coordinate system is continuous). For any of the cluster properties, except properties (i) and (ii), one or more statistical observables of the property, such as, but not limited to, average, median, supremum, infimum and variance over the cluster are preferably used.

For a group BNA pattern or an unassociated subject-specific BNA pattern, the connectivity weight preferably equals the weight index WI as calculated based on the cluster properties.

For an associated subject-specific BNA pattern, the connectivity weight of a pair of nodes is preferably assigned based on the weight index WI as well as one or more subject-specific and pair-specific quantities denoted SI. Representative examples of such quantities are provided below.

In various exemplary embodiments of the invention a pair of nodes of the associated subject-specific BNA pattern is assigned with a connectivity weight which is calculated by combining WI with SI. For example, the connectivity weight of a pair in the associated subject-specific BNA pattern can be given by WI·SI. When more than one quantities (say N quantities) are calculated for a given pair of nodes, the pair can be assigned with more than one connectivity weights, e.g., $WI \cdot SI_1, WI \cdot SI_2, \ldots, WI \cdot SI_N$, wherein $SI_1, SI_2, \ldots, SI_N$, are N calculated quantities. Alternatively or additionally, all connectivity weights of a given pair can be combined, e.g., by averaging, multiplying and the like.

The quantity SI can be, for example, a statistical score characterizing the relation between the subject-specific pair and the corresponding clusters. The statistical score can be of any type, including, without limitation, deviation from average, absolute deviation, standard-score and the like. The relation for whom the statistical score is calculated can pertain to one or more properties used for calculating the weight index WI, including, without limitation, latency, latency difference, amplitude, frequency and the like.

A statistical score pertaining to latency or latency difference is referred to herein as a synchronization score and denoted SIs. Thus, a synchronization score according to some embodiments of the present invention can be obtained by calculating a statistical score for (i) the latency of the point as obtained for the subject (e.g., $t^{(i)}_A$ and $t^{(i)}_B$, in the above example) relative to the group-average latency of the corresponding cluster, and/or (ii) the latency difference between two points as obtained for the subject (e.g., $\Delta t^{(i)}_{AB}$), relative to the group-average latency difference between the two corresponding clusters.

A statistical score pertaining to amplitude is referred to herein as an amplitude score and denoted SIa. Thus an amplitude score according to some embodiments of the present invention is obtained by calculating a statistical score for the amplitude as obtained for the subject relative to the group-average amplitude of the corresponding cluster.

A statistical score pertaining to frequency is referred to herein as a frequency score and denoted SIf. Thus a frequency score according to some embodiments of the present invention is obtained by calculating a statistical score for the frequency as obtained for the subject relative to the group-average frequency of the corresponding cluster.

A statistical score pertaining to the location is referred to herein as a location score and denoted SIl. These embodiments are particularly useful in embodiments in which a continuous coordinate system is employed, as further detailed hereinabove. Thus a location score according to some embodiments of the present invention is obtained by calculating a statistical score for the location as obtained for the subject relative to the group-average location of the corresponding cluster.

Calculation of statistical scores pertaining to other properties is not excluded from the scope of the present invention.

Following is a description of a technique for calculating the quantity SI, according to some embodiments of the present invention.

When SI is a synchronization score SIs the calculation is optionally and preferably based on the discrete time points matching the spatiotemporal constraints set by the electrode pair ($Time_{subj}$), if such exist. In these embodiments, the times of these points can are compared to the mean and standard deviation of the times of the discrete points participating in the group pattern ($Time_{pat}$), for each region to provide a regional synchronization score $SIs_r$. The synchronization score S is can then be calculated, for example, by averaging the regional synchronization scores of the two regions in the pair. Formally, this procedure can be written as:

$$SIs_r = 0.5 + \frac{std(Time_{pat})}{2*(\text{abs}(\overline{Time_{pat}} - Time_{subj}) + std(Time_{pat}))};$$

$$SIs = \frac{1}{r}\sum SIs_r$$

An amplitude score SIa, is optionally and preferably calculated in a similar manner. Initially the amplitude of the discrete points of the individual subject ($Amp_{subj}$) is compared to the mean and standard deviation of the amplitudes of the discrete points participating in the group pattern ($Amp_{pat}$), for each region to provide a regional amplitude score $SIa_r$. The amplitude score can then be calculated, for example, by averaging the regional amplitude scores of the two regions in the pair:

$$SIa_r = 0.5 + \frac{std(Amp_{pat})}{2*(\text{abs}(\overline{Amp_{pat}} - Amp_{subj}) + std(Amp_{pat}))};$$

-continued $$SIa = \frac{1}{r}\sum SIa_r$$

One or more BNA pattern similarities S can then be calculated as a weighted average over the nodes of the BNA pattern, as follows:

$$Ss = \frac{\sum_i (W_i * SIs_i)}{\sum_i W_i}$$

$$Sa = \frac{\sum_i (W_i * SIa_i)}{\sum_i W_i}$$

$$Sf = \frac{\sum_i (W_i * SIf_i)}{\sum_i W_i}$$

$$Sl = \frac{\sum_i (W_i * SIl_i)}{\sum_i W_i}$$

Formally, an additional similarity, Sc, can be calculated, as follows:

$$Ic = \frac{\sum_i (W_i * SIc_i)}{\sum_i W_i},$$

where $SIC_i$ is a binary quantity which equals 1 if pair i exists in the subject's data and 0 otherwise.

In some embodiments of the present invention the quantity SI comprises a correlation value between recorded activities. In some embodiments, the correlation value describes correlation between the activities recorded for the specific subject at the two locations associated with the pair, and in some embodiments the correlation value describes correlation between the activities recorded for the specific subject at any of the locations associated with the pair and the group activities as recorded at the same location. In some embodiments, the correlation value describes causality relations between activities.

Procedures for calculating correlation values, such as causality relations, are known in the art. In some embodiments of the present invention the Granger theory is employed [Granger C W J, 1969, "Investigating Causal Relations By Econometric Models And Cross-Spectral Methods," Econometrica, 37(3):242]. Other techniques suitable for the present embodiments are found in Durka et al., 2001, "Time-frequency microstructure of event-related electroencephalogram desynchronisation and synchronisation," Medical & Biological Engineering & Computing, 39:315; Smith Bassett et al., 2006, "Small-World Brain Networks" Neuroscientist, 12:512; He et al., 2007, "Small-World Anatomical Networks in the Human Brain Revealed by Cortical Thickness from MRI," Cerebral Cortex 17:2407; and De Vico Fallani et al., "Extracting Information from Cortical Connectivity Patterns Estimated from High Resolution EEG Recordings: A Theoretical Graph Approach," Brain Topogr 19:125; the contents of all of which are hereby incorporated by reference.

The connectivity weights assigned over the BNA pattern can be calculated as a continuous variable (e.g., using a function having a continuous range), or as a discrete variable (e.g., using a function having a discrete range or using a lookup table). In any case, connectivity weights can have more than two possible values. Thus, according to various exemplary embodiments of the present invention the weighted BNA pattern has at least three, or at least four, or at least five, or at least six edges, each of which being assigned with a different connectivity weight.

Once the BNA pattern is constructed it can be transmitted to a display device such as a computer monitor, or a printer. Alternatively or additionally, the BNA pattern can be transmitted to a computer-readable medium.

The method ends at 15.

FIG. 4 is a flowchart diagram describing a method suitable for analyzing a subject-specific BNA pattern, according to various exemplary embodiments of the present invention. The method begins at 50 and continues to 51 at which a BNA pattern, more preferably a weighted BNA pattern, of the subject is obtained, for example, by following the operations described above with reference to FIGS. 1, 2 and 3. The BNA pattern obtained at 51 is referred to below as BNA pattern 20. BNA pattern 20 can be displayed on a display device such as a computer monitor, printed, and/or stored in a computer-readable medium, as desired.

In various exemplary embodiments of the invention BNA pattern 20 is an associated subject-specific BNA pattern, constructed based on relations between the data of the subject to group data represented by a previously annotated BNA pattern. The previously annotated BNA pattern can optionally and preferably be an entry in a database of previously annotated BNA patterns, in which case the method preferably obtains an associated subject-specific BNA pattern for each BNA pattern of the database.

The term "annotated BNA pattern" refers to a BNA pattern which is associated with annotation information. The annotation information can be stored separately from the BNA pattern (e.g., in a separate file on a computer readable medium). The annotation information is preferably global annotation wherein the entire BNA pattern is identified as corresponding to a specific brain related disorder or condition. Thus, for example, the annotation information can pertain to the presence, absence or level of the specific disorder or condition. Also contemplated are embodiments in which the annotation information pertains to a specific brain related disorder or condition in relation to a treatment applied to the subject. For example, a BNA pattern can be annotated as corresponding to a treated brain related disorder. Such BNA pattern can also be annotated with the characteristics of the treatment, including dosage, duration, and elapsed time following the treatment. A BNA pattern can optionally and preferably be annotated as corresponding to an untreated brain related disorder.

As used herein, the term "treatment" includes abrogating, substantially inhibiting, slowing or reversing the progression of a condition, substantially ameliorating clinical or aesthetical symptoms of a condition or substantially preventing the appearance of clinical or aesthetical symptoms of a condition. Treatment can include any type of intervention, both invasive and noninvasive, including, without limitation, pharmacological, surgical, irradiative, rehabilitative, and the like.

Alternatively or additionally, the BNA pattern can be identified as corresponding to a specific group of individuals (e.g., a specific gender, ethnic origin, age group, etc.), wherein the annotation information pertains to the characteristics of this group of individuals. In some embodiments of the present invention the annotation information includes local annotation wherein nodes at several locations over the BNA pattern are identified as indicative of specific disorder, condition and/or group.

The method proceeds to 52 at which BNA pattern 20 is compared to the previously annotated BNA pattern. In embodiments in which several subject-specific BNA patterns are obtained for the same subject, each of the subject-specific BNA patterns are preferably compared to the corresponding annotated BNA pattern. The method optionally and preferably selects the pair of BNA patterns which best match each other. Optionally, the method can assign a score to each pair of BNA patterns being compared. Such score can be, for example, one or more BNA pattern similarity S, as further detailed hereinabove. Thus, in various exemplary embodiments of the invention 52 includes calculation of at least one BNA pattern similarity S, describing the similarity between BNA pattern 20 and the previously annotated BNA pattern.

In various exemplary embodiments of the invention BNA pattern 20 is compared to at least one BNA pattern annotated as abnormal, and at least one BNA pattern annotated as normal. A BNA pattern annotated as abnormal is a BNA pattern which is associated with annotation information pertaining to the presence, absence or level of a to brain related disorder or condition. A BNA pattern annotated as normal is a BNA pattern which was extracted from a subject, or more preferably, a group of subjects, identified as having normal brain function. Comparison to a BNA pattern annotated as abnormal and a BNA pattern annotated as normal is useful for classifying BNA pattern 20 according to the respective brain related disorder or condition. Such classification is optionally and preferably provided by means of likelihood values expressed using similarities between a subject-specific BNA pattern and a group BNA pattern.

Representative examples of brain related disorder or conditions to which a subject-specific BNA pattern can be classified according to the present embodiments include, without limitation, attention deficit hyperactivity disorder (ADHD), stroke, traumatic brain injury, posttraumatic stress disorder (PTSD), pain, epilepsy, Parkinson, multiple sclerosis, agitation, abuse, Alzheimer's disease/dementia, anxiety, panic, phobic disorder, bipolar disorder, borderline personality disorder, behavior control problems, body dysmorphic disorder, cognitive problems (e.g., mild cognitive impairment), depression, dissociative disorders, eating disorder, appetite disorder, fatigue, hiccups, impulse-control problems, irritability, mood problems, movement problems, obsessive-compulsive disorder, personality disorders, schizophrenia and other psychotic disorders, seasonal affective disorder, sexual disorders, sleep disorders, stuttering, substance abuse, Tourette's Syndrome, Trichotillomania, or violent/self-destructive behaviors.

The previously annotated BNA pattern can optionally and preferably be a baseline annotated BNA pattern characterizing a group of subjects identified as having normal brain function or having the same brain disorder. Such baseline annotated BNA pattern is optionally larger than BNA pattern 20 in terms of the order (namely the number of nodes in the BNA pattern) and/or size of (namely the number of edges in the BNA pattern). Representative examples of baseline BNA patterns and techniques for constructing and annotating such baseline BNA patterns are described in the Examples section that follows.

The comparison between BNA patterns, according to some embodiments of the present invention is preferably quantitative. In these embodiments the comparison between the BNA patterns comprises calculating BNA pattern similarity. The BNA pattern similarity is optionally and preferably calculated based on the values of the connectivity weights of the BNA patterns. For example, BNA pattern similarity can be obtained by averaging the connectivity weights over the subject-specific BNA pattern. When more than one type of connectivity weight is assigned for each pair of nodes in BNA pattern 20, the averaging is preferably performed over the BNA pattern separately for each type of connectivity weight. Optionally and preferably one or more of the averages can be combined (e.g., summed, multiplied, averaged, etc.) to provide a combined BNA pattern similarity. Alternatively, a representative of the averages (e.g., the largest) can be defined as the BNA pattern similarity.

The BNA pattern similarity can be used as a classification score which describes, quantitatively, the membership level of the subject to the respective group. This embodiment is particularly useful when more than one subject-specific BNA patterns are constructed for the same subject using different group data, wherein the classification score can be used to assess the membership level of the subject to each of the groups.

The similarity can be expressed as a continuous or discrete variable. In various exemplary embodiments of the invention the similarity is a non-binary number. In other words, rather than determining whether the two BNA patterns are similar or dissimilar, the method calculates the degree by which the two BNA patterns are similar or dissimilar. For example, the similarity can be expressed as percentage, as a non-integer number between 0 and 1 (e.g., 0 corresponding to complete dissimilarity and 1 corresponding to comparison between a BNA pattern and itself), and the like.

The above procedure for calculating the similarity can be performed both for the comparison between the subject-specific BNA pattern 20 and a BNA pattern annotated as abnormal, and for the comparison between the subject-specific BNA pattern 20 and a BNA pattern annotated as normal.

At 53 the method extracts information pertaining to the condition of the subject, responsively to the comparison between BNA pattern 20 and the annotated BNA pattern(s). Once the information is extracted, it can be transmitted to a computer-readable medium or a display device or a printing device, as desired. Many types of information are contemplated by the present inventors. Representative examples of such types are further detailed hereinbelow.

The method ends at 54.

In various exemplary embodiments of the invention, the extracted information pertains to the likelihood of abnormal brain function for the subject. Additionally, the BNA pattern comparison can optionally and preferably be used for extracting prognostic information. For example, BNA pattern 20 can be compared to a baseline annotated BNA pattern that characterizes a group of subject all suffering from the same abnormal brain function with similar rehabilitation history, wherein the baseline annotated BNA pattern is constructed from neurophysiological data acquired at the beginning of the rehabilitation process. The similarity level between BNA pattern 20 and that baseline annotated BNA pattern can be used as a prognosis indicator for the particular abnormal brain function and the particular rehabilitation process.

The likelihood of abnormal brain function is optionally and preferably extracted by determining a brain-disorder index based, at least in part, on the similarity between BNA pattern 20 and the annotated BNA pattern(s). For example, when a similarity between BNA pattern 20 and a BNA pattern annotated as corresponding to ADHD is calculated, the similarity can be used for calculating an ADHD index. The brain-disorder index can be the similarity itself or it can be calculated based on the similarity. In various exemplary embodiments of the invention the brain-disorder index is calculated based on the similarity between BNA pattern 20 and a BNA pattern annotated as abnormal, as well as the similarity between BNA pattern 20 and a BNA pattern annotated as normal. For example, denoting the former similarity by $S_{abnormal}$ and the latter similarity by $S_{normal}$, where both $S_{abnormal}$ and $S_{normal}$ are between 0 and 1, the brain-disorder index $I_{disorder}$ can be calculated as:

$$I_{disorder}=(S_{abnormal}+(1-S_{normal}))/2.$$

Variations of the above formula are not excluded from the scope of the present invention.

A representative example for a process for determining a brain-disorder index for the case of an ADHD is illustrated in FIGS. 5A-F, showing BNA patterns constructed from EEG data. In FIGS. 5A-F, red nodes correspond to ERP at the Delta frequency band, green nodes correspond to ERP at the Theta frequency band, and yellow nodes correspond to ERP at the Alpha frequency band. The BNA patterns also include nodes corresponding to locations where ERPs at more than one frequency band have been recorded. These nodes are shown as mixed colors. Specifically, green-red nodes correspond to ERP at the Delta and Theta frequency bands, and yellow-green nodes correspond to ERP at the Alpha and Theta frequency bands.

Figure 5A:
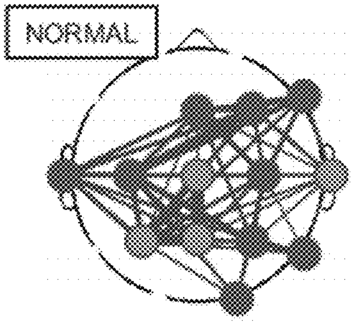
Figure 5B:
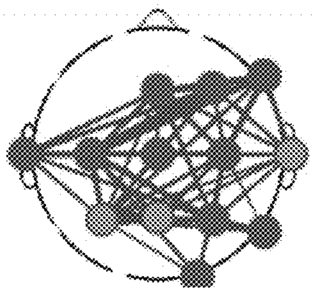
Figure 5C:
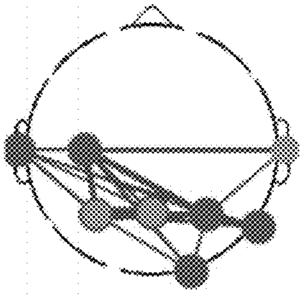
Figure 5D:
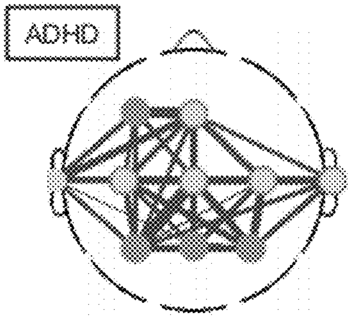

FIG. 5A shows a baseline BNA pattern annotated as normal, and FIG. 5D shows a baseline BNA pattern annotated as corresponding to ADHD. Each of these two BNA patterns was constructed from a group of adult subject identified as normal and having ADHD, respectively. As shown in FIG. 5A the baseline BNA pattern for normal brain function has nodes that represent ERPs, predominantly at the delta frequency band (red nodes), at a plurality of frontal-posterior locations at the right hemisphere. The characteristic time window of the delta nodes has a width of about 50 ms. The characteristic latencies of the delta nodes are, on the average, about 90-110 ms and about 270-330 ms. As shown in FIG. 5D the baseline BNA pattern for ADHD has nodes that represent ERPs, predominantly at the theta and alpha frequency bands (green and yellow nodes), at a plurality of frontocentral locations. The BNA pattern for ADHD may also include nodes in the central-parietal locations. The characteristic time window $\Delta t_A$ of the theta and alpha nodes is from about 100 ms to about 200 ms.

Figure 5E:
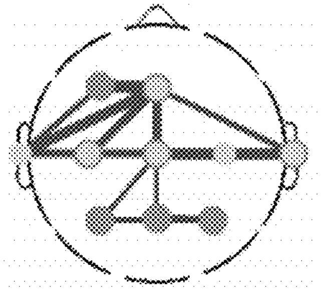

FIGS. 5B and 5E show associated subject-specific BNA patterns constructed based on comparison to the normal and ADHD baseline group BNA patterns, respectively. The similarity values, calculated as described above, are $S_{normal}$=0.76 (FIG. 5B) and $S_{ADHD}$=0.47 (FIG. 5E). Thus the BNA pattern of this subject is more similar to the normal baseline BNA pattern than to the ADHD baseline BNA pattern. The ADHD index of this subject can be set to 0.47, or, more preferably, (0.47+(1−0.76))/2=0.355.

Figure 5F:
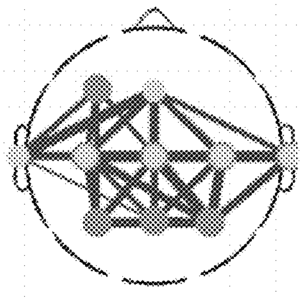

FIGS. 5C and 5F show the results of a comparison between a subject-specific BNA pattern (constructed for another single subject) to the normal and ADHD baseline BNA patterns, respectively. The similarity values, calculated as described above, are $S_{normal}$=0.32 (FIG. 5C) and $S_{ADHD}$=0.68 (FIG. 5F). Thus the BNA pattern of this subject is more similar to the ADHD baseline BNA pattern than to the normal baseline BNA pattern, and the ADHD index of this subject can be set to 0.68, or, more preferably, (0.68+(1−0.32))/2=0.68.

The brain-disorder index can be presented to the user graphically on a scale-bar. A representative example of such graphical presentation for the case of ADHD is shown in FIG. 38.

While the embodiments above were described with a particular emphasis to ADHD, it is to be understood that more detailed reference to this disorder is not to be interpreted as limiting the scope of the invention in any way. Thus, the BNA pattern comparison technique can be used for assessing likelihood of many brain related disorders, including any of the aforementioned brain related disorders. Further examples regarding the assessment of likelihood of brain related disorders are provided in the Examples section that follows (see Example 1 for ADHD and Example 5 for Mild Cognitive Impairment and Alzheimer's Disease).

A baseline annotated BNA pattern can also be associated with annotation information pertaining to a specific brain related disorder or condition of a group of subjects in relation to a treatment applied to the subjects in the group. Such baseline BNA pattern can also be annotated with the characteristics of the treatment, including dosage, duration, and elapsed time following the treatment. A comparison of BNA pattern 20 to such type of baseline BNA patterns, can provide information regarding the responsiveness of the subject to treatment and/or the efficiency of the treatment for that particular subject. Such comparison can optionally and preferably be used for extracting prognostic information in connection to the specific treatment. A BNA pattern that is complementary to such baseline BNA pattern is a BNA pattern that is annotated as corresponding to an untreated brain related disorder.

Optionally and preferably, the method compares BNA pattern 20 to at least one baseline BNA pattern annotated as corresponding to a treated brain related disorder, and at least one baseline BNA pattern annotated as corresponding to an untreated brain related disorder. Representative examples for a process for assessing the responsiveness of a subject to treatment using such two baseline BNA patterns is illustrated in FIGS. 6A-F, 7A-D and 8A-E.

Figure 6A:
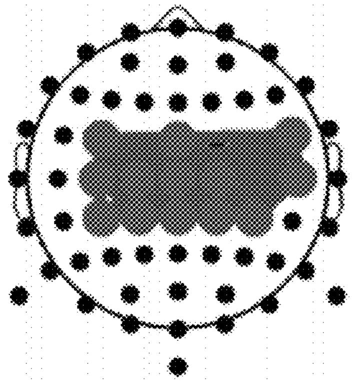
Figure 6B:
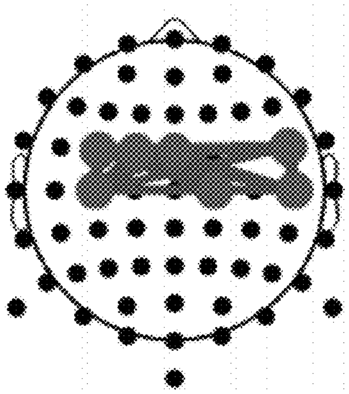
Figure 6C:
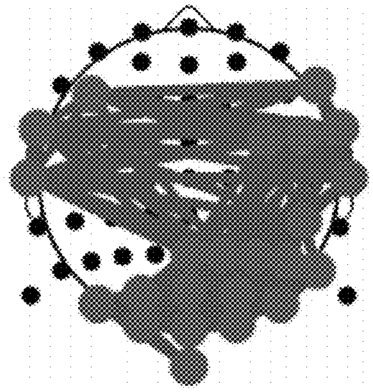
Figure 6D:
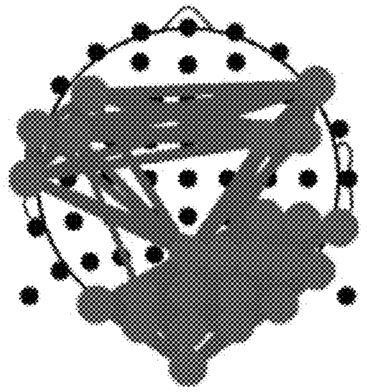

The BNA patterns shown in FIGS. 6A-D are associated subject-specific BNA patterns constructed from EEG data recorded from a particular ADHD subject. The black dots in FIGS. 6A-D show the locations of the EEG electrodes. The color codes in these BNA patterns are the same as defined above. The subject-specific BNA patterns shown in FIGS. 6A-B describe the association of the ADHD subject to a group of untreated ADHD subjects, and the BNA patterns shown in FIGS. 6C-D describe the association of the ADHD subject to a group of ADHD subjects all treated with methylphenidate (MPH). The subject-specific BNA patterns shown in FIGS. 6A and 6C are based on EEG data recorded from the ADHD subject before any treatment, and subject-specific BNA patterns shown in FIGS. 6B and 6D are based on EEG data recorded from the ADHD subject following a treatment with MPH.

Figure 6E:
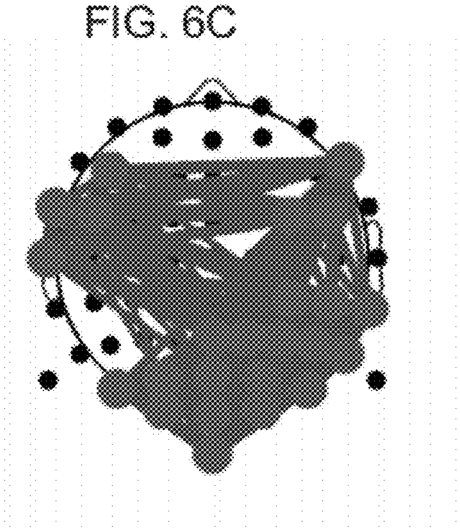
Figure 6F:
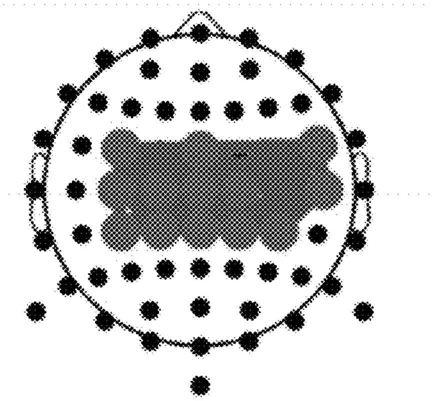

The baseline annotated BNA pattern constructed from the group of untreated ADHD subjects, and the baseline annotated BNA pattern constructed from the same group of subjects, but following treatment with MPH are shown in FIGS. 6E and 6F, respectively.

A BNA pattern similarity was calculated for each of the subject-specific BNA patterns shown in FIGS. 6A-D. The calculated similarity corresponding to the BNA pattern of FIG. 6A is 0.73, the calculated similarity corresponding to the BNA pattern of FIG. 6B is 0.19, the calculated similarity corresponding to the BNA pattern of FIG. 6C is 0.56, and the calculated similarity corresponding to the BNA pattern of FIG. 6D is 0.6. It is recognized by the present inventors that these similarity values indicate that the subject is responsive to the treatment. Before treatment, the subject's BNA pattern had a relatively high similarity (0.73) to the baseline BNA pattern for the group of untreated ADHD subjects and a relatively low similarity (0.56) to the baseline BNA pattern for the group of treated ADHD subjects, meaning that this subject can be classified with that the group of untreated ADHD subjects. Following a single dose treatment with MPH, the similarity value to the baseline BNA pattern for untreated ADHD group was scientifically reduced from 0.73 to 0.19, while the similarity value to the baseline BNA pattern for the treated ADHD group was increased from 0.56 to 0.6, meaning that after treatment a single dose, the subject's brain activity no longer has the characteristics of untreated ADHD activity, but rather has the characteristics of treated ADHD activity.

Some results of the MPH study for ADHD subjects are summarized in FIG. 39. For each subject, two associated subject-specific BNA patterns were constructed. A first BNA pattern described the association of the subject to a group of untreated ADHD subjects, and a second BNA pattern described the association of the subject to a group of healthy subjects (control). The left bar shows average score for subjects before treatment with MPH, the middle bar shows average score for subjects after treatment with MPH, and the rightmost bar shows the score of the control group.

A representative example of the evolution of the group BNA patterns over time is shown in FIG. 40. Shown in FIG. 40 are three columns of BNA patterns, corresponding to the groups of untreated ADHD subjects (left column), ADHD subjects following treatment with MPH (middle column), and control (right column). The evolution is shown at intervals of 50 ms. The topmost BNA pattern at each column is formed by a superposition of the other patterns in that column.

Further details regarding analysis of neurophysiological data acquired from ADHD subjects are provided in the Examples section that follows (see Example 1).

The BNA pattern technique of the present embodiments can also be used for determining a recommended dose for the subject. Specifically, the dose can be varied until a sufficiently high or maximal similarity to the baseline BNA pattern for treated subjects is obtained. Once such similarity is achieved, the method can determine that the dose achieving such similarity is the recommended dose for this subject.

Figure 7A:
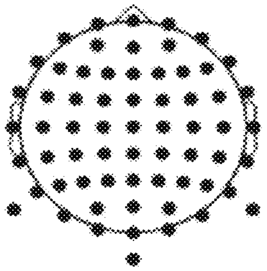
Figure 7B:
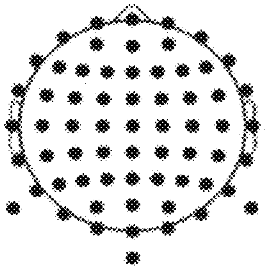
Figure 7C:
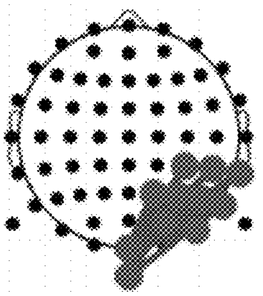
Figure 7D:
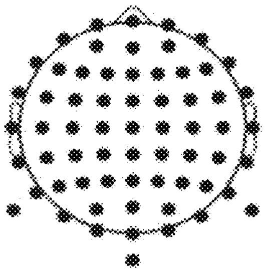

The BNA patterns shown in FIGS. 7A-D were constructed from EEG data recorded from a different ADHD subject, which was also treated with MPH according to the same protocol as described above with respect to the responder subject of FIGS. 6A-D. The black dots in FIGS. 7A-D show the locations of the EEG electrodes, and the color codes in these BNA patterns is the same as defined above. Thus, the subject-specific BNA patterns shown in FIGS. 7A-B describe the association of the ADHD subject to a group of untreated ADHD subjects, and the BNA patterns shown in FIGS. 7C-D describe the association of the ADHD subject to a group of ADHD subjects all treated with methylphenidate (MPH). The subject-specific BNA patterns shown in FIGS. 7A and 7C are based on EEG data recorded from the ADHD subject before any treatment, and subject-specific BNA patterns shown in FIGS. 7B and 7D are based on EEG data recorded from the ADHD subject following a treatment with MPH.

Note that the BNA patterns of FIGS. 7A and 7D do not include any nodes and edges. This, however, does not mean that the subjects had no brain activity. A void associated subject-specific BNA pattern means that none of data features of the respective subject was member of a cluster in the group to which the subject is attempted to be associated with.

A BNA pattern similarity was calculated for each of the subject-specific BNA patterns shown in FIGS. 7A-D. The calculated similarity corresponding to the BNA pattern of FIG. 7A is 0, the calculated similarity corresponding to the BNA pattern of FIG. 7B is 0, the calculated similarity corresponding to the BNA pattern of FIG. 7C is 0.06, and the calculated similarity corresponding to the BNA pattern of FIG. 7D is 0. It is recognized by the present inventors that these similarity values indicate that the subject is not responsive to the treatment.

FIGS. 8A-D show associated subject-specific BNA patterns constructed from EEG data recorded from two healthy volunteer subjects. The black dots in FIGS. 8A-D show the locations of the EEG electrodes, and the color codes in these BNA patterns are the same as defined above. The subject-specific BNA patterns shown in FIGS. 8A-D describe the association of the subjects to a group of healthy subjects following treatment with a placebo drug and while performing an attention task related oddball task. The baseline annotated BNA pattern of this group is shown in FIG. 8E.

Figure 8A:
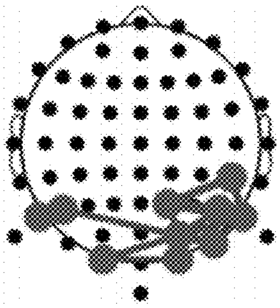
Figure 8B:
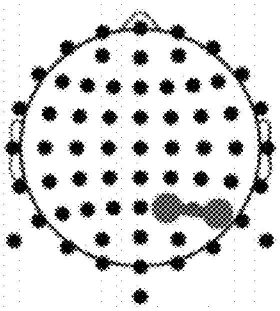
Figure 8C:
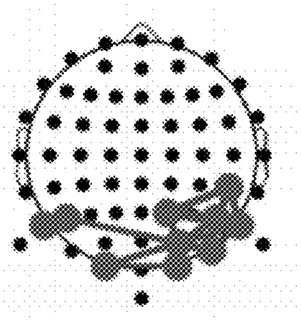
Figure 8D:
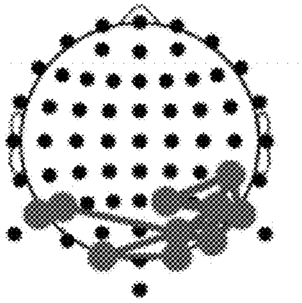
Figure 8E:
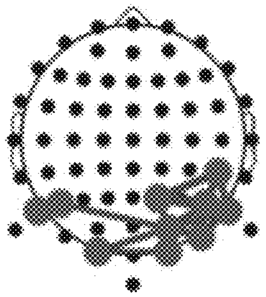

FIGS. 8A and 8C are subject-specific BNA patterns constructed from EEG data collected from a first subject (FIG. 8A) and a second subject (FIG. 8C) following treatment with a placebo, and FIGS. 8B and 8D are subject-specific BNA patterns constructed from EEG data collected from the first subject (FIG. 8B) and the second subject (FIG. 8D) following treatment with a scopolamine drug. Scopolamine is an anticholinergic drug with inhibitory effect on M2-cholinergic receptors of excited type. It has an inhibitory effect on the cerebral cortex, typically inducing slight-anesthetic effect.

A BNA pattern similarity was calculated for each of the subject-specific BNA patterns shown in FIGS. 8A-D. The calculated similarities are 0.937, 0.079, 1.0 and 0.94, respectively. It is recognized by the present inventors that these similarity values indicate that the responsivity to scopolamine is high for the first subject (FIGS. 8A and 8B) and low for the second subject (FIGS. 8C and 8D). These conclusions were also confirmed in clinical observations wherein, following treatment with the scopolamine, a 70% decrease in behavioral endpoint was observed for the first subject, but no change in behavioral endpoint was observed for the second subject.

Further details regarding analysis of neurophysiological data acquired from subjects administered with scopolamine are provided in the Examples section that follows (see Example 4).

The above examples demonstrate that the BNA pattern comparison technique of the present embodiments can be used for quantitative assessment of the responsivity to treatment. While the embodiments above were described with a particular emphasis to treatments with MPH and scopolamine, it is to be understood that more detailed reference to these treatments is not to be interpreted as limiting the scope of the invention in any way. Thus, the BNA pattern comparison technique can be used for assessing responsiveness to and efficacy of many types of treatments.

In various exemplary embodiments of the invention, the extracted information pertains to the level of pain the subject is experiencing. Preferably, the information includes an objective pain level. Pain level assessment according to some embodiments of the present invention is particularly useful in institutions that provide treatment or rehabilitation for subjects suffering from chronic pain. A representative example for the use of BNA pattern for measuring pain is illustrated in FIGS. 9A and 9B, showing BNA patterns constructed from EEG data during a pain study which is further detailed in the Examples sections that follows (see Example 3). FIG. 9A is a subject-specific BNA pattern constructed from a subject who declared that the pain was relatively high, and FIG. 9B is a subject-specific BNA pattern constructed from a subject who declared that the pain was relatively low. As shown, the difference in pain level is expressed in the BNA patterns, wherein for subjects experiencing low pain the size of the BNA pattern is smaller than for subjects experiencing high pain. Thus, the size of the BNA pattern can be used as an indicator for the level of pain.

In some embodiments of the present invention BNA pattern 20 is compared to a BNA pattern constructed for the same subjects at a different time. These embodiments are useful for many applications.

For example, in some embodiments, the comparison is used for determining presence, absence and/or level of neural plasticity in the brain.

Brain plasticity relates to the ability of the brain to adapt (functionally and/or structurally) to changed conditions, sometimes after injury or strokes, but more commonly in acquiring new skills. Brain plasticity has been demonstrated in many basic tasks, with evidence pointing to physical modifications in the cortex during repetitive performance. The plasticity of neural interactions resulting from repetitive performance of specific tasks is known to lead to improved performance.

Determination of neural plasticity is particularly useful for subjects suffering a stroke, wherein part of the brain is damaged and other parts begin to function or change their function. A comparison between two BNA's of a subject after a stroke can be used to identify a change in brain activity hence also to assess neural plasticity in the brain. In some embodiments of the present invention a late stage BNA pattern is constructed for a subject during the subject's rehabilitation. A late stage BNA pattern is optionally from data acquired during several rehabilitation sessions, preferably at a sufficiently advanced stage of the rehabilitation. Such BNA pattern can be viewed as a neural network pathway achieved by the brain in order to overcome motor dysfunction. A subject-specific BNA pattern, constructed during an individual session can then be compared to the late stage BNA pattern, thereby establishing a learning curve for the subject.

Determination of neural plasticity is particularly useful for subjects suffering from chronic pain. It is recognized by the present inventors that, the presence of chronic pain is perceived and established in the brain, and is oftentimes accompanied by chemical changes in the brain. For example, there is a decrease in N-acetyl aspartate and changes in other brain metabolites. The chemical changes result in depression, anxiety and/or a loss of cognitive memory functions. A comparison between two BNA's of the subject can be used to identify a change in brain activity hence also to assess those chemical changes. Such assessment can be used, for example, in combination with a pain stimulus, to determine the likelihood that the subject is a chronic pain sufferer or having normal response to the pain stimulus.

In some embodiments, a BNA pattern constructed from neurophysiological data acquired following a treatment is compared to a BNA pattern constructed from neurophysiological data acquired before a treatment. Such comparison can be used for assessing responsiveness to and optionally efficacy of the treatment. This can be done generally as described above with respect to FIGS. 6A-D, 7A-D and 8A-D, except that the comparisons are between two BNA patterns of the same subject instead of between a BNA pattern of the subject and a baseline BNA pattern of a group.

In some embodiments, a BNA pattern constructed from neurophysiological data acquired while the subject performs a particular task is compared to a BNA pattern constructed from neurophysiological data acquired while the subject is not performing the particular task and/or while the subject performs another particular task. A representative example for these embodiments will now be described with reference to FIGS. 10A-H.

FIGS. 10A-H show group BNA patterns constructed from EEG data recorded from two groups of subjects during a working memory test. The black dots in FIGS. 10A-H show the locations of the EEG electrodes, and the color codes in these BNA patterns is the same as defined above. During the test, each subject of the group was asked to memorize an image of a human face (referred to as the "cue"). Two seconds later, the subject was again presented with an image of a human face (referred to as the "probe") and was asked to determine whether the probe matches the cue.

Figure 10A:
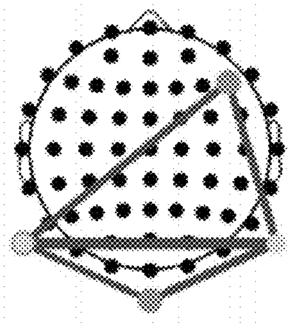
Figure 10B:
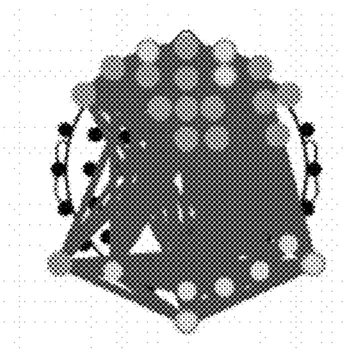
Figure 10C:
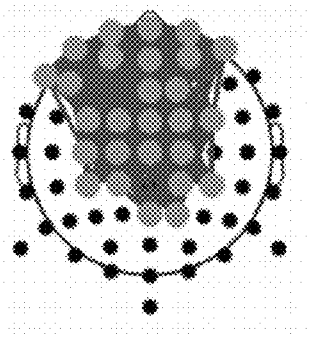
Figure 10D:
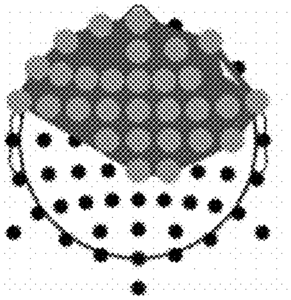
Figure 10E:
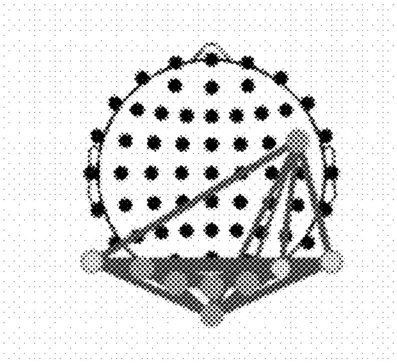
Figure 10F:
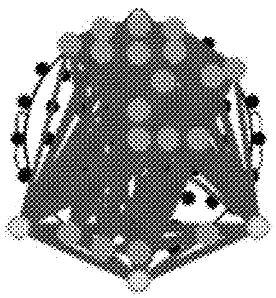
Figure 10G:
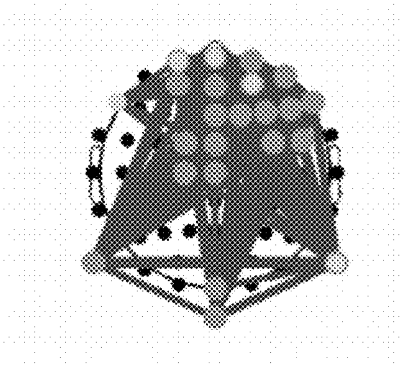
Figure 10H:
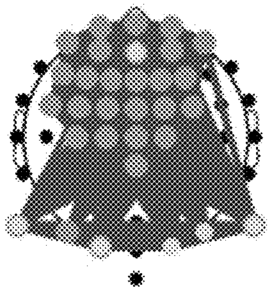

The BNA patterns of the first group are shown in FIGS. 10A-D. FIGS. 10A and 10B are group BNA patterns constructed following treatment with a placebo (referred to below as placebo A), and FIGS. 10C and 10D are group BNA patterns constructed following treatment with a Scopolamine. The BNA patterns of the second group are shown in FIGS. 10E-H, where FIGS. 10E and 10F are group BNA patterns constructed following treatment with a placebo (referred to below as placebo B), and FIGS. 10G and 10H are BNA patterns constructed following treatment with a Ketamine.

The effect of scopolamine is explained above. Ketamine is widely recognized as a general nonbarbiturate anesthetic that acts quickly to produce an anesthetic state. More specifically, ketamine is an acrylcycloalkylamine used traditionally in the induction of dissociative anesthesia. Ketamine has been used to induce anesthesia prior to elective surgery in healthy children, and also to induce anesthesia in elderly subjects who could not tolerate general anesthesia.

The BNA pattern of FIGS. 10A, 10C, 10E and 10G were constructed from the data acquired during the time at which the cue was presented and are recognized by the present inventor as containing information pertaining to the memorization process in the brain (also known in the literature as "encoding"). The BNA patterns of FIGS. 10B, 10D, 10F and 10H were constructed from the data acquired during the time at which the probe was presented, and are recognized by the present inventor as containing information pertaining to the retrieval process in the brain. It is noted that the BNA patterns of FIGS. 10A-H describe differentiating activity networks. Thus, for example, the BNA pattern of FIG. 10A describes the brain activity during cue that most differentiated between placebo A and Scopolamine, and the BNA pattern of FIG. 10B describes the brain activity during cue that most differentiated between placebo B and Ketamine.

As shown in FIGS. 10A-B and 10E-F, following treatment with placebo, the BNA pattern during retrieval is substantially larger in both the order and the size than the BNA pattern during memorization. The situation is different following treatment with Scopolamine and Ketamine. The scopolamine (FIGS. 10C-D) induced (i) low connectivity between frontal and parietal regions, and (ii) extensive compensatory central and frontal activation. The ketamine (FIGS. 10G-H) induced increased central and frontal activation, and decreased right lateralization. No significant change in the fronto-parietal part of the BNA pattern was observed.

Further details regarding analysis of neurophysiological data acquired from subjects administered with scopolamine are provided in the Examples section that follows (see Example 4).

The BNA pattern comparison technique of the present embodiments can also be used for inducing improvement in brain function. In some embodiments of the present invention associated subject-specific BNA patterns are constructed for a subject during a higher-level cognitive test, generally in real time. The subject can be presented with the constructed BNA patterns or some representation thereof and use them as a feedback. For example, when, as a result of the cognitive action, the BNA pattern of the subject becomes more similar to a characteristic BNA pattern of a healthy group, presentation of such a result to the subject can be used by the subject as a positive feedback. Conversely, when, as a result of the cognitive action, the BNA pattern of the subject becomes more similar to a characteristic BNA pattern of a brain-disorder group, presentation of such a result to the subject can be used by the subject as a negative feedback. Real time analysis of BNA patterns in conjunction with neurofeedback can optionally and preferably be utilized to achieve improved cortical stimulation using external stimulating electrodes.

The BNA pattern comparison technique of the present embodiments can also be used for assessing responsiveness to and optionally efficacy of a phototherapy. Phototherapy is the application of light energy to biological tissue for the purpose of stimulating certain biological functions, such as natural tissue healing and regrowth processes. Alternatively, a higher power level of phototherapy may inhibit natural biological functions of the tissue or destroy the tissue, as may be applied in the case of cancerous tissue.

Generally, phototherapy is accomplished by radiating light energy into a subject's tissue at or below the skin or surface of the tissue. The radiation is applied at wavelengths either in the visible range or the invisible infrared (IR) range. Phototherapy may also be accomplished by applying coherent and non-coherent light energy, lased and non-lased light energy, and narrow and broadband light energy, in either a continuous or pulsed manner. The radiation energy is also typically applied at a low power intensity, typically measured in milliwatts. The relatively low radiation energy applied in therapy is called low level light therapy (LLLT). LLLT has also been suggested for neurological disorders in the CNS, for the prevention and/or repair of damage, relief of symptoms, slowing of disease progression, and correction of genetic abnormalities. In particular, phototherapy can be used following a cerebrovascular accident (stroke).

The present embodiments can be used for assessing the responsiveness to and optionally the efficacy of phototherapy, particularly LLLT of neurological disorders. Such assessment can be done by constructing BNA patterns from neurophysiological data acquired before, after and optionally during phototherapy and comparing those BNA patterns among themselves and/or to baseline BNA pattern as further detailed hereinabove.

The BNA pattern comparison technique of the present embodiments can also be used for assessing responsiveness to and optionally efficacy of hyperbaric therapy. Hyperbaric therapy is indicated for many medical conditions, therapeutic purposes, and training regimens. Hyperbaric treatment can aid in the treatment of many oxygen dependent diseases as well as sports injuries. Some of the ailments that can be effectively treated by hyperbaric therapy include: cerebral edema, traumatic head and spinal cord injury, chronic stroke, post stroke, early organic brain syndrome, brain stem syndromes, brain ischemia, brain blood circulation disturbances and headache disorder. Typically, treatment in a hyperbaric chamber is provided by administering oxygen to the user via a closed-circuit mask, hood, or other device while a hyperbaric chamber is maintained at pressures above ambient pressure. The oxygen is supplied to the user from a supply source external to the chamber. The subject exhales through a closed system back outside the chamber such that the ambient air in the chamber remains less than 23.5% oxygen or is not oxygen enriched. The environment within the chamber is also generally maintained by a source external to the chamber and is generally controlled by a thermostat.

Assessment of responsiveness to and/or efficacy of hyperbaric therapy can be done by constructing BNA patterns from neurophysiological data acquired before, after and optionally during hyperbaric therapy and comparing those BNA patterns among themselves and/or to baseline BNA pattern as further detailed hereinabove.

Additional examples of treatments which may be assessed by the BNA pattern comparison technique of the present embodiments include, without limitation, ultrasound treatment, rehabilitative treatment, and neural feedback, e.g., EMG biofeedback, EEG neurofeedback, transcranial magnetic stimulation (TMS), and direct electrode stimulation (DES).

Aside for MPH, scopolamine and ketamine described above, the BNA pattern comparison technique can be used for assessing responsiveness to and optionally efficacy of many other types of pharmacological treatments.

For example, when the subject suffers from a neurodegenerative disorder such as Alzheimer's disease, the treatment can include use of pharmacologically active agent selected from the group consisting of donepezil, physostigmine, tacrine, pharmaceutically acceptable acid addition salts thereof, and combinations of any of the foregoing; when the subject suffers from a neurodegenerative disorder such as Huntington's disease, the treatment can include use of pharmacologically active agent selected from the group consisting of fluoxetine, carbamazepine, and pharmaceutically acceptable acid addition salts and combinations thereof; when the subject suffers from a neurodegenerative disorder such as Parkinson's disease, the treatment can include use of pharmacologically active agent selected from the group consisting of amantadine, apomorphine, bromocriptine, levodopa, pergolide, ropinirole, selegiline, trihexyphenidyl, atropine, scopolamine, glycopyrrolate, pharmaceutically acceptable acid addition salts thereof, and combinations of any of the foregoing; and when the subject suffers from a neurodegenerative disorder such as amyotrophic lateral sclerosis (ALS) the treatment can include use of pharmacologically active agent selected from the group consisting of baclofen, diazepam, tizanidine, dantrolene, pharmaceutically acceptable acid addition salts thereof, and combinations of any of the foregoing.

Generally, pharmacological treatments can include use of a pharmacologically active agent, e.g., centrally acting drugs, particularly CNS active agents and other nervous system agents, including, but not limited to, the following: sympathomimetic amines; neuroprotective and neuroregenerative agents, including neurotrophic factors; neuroactive amino acids and peptides; neurotransmitters; muscarinic receptor agonists and antagonists; anticholinesterases; neuromuscular blocking agents; ganglionic stimulating drugs; agents to treat neurodegenerative disorders such as Alzheimer's disease, Huntington's disease, Parkinson's disease, and amyotrophic lateral sclerosis (ALS); anti-epileptic agents; CNS and respiratory stimulants; and drugs that selectively modify CNS function, including anesthetic agents, analgesic agents, antiemetic agents, antihypertensive agents, cerebral vasodilators, hypnotic agents and sedatives, anxiolytics and tranquilizers, neuroleptic agents, anti-microbial agents, alpha adrenergic receptor antagonists, and appetite suppressants. Some agents, as will be appreciated by those of ordinary skill in the art, are encompassed by two or more of the aforementioned groups.

Examples of these pharmacologically active agents include, without limitation, sympathomimetic amines (e.g., include albuterol, amphetamine, benzphetamine, colterol, diethylpropion, dopamine, dopamine hydrochloride, dobutamine, ephedrine, epinephrine, epinephrine bitartrate, ethylnorepinephrine, ethylnorepinephrine hydrochloride, fenfluramine, fenoldapam, fenoldopam, fenoldopam mesylate, hydroxyamphetamine, hydroxyamphetamine hydrobromide, ibopamine, isoetharine, isoproterenol, isoproterenol hydrochloride, mephentermine, mephentermine sulfate, metaproterenol, metaraminol, metaraminol bitartrate, methoxamine, methoxamine hydrochloride, midodrine, norepinephrine, norepinephrine bitartrate, phendimetrazine, phenmetrazine, phentermine, phenylephrine, phenylephrine hydrochloride, phenylethylamine, phenylpropanolamine, prenalterol, propylhexedrine, ritodrine, terbutaline, terbutaline sulfate, and tyramine); Neuroprotective and neuroregenerative agents (e.g., excitatory amino acid antagonists and neurotrophic factors, e.g., brain derived neurotrophic factor, ciliary neurotrophic factor, and nerve growth factor, neurotrophin (NT) 3 (NT3), NT4 and NT5); Neuroactive amino acids and peptides (e.g., γ-aminobutyric acid (GABA), glycine, β-alanine, taurine, and glutamate, and the neuroactive peptides include bradykinin, kallidin, des-Arg.sup.9-bradykinin, des-Arg.sup.10-kallidin, des-Arg.sup.9-[Leu.sup.8]-bradykinin, [D-Phe.sup.7]-bradykinin, HOE 140, neuropeptide Y, enkaphalins and related opioid peptides such as Met.sup.5 enkaphalin, Leu.sup.5-enkephalin, α-, β- and γ-endorphin, α- and β-neo-endorphin, and dynorphin; neurotransmitters (e.g., GABA (γ-aminobutyric acid), glycine, glutamate, acetylcholine, dopamine, epinephrine, 5-hydroxytryptamine, substance P, serotonin, enkaphalins and related opioid peptides as above, and catecholamines; Muscarinic receptor agonists and antagonists (e.g., choline esters such as acetylcholine, methacholine, carbachol, bethanechol (carbamylmethylcholine), bethanechol chloride; cholinomimetic natural alkaloids and synthetic analogs thereof, including arecoline, pilocarpine, muscarine, McN-A-343, and oxotremorine. Muscarinic receptor antagonists are generally belladonna alkaloids or semisynthetic or synthetic analogs thereof, such as atropine, scopolamine, homatropine, homatropine methylbromide, ipratropium, methantheline, methscopolamine and tiotropium; anticholinesterases (e.g., ambenonium, ambenonium chloride, demecarium, demecarium bromide, echothiophate iodide, edrophonium, edrophonium chloride, neostigmine, neostigmine bromide, neostigmine methylsulfate, physostigmine, physostigmine salicylate, pyridostigmine, and pyridostigmine bromide); neuromuscular blocking agents and ganglionic blocking drugs (e.g., dicholine esters (e.g., succinylcholine), benzylisoquinolines (d-tubocurarine, atracurium, doxacurium, mivacurium) and pipecuronium, rocuronium, vecuronium), hexamethonium, trimethaphan, and mecamylamine; agents to treat neurodegenerative diseases (e.g., active agents for treating Alzheimer's disease, such as Donezepil, donepezil hydrochloride, physostigmine, physostigmine salicylate, tacrine and tacrine hydrochloride, active agents for treating Huntington's Disease such as, but not limited to, fluoxetine and carbamazepine, anti-Parkinsonism drugs such as, but not limited to, amantadine, apomorphine, bromocriptine, levodopa (particularly a levodopa/carbidopa combination), pergolide, ropinirole, selegiline, trihexyphenidyl, trihexyphenidyl hydrochloride, and anticholinergic agents; and agents for treating ALS such as, but not limited to, spasmolytic (anti-spastic) agents, e.g., baclofen, diazepam, tizanidine, and dantrolene); anti-epileptic agents (e.g., anti-convulsant (anti-seizure) drugs such as azetazolamide, carbamazepine, clonazepam, clorazepate, ethosuximide, ethotoin, felbamate, gabapentin, lamotrigine, mephenyloin, mephobarbital, phenyloin, phenobarbital, primidone, trimethadione, vigabatrin, and the benzodiazepines which are useful for a number of indications, including anxiety, insomnia, and nausea); and CNS and respiratory stimulants (e.g., xanthines such as caffeine and theophylline; amphetamines such as amphetamine, benzphetamine hydrochloride, dextroamphetamine, dextroamphetamine sulfate, levamphetamine, levamphetamine hydrochloride, methamphetamine, and methamphetamine hydrochloride; and miscellaneous stimulants such as methylphenidate, methylphenidate hydrochloride, modafinil, pemoline, sibutramine, and sibutramine hydrochloride).

Also contemplated are drugs that selectively modify CNS function. These include, without limitation, anesthetic agents such as ketamine; opioid analgesics such as alfentanil, buprenorphine, butorphanol, codeine, drocode, fentanyl, hydrocodone, hydromorphone, levorphanol, meperidine, methadone, morphine, nalbuphine, oxycodone, oxymorphone, pentazocine, propoxyphene, sufentanil, and tramadol; nonopioid analgesics such as apazone, etodolac, diphenpyramide, indomethacine, meclofenamate, mefenamic acid, oxaprozin, phenylbutazone, piroxicam, and tolmetin; antiemetics such as chlorpromazine, cisapride, domperidone, granisetron, metoclopramide, ondansetron, perphenazine, prochlorperazine, promethazine, thiethylperazine, and triflupromazine; antihypertensive agents such as apraclonidine, clonidine, guanfacine, and guanabenz; cerebral vasodilators such as vincamine, naftidrofuryl oxalate, papaverine, and nicotinic acid; hypnotic agents and sedatives such as clomethiazole, ethinamate, etomidate, glutethimide, meprobamate, methyprylon, zolpidem, and barbiturates (e.g., amobarbital, apropbarbital, butabarbital, butalbital, mephobarbital, methohexital, pentobarbital, phenobarbital, secobarbital, thiopental); anxiolytics and tranquilizers such as benzodiazepines (e.g., alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, triazolam), buspirone, and droperidol; neuroleptic agents, including antidepressant drugs, antimanic drugs, and antipsychotic agents, wherein antidepressant drugs include (a) the tricyclic antidepressants such as amoxapine, amitriptyline, clomipramine, desipramine, doxepin, imipramine, maprotiline, nortryptiline, protryptiline, and trimipramine, (b) the serotonin reuptake inhibitors citalopram, fluoxetine, fluvoxamine, paroxetine, sertraline, and venlafaxine, (c) monoamine oxidase inhibitors such as phenelzine, tranylcypromine, and (−)-selegiline, and (d) other, "atypical" antidepressants such as bupropion, nefazodone, and trazodone venlafaxine, and antimanic and antipsychotic agents include (a) phenothiazines such as acetophenazine, acetophenazine maleate, chlorpromazine, chlorpromazine hydrochloride, fluphenazine, fluphenazine hydrochloride, fluphenazine enanthate, fluphenazine decanoate, mesoridazine, mesoridazine besylate, perphenazine, thioridazine, thioridazine hydrochloride, trifluoperazine, and trifluoperazine hydrochloride, (b) thioxanthenes such as chlorprothixene, thiothixene, and thiothixene hydrochloride, and (c) other heterocyclic drugs such as carbamazepine, clozapine, droperidol, haloperidol, haloperidol decanoate, loxapine succinate, molindone, molindone hydrochloride, olanzapine, pimozide, quetiapine, risperidone, and sertindole; anticholinergic drugs such as atropine, scopolamine and glycopyrrolate; anti-microbial agents such as (a) tetracycline antibiotics and related compounds (chlortetracycline, oxytetracycline, demeclocycline, methacycline, doxycycline, rolitetracycline), (b) macrolide antibiotics such as erythromycin, clarithromycin, and azithromycin, (c) streptogramin antibiotics such as quinupristin and dalfopristin, (d) beta-lactam antibiotics, including penicillins (e.g., penicillin G, penicillin VK), antistaphylococcal penicillins (e.g., cloxacillin, dicloxacillin, nafcillin, and oxacillin), extended spectrum penicillins (e.g., aminopenicillins such as ampicillin and amoxicillin, and the antipseudomonal penicillins such as carbenicillin), and cephalosporins (e.g., cefadroxil, cefepime, cephalexin, cefazolin, cefoxitin, cefotetan, cefuroxime, cefotaxime, ceftazidime, and ceftriazone), and carbapenems such as imiprenem, meropenem and aztreonam, (e) aminoglycoside antibiotics such as streptomycin, gentamicin, tobramycin, amikacin, and neomycin, (f) glycopeptide antibiotics such as vancomycin, and teicoplanin; (g) sulfonamide antibiotics such as sulfacetamide, sulfabenzamide, sulfadiazine, sulfadoxine, sulfamerazine, sulfamethazine, sulfamethizole, and sulfamethoxazole, (h) quinolone antibiotics such as ciprofloxacin, nalidixic acid, and ofloxacin; (i) anti-mycobacterials such as isoniazid, rifampin, rifabutin, ethambutol, pyrazinamide, ethionamide, aminosalicylic, and cycloserine, (j) systemic antifungal agents such as itraconazole, ketoconazole, fluconazole, and amphotericin B, (k) antiviral agents such as acyclovir, famcicylovir, ganciclovir, idoxuridine, sorivudine, trifluridine, valacyclovir, vidarabine, didanosine, stavudine, zalcitabine, zidovudine, amantadine, interferon alpha, ribavirin and rimantadine, and (l) miscellaneous antimicrobial agents such as chloramphenicol, spectinomycin, polymyxin B (colistin), and bacitracin; alpha adrenergic receptor antagonists such as doxazosin, indoramine, phenoxybenzamine, phentolamine, prazosin, tolazoline, terazosin, trimazosin, and yohimbine; and appetite suppressants such as amphetamine, dextroamphetamine, dextroamphetamine sulfate, diethylpropion hydrochloride, mazindol, methamphetamine hydrochloride, phentermine, and phentennine hydrochloride.

According to an aspect of some embodiments of the present invention there is provided a system for analyzing neurophysiological data. The system comprises a data processor, e.g., a dedicated circuitry or a general purpose computer, configured for receiving the neurophysiological data, and executing at least some of the operations described herein.

As used herein the term "about" refers to ±10%.

The word "exemplary" is used herein to mean "serving as an example, instance or illustration." Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments." Any particular embodiment of the invention may include a plurality of "optional" features unless such features conflict.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Example 1

BNA Pattern of ADHD Subjects

ADHD is a common developmental disorder characterized by inattention, hyperactivity, and impulsivity. In children diagnosed with ADHD, symptoms often persist into adulthood. Although the clinical manifestations may change with maturity, impulsivity, a deficiency in inhibiting behavior in response to situational demands, remains a dominant behavioral feature of the disorder in adults. It is recognized by the present inventors that in ADHD subjects there is lack of inhibitory control, implying that response inhibition also mediates other functional deficits underlying ADHD symptoms. One of the most widely used paradigms for evaluating response inhibition is the Go/No-go test (Liddle et al., 2001; Baum, 2001; Garavan et al., 2002), a paradigm which requires subjects to make rapid responses to baseline and outlier stimuli.

The technique of the present embodiments has been utilized to analyze ERP responses of a group of ADHD subjects and a group of matching control subjects to an auditory Go/No-go task.

Methods

Subjects

Thirteen adults of both genders diagnosed with the combined subtype of ADHD and thirteen age and gender matched controls participated in the study. All were right-handed and reported to have normal hearing and normal or corrected-to-normal vision. ADHD subjects were recruited from the Neuro-Cognitive Unit at the Rambam Health Care Campus, Israel. Nine were diagnosed with ADHD from childhood. Controls were student volunteers from the Technion—Israel Institute of Technology. All subjects underwent a comprehensive neurological and neuropsychological evaluation. ADHD subjects fulfilled DSM-IV (Diagnostic and Statistical Manual of Mental Disorders, 4th edition; Association, 2000) criteria and ADHD symptoms according to translated versions of the Conners Adult ADHD Rating Scales (Murphy and Adler, 2004). The ADHD group did not differ from the normal group on the Raven's Progressive Matrices score. Subjects with co-morbid disorders (such as depression, anxiety, substance abuse and learning disabilities) were excluded. Six of the thirteen ADHD subjects reported regular Methylphenidate therapy. All subjects were evaluated following a minimum of 24 hours medication washout. The protocol was approved by the Rambam institutional review board for experiments involving human subjects (Helsinki Committee) and all participants signed an informed consent before participating in the study.

An additional ADHD group of fifteen subjects was recruited from the Massachusetts General Hospital (MGH) in Boston. These subjects were all diagnosed with ADHD according to DSM-IV TR criteria, established in a clinical interview with an expert staff psychiatrist. Clinician Global Impression of Severity Scale (CGI-S), Adult Attention-Deficit/Hyperactivity Disorder Investigator Symptom Rating Scale (AISRS) and ADHD Rating Scale (ADHD-RS) were also performed for this additional group (Guy 1976, Spencer 2004).

Unless otherwise stated, reference to ADHD group is to be understood as a reference to ADHD subjects recruited from the Rambam Health Care Campus, and a reference to the additional ADHD group is to be understood as a reference to the ADHD subjects recruited from the Massachusetts General Hospital.

Stimuli

Stimuli consisted of 1000 and 2000 Hz 40 ms duration pure tones, presented binaurally at 60 dB with a rectangular envelope. Go trials (2000 Hz tone) were presented in 80% of the trials and the subject was instructed to press a button as fast as possible in response to this tone. The No-go trials (1000 Hz) were presented in the remaining 20% of the trials and the subject was instructed to refrain from responding. Stimuli were presented pseudo-randomly and the time interval between stimuli varied randomly between 1000 and 2000 ms. Following a 10-trial practice block, subjects were presented with five recording blocks, each consisting of 200 trials. Subjects were instructed to respond with a button press using the index finger of their right hand.

Experimental Procedure

ERPs were recorded using 9 mm silver disk electrodes filled with conducting gel and attached to the scalp by collodion glue at positions Fp1, Fp2, F7, F3, Fz, F4, F8, T3, C3, Cz, C4, T4, T5, P3, Pz, P4, T6, O1, O2, as well as at the left and right mastoids (A1 and A2), a total of 21 sites. Activity was recorded (Ceegraph IV Biologic Systems Corp., IL, USA) with all EEG electrodes referenced to the center of the chin, and an electrode on the left forearm as ground. An electrode below the left eye, referenced to Fz, served to record eye movements (EOG). Impedance at each electrode was maintained below 5 kΩ. Potentials from the EEG (×100,000) and EOG (×20,000) channels were amplified, digitized with a 12 bit A/D converter at a rate of 256 samples/sec, filtered (0.1-100 Hz, 6 dB/octave slopes) and stored for off-line analysis Subjects performed the task reclining in an adjustable armchair in an acoustically isolated chamber, listening to the auditory stimuli presented by earphones and responding with a pushbutton box in their right hand. Subjects were instructed to avoid eye movements and blinking as much as possible, and to keep their gaze on a fixed point in front of them during task performance.

Data Processing—Overview

FIG. 11 is a scheme illustrating the method employed in the present example and in accordance with some embodiments of the present invention. In FIG. 11, the blue arrows represent computational operations for group networks recognition, and the red arrows represent computational operations for individual subject evaluation.

Preprocessing and artifact rejection, band-passing, discretization and normalization were initially performed on the individual recordings both for group networks recognition and for individual subject evaluation.

For each of the first ADHD group, the additional ADHD group and the Control group, the activity peaks of the entire group were pooled, projected onto a three-dimensional feature space (time, frequency, location), and processed to extract databases of brain patterns and to construct group BNA patterns. The constructed BNA patterns distinctively characterized the respective group, hence facilitating group networks recognition.

BNA patterns of individual subjects were also constructed by treating each individual subject separately. The activity peaks of each such individual subject were processed to form a subject-specific BNA pattern which was then compared to the group BNA patterns. This allows graded classification of each individual subject to each of the groups. The BNA pattern comparison further allowed subject evaluation and correlation to behavioral measures.

Details of the data processing as delineated above will now be described.

ERP Waveform Analysis

Continuous individual records were processed offline by segmentation to epochs beginning 300 ms before until 1000 ms after tone onset (FIG. 11, preprocessing). These records were selectively averaged according to the stimulus type (Go and No-go) after eye movement correction based on blind source separation, utilizing independent component analysis (see, e.g., Makeig et al., 1996). Only No-go epochs associated with correct responses and free of excessive (<100 μV) electrical activity were included in the average. After averaging, the data were band-pass filtered (IIR rectangular filter with a 0.5-30 Hz band-pass filter). Go epochs were not included in this study.

Each electrode was then filtered into overlapping frequency bands in order to separate the EEG activity into basic well known brain processes (Klimesch, 1999; Basar et al., 2001). Frequency bands were defined as follows: delta band (1-4 Hz), theta band (3-8 Hz), alpha band (7-13 Hz), low beta band (12-18 Hz), beta band (17-23 Hz), and high beta band (22-30 Hz). All overlapping frequency bands were used in the next stages of the analysis such that no loss of information occurred. FIG. 11 shows an example of the band-passing stage of a single electrode averaged activity in response to a No-go stimulus of an ADHD subject.

Data Reduction: Discretization and Normalization

Following the waveform analysis, activity was reduced into a set of discrete points which describe all the waveforms' local extrema at each frequency band. Due to the near-symmetry of the waveforms around the waveform peak, each local waveform was thus reduced to a pair of numbers denoting the latency and the amplitude of the negative and positive peaks (FIG. 11, discretization).

Following discretization, the within-subject peaks representing the activity in each electrode for each frequency band were z-score normalized in order to standardize across subjects and frequencies (FIG. 11, normalization) in the following manner: for each electrode and within each frequency band, z-scores were computed based on maxima and minima points only. For each subject, all z-scores of all electrodes within each frequency band were then pooled together. The z-scores of local positive and negative peaks which passed a predetermined threshold (z-score threshold) were selected and their corresponding latencies and amplitudes were utilized as input for network analysis. In addition to compensating for impedance differences, the normalization contributed to noise reduction.

Several z-score thresholds were employed: the top 40% of the z-score points were taken for the delta frequency band, the top 18.2% of the z-score points were taken for the for theta frequency band, the top 10% of the z-score points were taken for the alpha frequency band, the top 6.7% of the z-score points were taken for the low beta frequency band, the top 5% of the z-score points were taken for the beta frequency band, and the top 3.8% of the z-score points were taken for the high beta frequency band.

Network Analysis

Following data reduction, the entire test-related activity of all subjects in each experimental group was considered as a set of discrete points in a three dimensional space of time (peak latency), frequency, and electrode (location). FIG. 11 demonstrates this concept for 3 subjects from the Control group, each being represented by a different color (network analysis, right window). Points which passed the z-score threshold were projected in the feature space on an all or none basis. In the present example, the specific amplitude level of each point was kept for later stages but was not included as a separate dimension. However, use of 4 dimensional space wherein the additional dimension is the amplitude is also contemplated, at least in some embodiments of the present invention.

Within this 3D space, a single prevalent activity event (negative or positive peak in any of the frequency bands) in a sub-group of subjects appeared as a cluster of tightly distributed discrete points. The width of such a cluster in a given dimension was used to define the activity window size for that dimension variable. For example, the width of a cluster in the time dimension was used to describe the latency range within which the event can occur across subjects. Thus, each cluster represented activity mutual to a sub-group of subjects, in a small set of adjoining electrodes, within a defined frequency band and with a defined latency range. A time sequence of such clusters was treated as a spatiotemporal pattern of network activity. The goal of the network analysis of the present example was to extract those activity patterns that were consistent across subjects and to attempt to reveal distinctive patterns as well as prevalent junction connections that characterized each of the subject groups.

In the time dimension, single clusters represented unitary events which occurred within a time window. This window was narrowed to exclude obvious outliers and constrain the permitted range of latencies. A succession of such unitary events describes an evolving spatiotemporal pattern with a fixed time windows for each event in the sequence. To maintain temporal relations between events across subjects, pattern extraction was implemented for each experimental group using the following procedure which utilizes density-based clustering methods (FIG. 11, network analysis).

Initially, for each frequency band, clusters of unitary activity (positive and negative peaks) in the time domain were located, using a running window with a predetermined and fixed window size. Thresholding using an adjustable subject threshold parameter was used to discard clusters not hosting a minimal number of subjects. In the present example, the minimal number of subjects in a cluster was initially set to 11, and was adapted thereafter. For the remaining clusters, the initial predetermined window was narrowed to the minimal width that satisfied the subject threshold. Next, for each subject appearing in each possible pair of clusters, the latency difference (including zero difference) between the appearances of the two unitary events was computed. The range of these differences was then examined: if a sufficient number of differences (above 10 differences, in the present example), as allowed by the subject threshold, were found to be contained within a predetermined window, the pair of events was accepted as a "pair-pattern" mutual to all subjects fulfilling the variability constraint.

A pair-pattern included either two simultaneous events in two different locations or two successive events in the same or different locations. Such pair-pattern formed an elementary spatiotemporal unit.

Next, unit spatiotemporal patterns with a common unitary activity were concatenated to form complex patterns of more than two unitary activities. The group of subjects sharing the new pattern was determined by the cross-section of the two groups of subjects who partook in the two appended patterns. Resulting three unit patterns which did not meet the subject threshold were discarded. Patterns with more than three units were constructed in a similar fashion. Finally, redundant patters were removed such that for each experimental group a minimal set of unique multi-location patterns was revealed. Each of the remaining patterns defines a synchronized network containing the maximum number of nodes that survived the staged appending process.

FIG. 11 (see network analysis) demonstrates the effect of the network analysis on the set of discrete data points. The entire set of discrete data points in the original 3D space has been reduced into a smaller subset of points which participated in the set of extracted patterns (in this case for 3 subjects only, for demonstration purposes). Note that while there appear to be several potential clusters prior to the network analysis, only a small number remain. The two yellow arrowheads in FIG. 11 mark two such clusters shared by all three subjects. Note that the temporal relations x-axis distance) between the two clusters are similar for all subjects within the cluster. These clusters also participated in the Control pattern, presented in FIG. 12 below, shared by all 13 subjects in the Control group.

In addition to revealing network activity which characterized a given group, an additional goal of the network analysis of the present example was to identify network activity which distinguishes between groups. Thus, for each extracted pattern, the number of subjects in which the pattern appeared was found for both groups. The difference between these two numbers is referred to below as the differentiation level of the pattern. To identify distinguishing patterns, a thresholding procedure was employed. Specifically, only patterns which passed a differentiation level threshold of 12 were accepted as distinguishing patterns, while all other patterns were rejected. A distinguishing pattern was assigned with a group-subject value, defined as the number of subjects in the respective group for which the distinguishing pattern was identified.

Classification

Classification of an unclassified subject was performed using a k-folds cross validation algorithm, as follows. Since all subjects in this study were pre-classified, each subject in turn was removed from its group and treated as if he were a novel, unclassified subject. The BNA pattern analysis described above was then re-executed on the two groups and the distinguishing patterns were identified as described above. Thus, the identified distinguishing patterns did not include the individual subject.

For each of the extracted distinguishing patterns in both groups, a weight index (WI) was given to all participating elementary spatiotemporal units (pair-pattern), based on several properties of the pair. WI was determined by the number of subjects participating in the pair, the differentiation level of the pair-pattern, and the width of the narrowed-down time windows (the narrower the windows the greater the weight).

The individual subject was classified to one of the two groups by computing the similarity between the individual subject's electrodes activity and the activity requirements of each of the distinguishing patterns. This similarity is referred to as similarity index (SI). The comparison was made for each participating pair-pattern, in three different aspects: connectivity, synchronization and amplitude, thereby computing three similarity indices: SIc, SIs and SIa, respectively.

The SIc of a pair-pattern was 1 if it applied at all to the tested subject (i.e. the subject's electrode activity fulfilled the constraints set by the pair-pattern) and 0 if it did not. To assess the SIs of all pair-patterns with an SIc of 1, the times of the discrete activity points of the individual subject were compared to the mean and SD of the activity times of the group pair-pattern, for each of the two regions. The SIa of the pair was evaluated in a similar manner, by comparing the amplitudes of the activity points. The overall classification score of the individual subject to each of the groups was computed by averaging the products WI·SI of all pairs in all patterns of the group. The classification score was computed separately for each similarity index such that three classification scores were computed: a connectivity score, a synchronization score and an amplitude score. The individual subject was classified to the group for which the subject achieved the higher classification score. This classification was done for each of the three scores (Table 1).

Finally, the difference between the tested subject's SI score to the ADHD group and to the Control group was taken as an estimate of his/her ADHD index. Three such ADHD indices were defined, one for each similarity score. These three quantitative ADHD indices were utilized to determine the ability of the method of the present embodiments to predict the behavioral measures of the test subject, based on his brain activity, by correlating them to the independently derived behavioral scores (FIG. 16).

Outlier Removal

An additional computation operation employed in the present example included automatic identification of outliers in the group. The advantage of using this operation is that it facilitates further narrowing of the time-windows hence allows extension of the patterns to more locations over the brain. The following procedure was used to automatically identify outliers in the Control group and in the ADHD group. The three ADHD indices above were computed for each subject. The mean and standard deviation (SD) of each ADHD index were then computed within each group separately. A subject in which all three ADHD indices were outside the range of mean±2 SD was identified as an outlier. After outlier removal (one for each group) network analysis was repeated for the refined (core) groups. Based on the patterns revealed from the core groups, classification of all subjects (including outliers) was repeated. The results presented in FIGS. 14-16 below pertain to the core groups.

For the additional group of subjects, the procedure was similar. Briefly, 64-electrode EEG data were collected across multiple areas, frequencies and timescales. Pre-processed EEG data was band pass filtered into overlapping physiological frequency bands, epoched and averaged to ERPs. For each band, data were reduced into a set of discrete points to denote local extrema. For each condition the algorithm searched for synchronous peak latencies across subjects. Next, peak-pair patterns were identified, such that inter-peak intervals were also synchronous across subjects. More complicated patterns of 3 or more peaks were also identified, until a state-unique multi-sited spatio-temporal pattern or several patterns emerged. Most distinguishing patterns were then used as opposing poles. Subjects were assigned similarity indices that quantified degree to which individual BNA pattern matched that of each pole, for each condition.

Results

Network Analysis of Control Group Activity

Patterns of electrode activity which distinguished the Control group No-go activity from the ADHD group No-go activity were automatically revealed by the BNA pattern analysis of the present embodiments. These distinguishing patterns are referred to below as Control patterns.

An example of a Control pattern is presented in FIG. 12. This Control pattern involved a set of mainly right-hemispheric frontal-central-parietal electrodes (distribution on scalp in center of FIG. 12), with delta frequency dominating. The brain image presents the locations upon the scalp of the electrodes participating in the pattern. For each electrode (one is omitted from FIG. 12 for clarity of presentation), a compound panel depicting the individual activity (top two panels) and the time-running grand average of the activities (bottom two panels) of subjects in the Control group (left) and the ADHD group (right) is presented.

The frequency band of the electrode activity is displayed at the top-center of the compound panel. For each group, the upper colored panel has 13 rows, one for each subject. In each row, the subject's non-normalized average activity for the duration of the recorded epoch is presented by a color scale, with blue being the extreme negative and red the extreme positive. Vertical lines in the upper panels represent the minimal (left) and maximal (right) latency limits of the electrode activity within the pattern. Time segments bounding positive activity are marked in red, and time segments bounding negative activity are marked in blue. Dots represent positive (red) or negative (blue) peaks of activity which passed the z-score amplitude threshold within the time segment of the pattern for that subject.

The mean and standard deviation of the peak-activity latencies (ms) within the bounds of the time segment(s) of all participating subjects are presented in parenthesis below the upper panels. White arrowhead in panel of electrode Fz marks the activity peak of a single Control subject which was automatically selected as an outlier (see text). Blue arrowhead and red arrowhead in panel of electrode C3 mark the N100 component and the P300 component in the grand average activity respectively.

A given subject was declared as fulfilling the entire pattern, if the activity peaks appeared in all time windows of all electrodes participating in the pattern. The pattern presented in FIG. 12 was found in all Control subjects (N=13). Thus, the pattern had a group-subject value of 13. Only one ADHD subject fulfilled the complete set of requirements for this pattern, leading to a pattern differentiation level of 13−1=12.

For each time/subject rectangle, the grand average of the discretized but un-normalized activity amplitudes was computed (narrow rectangles below the colored panel). The resulting trace thus approximates the group's average ERP for the corresponding frequency at this location. The traces indicate that the dominant unit activities in most participating electrodes are the large N100 component (peak marked by blue arrowhead in the grand average panel of electrode C3) followed by a prominent P300 component (peak marked by red arrowhead in same trace).

The single-subject latencies of the two events in all connected pair-patterns of a network were extracted and analyzed so as to identify network which is a multi-sited scalp representation of activity spreading from a single source. 193 such pairs were involved in the most distinguishing Control pattern network, with mean latency differences (ΔLs) ranging from 0.3-240 ms. Nonparametric paired testing of the differences between means (Wilcoxon signed-rank test) found 75.3% of the 193 ΔLs to be significantly ($p<0.05$) different from zero. These included 89 pairs with ΔLs of about 200 ms, which again could be construed to represent a scalp-wide manifestation of two conducted, deeply generated events related to the N100 and P300 components. However, even when only considering the 104 pair-patterns with temporally adjacent events ($\Delta L<\pm 35$), 59% were found to be significantly different from zero. A similar inspection and testing of the ADHD most distinguishing network, this one with 293 pairs, also found 59% of the 183 $\Delta Ls<\pm 65$ to be significantly different from zero.

The N100 and P300 components were noticeably weaker in the grand averages from the respective electrodes in the ADHD group. This resulted from both reduced individual ERP amplitudes and high latency variability in the ADHD subjects, compared to the Control subjects. The consequence of this high variability was that despite the fact that several ADHD subjects had large peak amplitudes, their latencies did not fall within the temporal constraints of the Control patterns. In addition to the pattern shown in FIG. 12, most of the activity (75% of the regions) in the other extracted patterns was expressed in the delta frequency band.

A white arrowhead in FIG. 12 marks the peak activity points of the Control subject which was automatically identified as an outlier. The posterior activity (electrodes P3, Pz and P4) of this subject was characterized by smaller amplitudes compared to the rest of the Control group. In addition, in all electrodes participating in the pattern, the latency of the peak activity of the outlier was shorter than that of the rest of the group. In this respect, the electrode activity of this subject was more similar to the activity of the ADHD group, however, he did not demonstrate the entire network activity which characterized the ADHD group, as is further described below.

Network Analysis of ADHD Group Activity

Patterns of electrode activity which best distinguished the ADHD group No-go activity from that of the Control group were also automatically revealed by the BNA pattern analysis optionally and preferably. These distinguishing patterns are referred to herein as ADHD patterns.

An example of an ADHD pattern is shown in FIG. 13. The format presented in FIG. 13 is the same as in FIG. 12. White arrowhead in the panel of electrode C3 marks the activity peak of a single ADHD subject which was automatically selected as an outlier.

A given subject was declared as fulfilling the entire pattern, if the activity peaks appeared in all time windows of all electrodes participating in the pattern. The pattern presented in FIG. 13, with theta and alpha frequency bands dominating, was found in all ADHD subjects (N=13) and in only one Control subject. Thus, this pattern had a group-subject value of 13 and a pattern differentiation level of 13−1=12.

The grand averaged activity of the ADHD subjects in the specific frequencies that participated in the pattern revealed a large negative component between 150-170 ms in all electrodes participating in the pattern, larger as compared to the Control activity, possibly indicating an enhanced N200 component in the ADHD group. Here too, peak-activity latencies in several of the participating electrodes differed significantly by as much as 30 ms.

A white arrowhead in FIG. 13 marks the peak activity points of the ADHD subject which was automatically identified as an outlier. Unlike the control group outlier, this outlier was the only ADHD subject which fulfilled all constraints of the Control pattern (FIG. 12). The two outlier subjects (one Control subject and one ADHD subject) were removed from here on, in all further analyses. Automatic removal of the outliers enabled detection of refined patterns which better described the BNA pattern in the core groups.

The patterns presented in FIGS. 12 and 13 are examples of the automatically revealed unitary events in all participating locations. In the present example, the connectivity between the different regions sharing the distinguishing patterns was also analyzed, as is further explained below.

Two distinguishing BNA patterns of the Control group and the ADHD group, now after outlier removal, are presented in FIGS. 14A and 14B respectively. The nodes mark unitary events which took part in the patterns. The location of the node represents the electrode in which the event occurred, and the color of the node represents the frequency band(s) of the activity (red marks the delta band, green marks the theta band, and yellow marks the alpha band). Connections between pairs of regions composing the various patterns are presented by lines connecting two regions. Only regions involved in pair-patterns are connected by lines. The width of the connection line between two regions indicates the WI assigned to the respective connection. Thus, a thick line points to a strong connectivity between the two regions connected by the line.

Notice that the subset of electrodes locations and frequencies of activity comprising the patterns resemble those of the patterns before outlier removal (compare FIGS. 14A-B to the central panels of FIGS. 12 and 13, respectively). Nevertheless, the removal added 3 and 5 nodes to the active networks of the ADHD and Control groups, respectively. The addition of the nodes resulted from the more homogenous BNA pattern found in the refined core group. The network connectivity of the group patterns revealed a strong frontal-posterior network in the right hemisphere in the Control group (FIG. 14A) and a somewhat weaker and less extensive one in the ADHD group (FIG. 14B).

Classification and Correlation to Behavior

The classification of a novel subject as either ADHD or Control, based on the set of distinguishing patterns found for the ADHD and Control groups, is illustrated in the example presented in FIGS. 15A-F. FIG. 15A illustrates network connectivity of the most distinctive pattern in the Control group, excluding the Control subject to be classified (whose network activity is presented in FIGS. 15C-D). FIG. 15B illustrates the most distinctive pattern of the ADHD group, excluding the tested ADHD subject (whose network activity is presented in FIGS. 15E-F). FIGS. 15C-D illustrate the network connectivity of the tested Control subject for the Control group pattern and for the ADHD group pattern, respectively. FIGS. 15E-F illustrate the network connectivity of tested ADHD subject for the Control group pattern and for the ADHD group pattern, respectively. The line width format in FIGS. 15A-B is the same as in FIGS. 14A-B. The width of the connection line between two nodes in FIGS. 15C-F denotes the similarity of the subject's connection to that of both mother groups, as determined by computing the pair-pattern similarity measure for each pair in the pattern (the Sc computed for each pair of electrodes, times the WI of that electrode pair in the group pattern). A thick line indicates a connection which is highly similar to that of the group pattern. A line which appears in the group pattern but does not appear in the tested subject's pattern indicates that the corresponding pair did not exist in the single subject's activity. Node colors are the same as in FIGS. 14A-B.

Notice in FIGS. 15A-B that the excluded subjects are not the two outliers which were removed prior to this stage.

As shown in FIGS. 15C and 15F, there was a strong manifestation of the Control pattern in the activity of the tested Control subject (FIG. 15C) and of the ADHD pattern in the activity of the tested ADHD subject (FIG. 15F). As shown in FIGS. 15D and 15E, in both tested subjects, however, the electrode activity did not elicit a strong expression of the opposite group pattern. The classification of a single subject to a group was based upon this level of similarity to each of the patterns extracted for that group.

Table 1, below summarizes the classification results. The connectivity and the synchronicity-based classifications yielded a sensitivity of 84% (11 out of 13 ADHD subjects classified as such) and a specificity of 92% (12 out of 13

Control subjects were classified as non-ADHD), while the amplitude-based classification gave a sensitivity of 84% and a specificity of 76%.

TABLE 1

| Measure | Significance of difference between group means (p) | Specificity | Sensitivity |
|---|---|---|---|
| Connectivity | 0.005 | 92% | 4% |
| Synchronization | 0.004 | 92% | 84% |
| Amplitude | 0.009 | 76% | 84% |

Table 2 below summarizes Conners Adult ADHD Rating Scale (CAARS) and the BNA pattern based ADHD indices as calculated according to some embodiments of the present invention for each of the 13 Control and ADHD subjects.

TABLE 2

| | CAARS Inattentive Symptom Scale | CAARS Hyperactive/Impulsive Functions Scale | CAARS ADHD Symptoms Total Scale | BNA pattern based ADHD Index |
|---|---|---|---|---|
| Control | 63 | 46 | 54 | 29.56 |
| | 48 | 41 | 44 | −5.72 |
| | 72 | 56 | 68 | 2.21 |
| | 38 | 39 | 37 | −42.50 |
| | 38 | 35 | 31 | −33.36 |
| | 71 | 51 | 68 | 3.74 |
| | 53 | 52 | 53 | −14.54 |
| | 45 | 64 | 55 | −35.02 |
| | 53 | 46 | 51 | −29.71 |
| | 78 | 44 | 63 | −5.31 |
| | 51 | 48 | 49 | −6.26 |
| | 56 | 55 | 57 | −25.79 |
| | 59 | 44 | 52 | −21.34 |
| Mean | 55.77 | 47.77 | 52.46 | −14.16 |
| STD | 12.58 | 7.81 | 10.84 | 19.89 |
| ADHD | 88 | 74 | 88 | 24.21 |
| | 61 | 61 | 64 | 8.42 |
| | 79 | 86 | 89 | 25.35 |
| | 90 | 82 | 90 | 38.21 |
| | 78 | 72 | 80 | 11.31 |
| | 87 | 81 | 90 | 46.72 |
| | 90 | 72 | 90 | 36.59 |
| | 51 | 54 | 54 | −34.26 |
| | 90 | 76 | 90 | 8.26 |
| | 90 | 88 | 90 | −47.45 |
| | 60 | 73 | 69 | 5.98 |
| | 74 | 75 | 80 | 33.24 |
| | 80 | 73 | 81 | 9.77 |
| Mean | 78.31 | 74.38 | 81.15 | 12.80 |
| STD | 13.29 | 9.29 | 11.84 | 27.40 |

The results of Table 2 are presented in FIG. 16, which show correlation between the CAARS subscales and the BNA pattern based ADHD index of the present embodiments (denoted "BNA pattern score" in FIG. 16). The top, middle and bottom panels of FIG. 16 correspond to the shows correlation between the CAARS subscales for inattentive symptoms, hyperactivity/impulsive and total index, respectively. Green dots in FIG. 16 mark ADHD subjects and blue dots mark Control subjects. Outliers were automatically identified as described above. Correlation coefficients (r) and significance levels (p) are presented at the top of each panel (with and without outliers).

Significant correlations emerged between the inventive ADHD index and all three CAARS scores. The range of correlations was from about 0.51 to about 0.65 when all subjects were included, and from about 0.77 to about 0.87 when excluding automatically detected outliers. These results demonstrate that the BNA pattern comparison technique of the present embodiments is sensitive to different levels of ADHD when considered across a wide spectrum of the disorder, namely when both Control and ADHD subjects are included.

In is noted that the sensitivity of the technique of the present embodiments is not an artifact of combining two discontinuous groups (Control and ADHD) within which BNA pattern shows no relationship to CAARS. This is shown in FIG. 16 where the BNA-CAARS relationship is evident across the range of CAARS scores.

The results were also analyzed by dividing subjects on each of the CAARS scales into "high" and "low" based on a median split as follows: low inattentive (score ≤80), high inattentive (score ≥81), low hyperactive/impulsive (score ≤74), high hyperactive/impulsive (score ≥75), low CAARS total (score ≤88) and high CAARS total (score ≥89). Thereafter, descriptive statistics was computed for high/low groups using BNA pattern. Table 3 summarizes the descriptive statistics.

TABLE 3

| CAARS | | BNA pattern based ADHD Index | | | | | |
|---|---|---|---|---|---|---|---|
| Scale | Level | Mean | SD | Min | Median | Max | N |
| Inattentive Symptom | Low | 8.5 | 21.4 | −34.3 | 9.8 | 33.2 | 7 |
| | High | 17.8 | 34.6 | −47.5 | 30.4 | 46.7 | 6 |
| Hyperactive/ Impulsive Functions | Low | 8.9 | 21.9 | −34.3 | 9.8 | 36.6 | 7 |
| | High | 17.4 | 34.3 | −47.5 | 29.3 | 46.7 | 6 |
| CAARS ADHD Symptoms Total | Low | 8.4 | 21.2 | −34.3 | 9.8 | 33.2 | 7 |
| | High | 17.9 | 34.7 | −47.5 | 31.0 | 46.7 | 6 |

As shown in this statistical observation the mean BNA pattern in the "high" CAARS groups are about twice those in the "low," whereas for medians this ratio is about three.

Table 4 below summarizes the clinical evaluation scores (CGI-s, AISRS and ADHD-RS) and the BNA pattern based ADHD indices as calculated according to some embodiments of the present invention for each of the 15 subjects, except subject No. 13, of the additional ADHD group.

TABLE 4

| | CGI-S | Self RS total | AISRS total | BNA pattern Score |
|---|---|---|---|---|
| ADHD | 5 | 51 | 46 | −42.2 |
| | 4 | 50 | 31 | −1.7 |
| | 5 | 48 | 38 | 27.4 |
| | 5 | 48 | 35 | 4.4 |
| | 4 | 35 | 20 | 16.7 |
| | 5 | 66 | 46 | 6.5 |
| | 4 | 57 | 23 | 27.0 |
| | 6 | 54 | 48 | 86.2 |
| | 5 | 59 | 33 | 62.3 |
| | 4 | 41 | 24 | −49.3 |
| | 4 | 39 | 19 | −8.1 |
| | 5 | 50 | 42 | 23.1 |
| | | | | −4.8 |
| | 5 | 67 | 33 | −17.6 |
| | 5 | 43 | 40 | 70.5 |
| MEAN | 4.7 | 50.6 | 34.1 | 13.4 |
| STD | 0.6 | 9.5 | 9.8 | 38.3 |

The results were also analyzed by dividing subjects on each of the CGI-S and AISRS scores into "high" and "low" based on a median split as follows: low CGI-S (score=4), high CGI-S (score=5 or 6), low AISRS (score ≤34), high AISRS (score ≥35). Table 5 below summarizes descriptive statistics as computed for high/low groups using BNA pattern.

TABLE 5

| clinical evaluation | | BNA pattern based ADHD Index | | | | | |
|---|---|---|---|---|---|---|---|
| score | Level | Mean | SD | Min | Median | Max | N |
| CGI-S | Low | −3.1 | 29.4 | −49.3 | −1.7 | 27.0 | 5 |
| | High | 24.5 | 42.3 | −42.2 | 23.1 | 86.2 | 9 |
| AISRS | Low | 4.2 | 35.5 | −49.3 | −1.7 | 62.3 | 7 |
| | High | 25.1 | 43.0 | −42.2 | 23.1 | 86.2 | 7 |

As shown in this statistical observation the mean value of inventive BNA pattern based ADHD index is separated between the "low" and "high" group.

Conclusions

The study described in this example demonstrated the ability of the BNA pattern technique of the present embodiments to discriminate among varying levels of ADHD in addition to discriminating between ADHD and non-ADHD subjects. Such discrimination is optionally and preferably provided by means of likelihood values expressed as similarities between a subject-specific BNA pattern and a group BNA pattern. The likelihood values can be transmitted to a computer readable medium or displayed graphically or otherwise.

As demonstrated in this study, the present embodiments successfully provide such discrimination even for a relatively homogenous ADHD population, such as the population tested in this study. It is therefore concluded that the BNA pattern technique of the present embodiments can be utilized as an objective diagnostic tool for assessing the spectrum of ADHD severity.

Example 2

Use of BNA Pattern Comparison for Monitoring Neuro-Plasticity

Embodiments of the present embodiments were employed for monitoring of the physiological processes involved in natural and treatment-induced recovery (brain plasticity). The technique is useful for monitoring an individual stroke subject restoring his/her motor abilities by recruiting peri-lesional motor areas or by uncovering dormant neural pathways. Such monitoring can be noninvasive and can be utilized on a day-by-day bed-side basis.

Methods

The present study included 30 hemi-paresis subjects and 18 healthy subjects as a control group. 10 treatment sessions were conducted daily over 2 week period for each subject. For each subject, EEG data were collected using 64 scalp electrodes with BioSemi Active-Two system, and EMG data were collected using Extensors, Flexors & Biceps of both arms. Since not all subjects completed 10 treatment sessions, only 9 treatment sessions are presented in this example.

During each treatment session the following protocol was conducted:

(i) Pre-treatment evaluation: EEG and EMG recording during 30 hand activation of wrist dorsi-flexion repetitions of the impaired hand.

(ii) Treatment: Physiotherapy—Mirror Treatment:

(a) 60 repeats—non-paretic hand while observing the movement in a mirror; and (b) 30 repeats—both hands while observing the non-paretic hand in the mirror (iii) Post-treatment evaluation: EEG and EMG recordings during 30 hand activation of wrist dorsi-flexion repetitions of the impaired hand.

The control included EEG and EMG recordings during 30 hand activation of wrist dorsi-flexion repetitions of each hand.

The functional efficacy end point included hand/arm function by Fugl-Meyer (FM) test.

A group BNA pattern was constructed for the control group, and subject-specific BNA patterns were constructed for each subject (one BNA pattern per subject per treatment). Additionally, late stage BNA patterns were constructed for each subject based on EEG data collected during the last three days of treatment. All BNA patterns were constructed using the techniques described in Example 1 above.

Results

FIGS. 17A-B show a baseline BNA pattern (FIG. 17A) and an fMRI (FIG. 17B) which are characteristic to a healthy control hand activation. The fMRI was acquired 5-6 seconds post-activity and the BNA pattern was constructed based on data acquired during 1500 ms (from 500 ms before onset of auditory cue for movement onset, until 1000 ms following auditory cue). The color codes of the BNA pattern are: red nodes correspond to Delta waves, green nodes correspond to Theta waves, Yellow nodes correspond to Alpha waves and cyan nodes correspond to low Beta waves.

Following are case example results for one representative right-handed female hemi-paresis subject (age 48) with an impaired right arm/hand.

FIG. 18 is a conventional CT scan of the hemi-paresis subject following 9 treatment sessions. The CT scan shows lesion area on the left side of the brain (see white area in FIG. 18).

FIG. 19 shows the BNA pattern analysis of the subject. Shown in FIG. 19 are subject-specific BNA patterns as constructed for each of the 9 days, as well as the similarities between the subject-specific BNA patterns and the baseline BNA pattern of FIG. 17A. Also shown is a straight line (dotted) between the endpoints (diamonds) of the Fugl-Meyer efficacy score (FM=27 at day 1 and FM=46 at day 9). The percentage of these FM scored out of the maximal score ($FM_{max}$=66) are 41% and 70%, respectively.

Based on averaged data from days 7, 8 and 9, a late stage BNA pattern was constructed for this subject. The late stage BNA pattern is illustrated in FIG. 20 (color codes as above).

FIG. 21 shows the BNA pattern analysis of the subject, except that the subject-specific BNA pattern of a particular day was compared to the late stage BNA pattern instead of the group BNA pattern. Shown in FIG. 21 are BNA patterns of days 3 through 8. Format and values of the FM efficacy endpoints is the same as in FIG. 19.

Conclusions

The study described in this example demonstrated the ability of the BNA pattern technique of the present embodiments to monitor neuro-plasticity. Such monitoring is optionally and preferably performed by comparing a subject-specific BNA pattern to a group BNA pattern and/or a late stage BNA pattern of the same subject. The comparison can be quantitative by calculating similarity values between the respective BNA patterns, in which case the monitoring of neuro-plasticity can be expressed as a time-orders series of similarity values describing the “amount” of neuro-plasticity achieved as a function of the time. This time-orders series can be transmitted to a computer readable medium or displayed graphically or otherwise.

Example 3

Use of oBNA Pattern Comparison for Monitoring Acute Pain

Embodiments of the present embodiments were employed for extracting patterns characterizing high temp and low temp states, and to correlate brain patterns to pain intensity.

Methods

The present study included 14 healthy right-handed subjects. Each subject underwent heat stimulation applied to the left forearm at two temperature intensities: 35° C. (baseline temperature) and 52° C. (high temperature) at different sessions. Subjective numerical pain scores on a Visual Analog Scale (VAS) were collected after each stimulus.

ERP recordings from 31 electrodes were collected. The electrodes arrangement on the scalp is illustrated in FIG. 22. The symbols in FIG. 22 are according to the commonly used convention in EEG recording. Specifically, F denotes frontal lobe, T denotes temporal lobe, P denotes parietal lobe, O denotes occipital lobe, C denotes central lobe, and Z denotes the midline.

Two group BNA patterns (one BNA pattern for the baseline temperature and one BNA pattern for the high temperature), and several subject-specific BNA patterns (one BNA pattern per subject per session) were constructed according to the teachings of the present embodiments as described in Example 1 above.

The similarities between the subject-specific BNA pattern and the group BNA patterns were calculated as described in Example 1 above. For each subject, an objective pain index was defined as the similarity between the subject-specific BNA pattern and the group BNA pattern for the high temperature.

Results

FIGS. 23A and 23B show the group BNA patterns for the baseline and high temperatures, respectively. The color codes for the nodes and line format is as described in FIGS. 14A-B (Example 1) above. As shown, the group BNA pattern for the high temperature state is significantly higher from the group BNA pattern for the baseline temperature state in terms of both order and size of the BNA pattern. Representative examples of two subject-specific BNA patterns are provided in FIGS. 9A and 9B described above.

FIGS. 24A and 24B show representative examples of single electrode (located at the PZ location, see FIG. 22) activities for the high and baseline temperatures, respectively. Shown in FIGS. 24A-B are the individual activity of the electrode (top) and a time-running grand average of the activities (bottom). The upper panel in each FIGS. 24A-B has 18 rows, one for each subject. In each row, the subject’s non-normalized average activity for the duration of the recorded epoch is presented by a color scale, with blue being the extreme negative and red the extreme positive. The vertical lines in the top panels represent the minimal (left)

and maximal (right) latency limits of the electrode activity (note that the second blue line and the first red line overlap). Time segments bounding positive activity are marked in red, and time segments bounding negative activity are marked in blue. Dots represent positive (red) or negative (blue) peaks of activity which passed the z-score amplitude threshold within the time segment of the pattern for that subject.

FIG. 25 shows correlation between objective pain index and the subjective pain score on a Visual Analog Scale. The points marked by "A" and "B" correspond to the subject-specific BNA patterns shown in FIGS. 9A and 9B, respectively. The Pearson correlation coefficient is $r=0.9$, $p<0.001$.

An alternative approach to define the objective pain index is via a single parameter, e.g., the amplitude of a particular electrode.

FIG. 26 shows correlation between the amplitude of the CZ electrode and the subjective pain score on a Visual Analog Scale. The Pearson correlation coefficient in this case is $r=0.45$, $p>0.5$. Thus, the correlation between the objective pain index and the perception of pain level is higher with the BNA pattern comparison technique of the present embodiments than the single parameter analysis.

This example demonstrated that the BNA pattern comparison technique of the present embodiments can be used to identify significant distinguishing brain patterns between baseline and high heat induced pain with high sensitivity and specificity. This example also demonstrated that the BNA pattern comparison technique of the present embodiments can be used for calculating an objective pain index.

Conclusions

The study described in this example demonstrated the ability of the BNA pattern technique of the present embodiments to monitor pain. Such monitoring is optionally and preferably provided as an objective pain index expressed using a similarity value between a subject-specific BNA pattern and a group BNA pattern. This objective pain index can be transmitted to a computer readable medium or displayed graphically or otherwise.

Example 4

Use of BNA Pattern for Analyzing Pharmacologically Induced Memory Deficiency

Scopolamine has amnesiac properties in animals and humans. Its administration to healthy humans is known to induce certain symptoms similar to those observed in Alzheimer's disease. Scopolamine-induced memory deficiency is used as an experimental pharmacological model of the memory disorders observed in the course of this condition. Scopolamine reduces the capacity for acquisition, memorization and recall in a test of passive avoidance in rats. This involves measuring the reticence, after learning, that the animal has in entering a dark compartment, where it receives a mild electric shock. The administration of scopolamine suppresses this reticence, and the test compounds oppose the effect of scopolamine.

Embodiments of the present invention have been employed to analyze EEG data acquired from subjects administered with scopolamine.

Methods 15 adult subjects (12 males, 3 females, ages 37.6±5.6) participated in the study. All subjects were healthy volunteers.

All subjects were administered with Scopolamine 0.4 mg, and Saline serving as a placebo drug, on consecutive days, in a randomized order.

All subjects underwent auditory oddball target detection and working memory tests.

In the auditory oddball target detection test, the subjects were requested to respond to auditory target stimuli that occur infrequently and irregularly within a series of standard stimuli. The standard stimulus was in the form of a 1000 Hz tone, and the target stimulus was in the form of a 2000 Hz tone. The intervals between two successive stimuli (standard or target) were 1.5 seconds. Each subject was exposed to a series of stimuli, of which 80% were standard stimuli and 10% were target stimuli. The additional 10% were background sounds (referred to as "novel stimuli").

In the working memory test, each subject was requested to memorize an image of a human face (referred to as the "cue"). Two seconds later, the subject was again presented with an image of a human face (referred to as the "probe") and was asked to determine whether the probe matches the cue.

All subjects underwent EEG recordings during the tests. ERPs were recorded using 64 Ag—AgCl active electrodes (ActiveTwo, Biosemi) attached to the scalp by located according to the 10-20 international system, and filled with a conducting gel (Signa, Parker).

Potentials from the EEG channels were amplified, digitized at a rate of 256 Hz, and stored for off-line analysis.

Two group BNA patterns (one BNA pattern for the placebo group and one BNA pattern for the scopolamine group), and several subject-specific BNA patterns were constructed according to the teachings of the present embodiments as described in Example 1 above. The similarities between the subject-specific BNA pattern and the group BNA patterns were calculated as described in Example 1 above, except for the following provisions on data selection.

Two types of group BNA patterns were constructed in this example. A first type, referred to herein as a DIFF BNA pattern, described the activity that most differentiated between two groups or two conditions. In this type, data features that appeared in at least 11 subjects out of a maximum number of 15 subjects in one group, but a difference threshold (the number of subjects that had the pattern in one group minus the number of subjects that had the pattern in the other group) of 2 subjects, was used to construct the BNA pattern. In other words, the DIFF BNA pattern does not include the common features of the two groups. The SI quantities for this type of BNA patterns were calculated as described in Example 1 above.

A first type, referred to herein as an ALL BNA pattern, described the activity of a single group or condition, with no relation to other groups or conditions. The SI quantities for this type of BNA patterns were based on a fixed time-window (see $\Delta t_A$ and $\Delta t_B$ in FIG. 3A). The time windows was defined as mean±1.5*STD, where STD was the standard deviation of the group.

Results

Oddball Test

Patterns of electrode activity which distinguished the placebo group activity from the scopolamine group during the detection of the target stimuli were automatically revealed by the BNA pattern analysis of the present embodiments. These distinguishing patterns are referred to below as placebo patterns.

An example of a placebo pattern is presented in FIGS. 27A-D. Such pattern was observed in 12 subjects in the placebo group during detection of the target stimuli. This pattern thus had a group-subject value of 12. 4 scopolamine subjects fulfilled the complete set of requirements for this pattern, leading to a pattern differentiation level of 8.

This pattern involved electrodes: CP6, P2, P4, P6, P8, PO4, PO8 at Delta frequency.

Figure 27A:
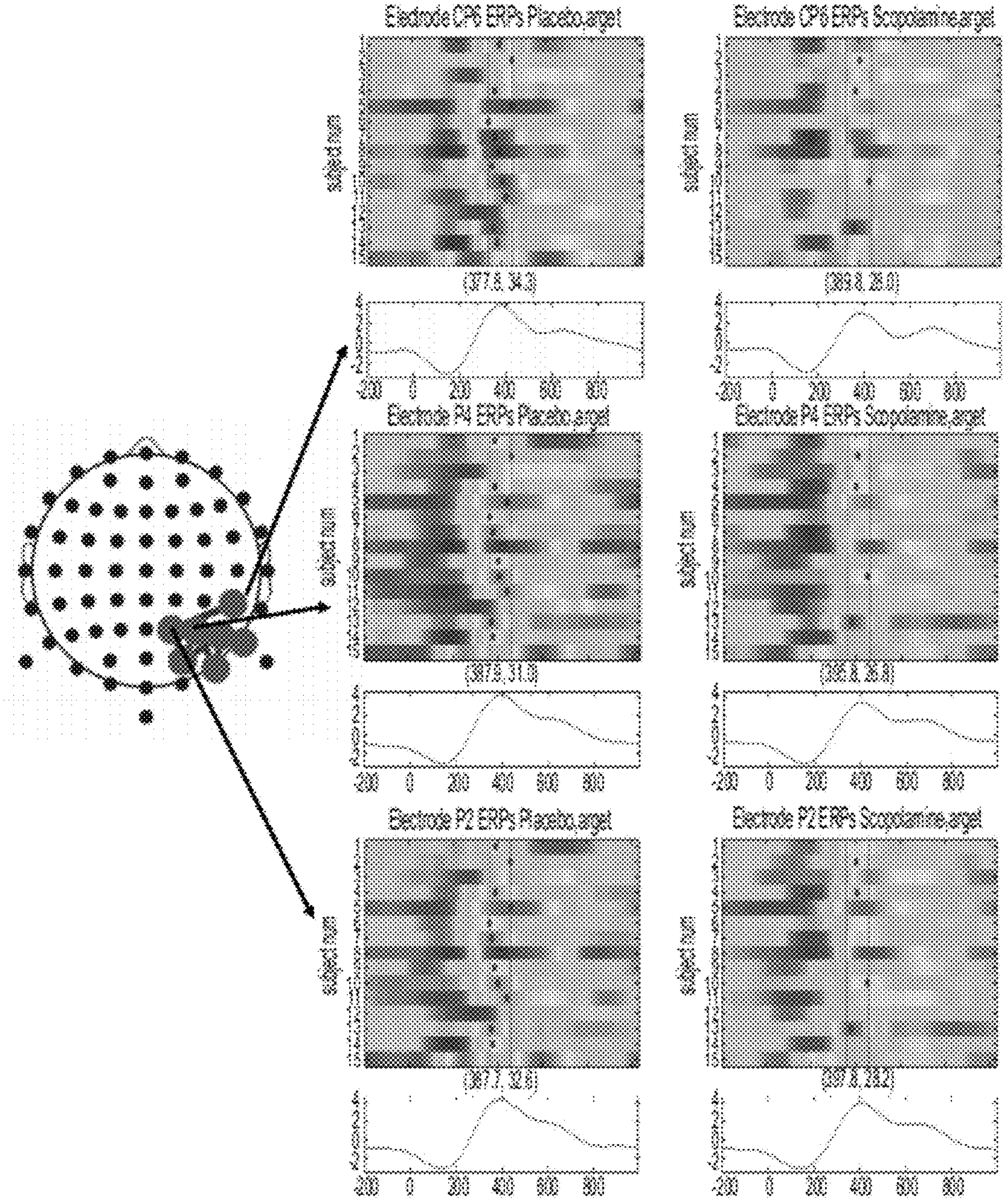
Figure 27B:
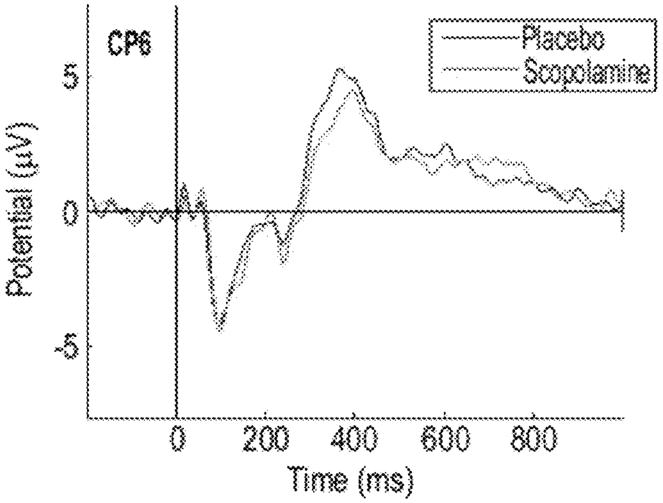
Figure 27C:
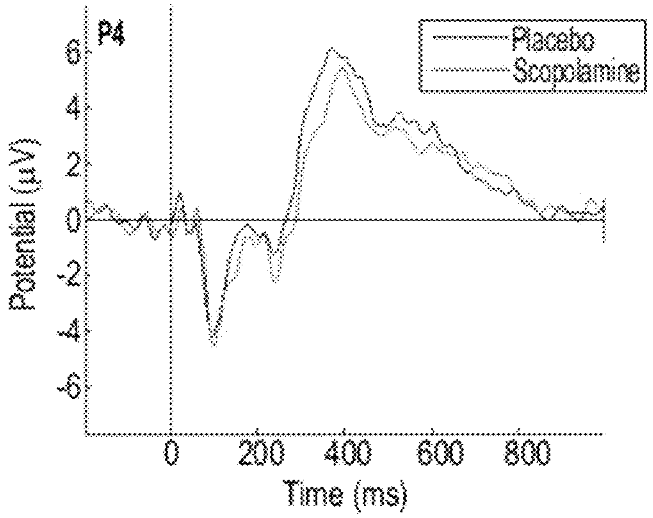
Figure 27D:
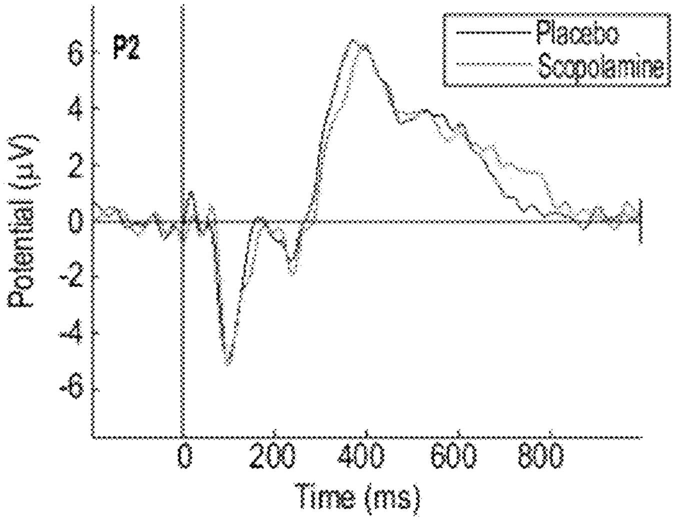

FIG. 27A shows the characteristic BNA pattern for this pattern (left column, top), and the characteristic activities in the CP6, P4 and P2 electrodes (first, second and third row, respectively), for the placebo (middle column) and scopolamine (right column) groups. FIGS. 27B-D show the ERPs (μV) as a function of time (ms) for the placebo (black curves) and scopolamine (red curves) groups measured by the CP6 (FIG. 27B), P4 (FIG. 27C) and P2 (FIG. 27D) electrodes.

The color codes of the BNA pattern shown in the right column of FIG. 27A are: red nodes correspond to Delta waves, green nodes correspond to Theta waves, Yellow nodes correspond to Alpha waves and cyan nodes correspond to low Beta waves. The width of the connection line between two nodes indicates the WI assigned to the respective connection, with thicker lines corresponding to higher WI values.

In the middle and right columns of FIG. 27A, the data for each group and each electrode are presented in a color panel and a graph. The graph shows the time-running grand average of the activities. The colored panel has 15 rows, one for each subject of the group. In each row, the subject's non-normalized average activity for the duration of the recorded epoch is presented by a color scale, with blue being the extreme negative and red the extreme positive. Vertical lines in the colored panels represent the minimal (left) and maximal (right) latency limits of the electrode activity within the pattern. Time segments bounding positive activity are marked in red, and time segments bounding negative activity are marked in blue. Dots represent positive (red) or negative (blue) peaks (not presented in this example) of activity which passed the z-score amplitude threshold within the time segment of the pattern for that subject. The mean and standard deviation of the peak-activity latencies (ms) within the bounds of the time segment(s) of all participating subjects are presented in parenthesis below the colored panels. Patterns of electrode activity which distinguished the scopolamine group activity from the placebo group during the detection of the target stimuli were also automatically revealed by the BNA pattern analysis of the present embodiments. These distinguishing patterns are referred to below as scopolamine patterns.

An example of a scopolamine pattern is presented in FIGS. 28A-C. Such pattern was observed in 12 subjects in the scopolamine group during the detection of the target stimuli. This pattern thus had a group-subject value of 12. 1 placebo subjects fulfilled the complete set of requirements for this pattern, leading to a pattern differentiation level of 11. This pattern involved electrodes: F4, FC2, FC4, FC5, FC6, FT8, C2, C4, C6, TP8 at Beta (12-18 Hz) frequency.

FIG. 28A shows the characteristic BNA pattern for this pattern (left column), and the characteristic activities in the FC6 and FC2 electrodes (first and second row, respectively), for the placebo (middle column) and scopolamine (right column) groups. FIGS. 28B-C show the ERPs as a function of time for the placebo and scopolamine groups measured by the FC6 and FC2 electrodes, respectively. Units, format of presentation and color codes are the same as in FIGS. 27A-D.

Patterns of electrode activity which distinguished the placebo group activity from the scopolamine group during the detection of the novel stimuli were automatically revealed by the BNA pattern analysis of the present embodiments. These distinguishing patterns are referred to below as placebo patterns.

An example of a placebo pattern is presented in FIGS. 29A-D. Such pattern was observed in 14 subjects in the placebo group during the detection of the novel stimuli. This pattern thus had a group-subject value of 14. 0 scopolamine subjects fulfilled the complete set of requirements for this pattern, leading to a pattern differentiation level of 14. This pattern involved electrodes: AF4, F1, F2, F4, F5, F6, F7, F8, Fz, FC1, FC2, FC3, FC4, FC5, FC6, FCz, FT7, FT8, C1, C2, C3, C4, C5, C6, Cz, T7, T8, CP1, CP2, CP4, CP5, CP6, CPz, TP7, P1, P2, P4, P5 at Delta frequency.

Figure 29A:
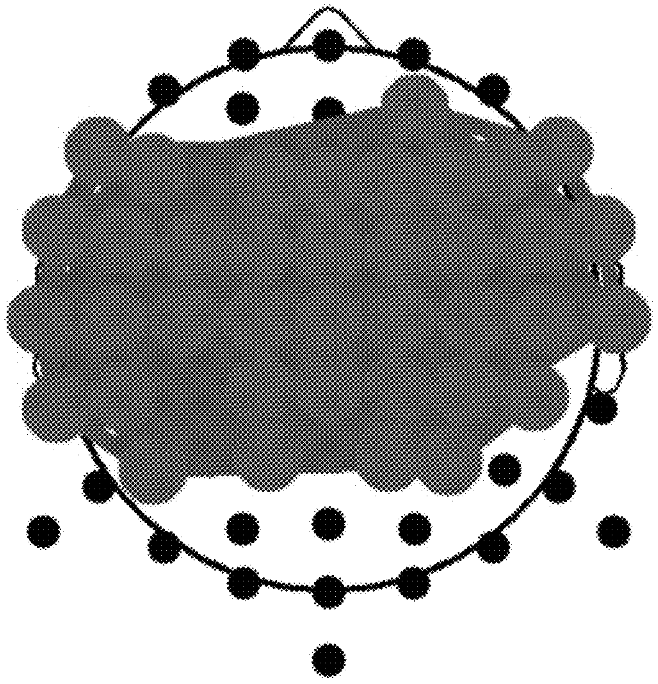
Figure 29B:
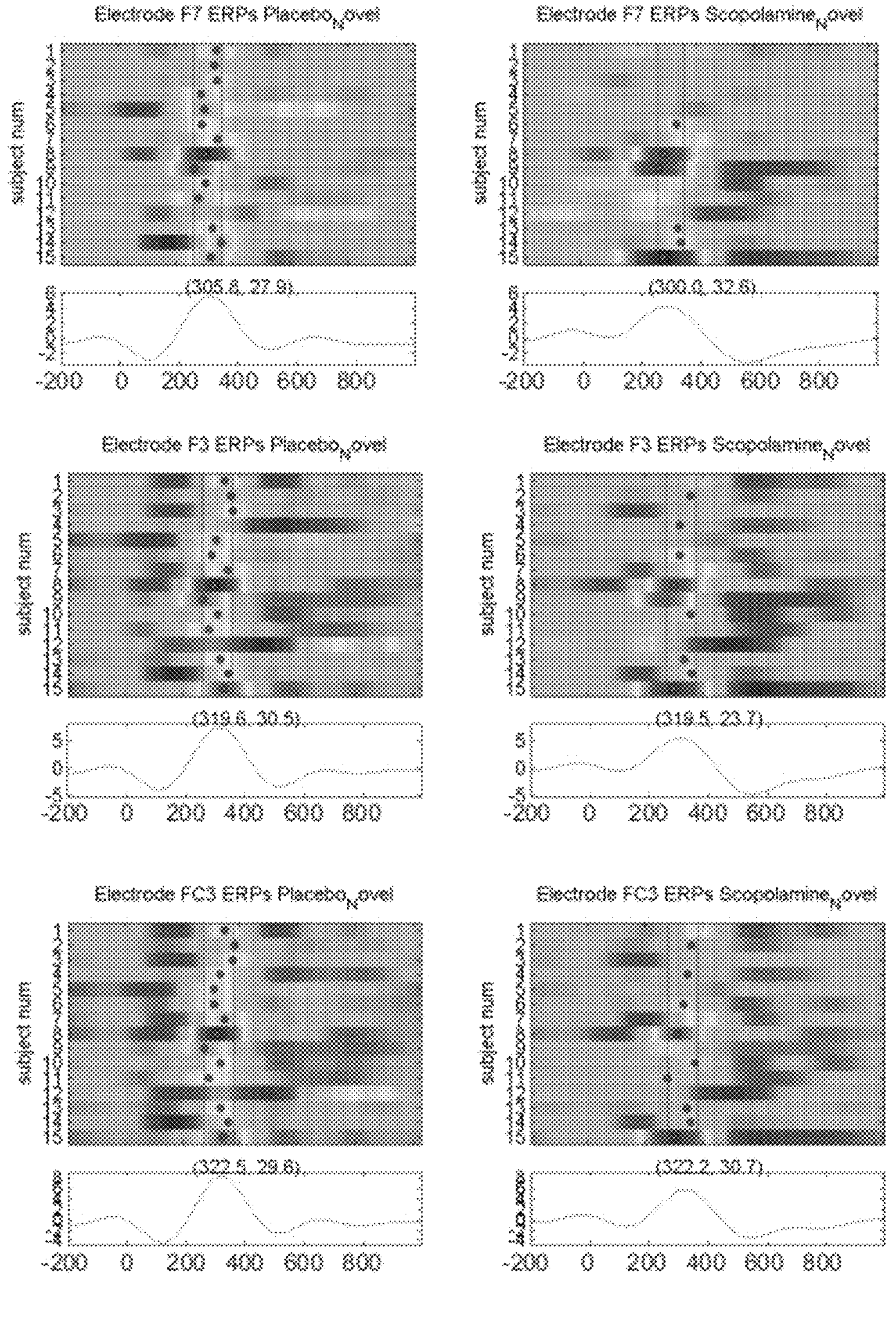
Figure 29C:
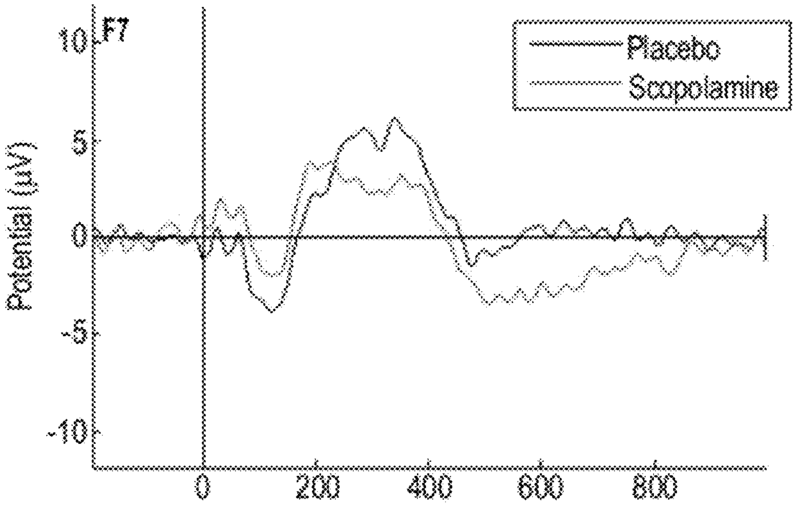
Figure 29D:
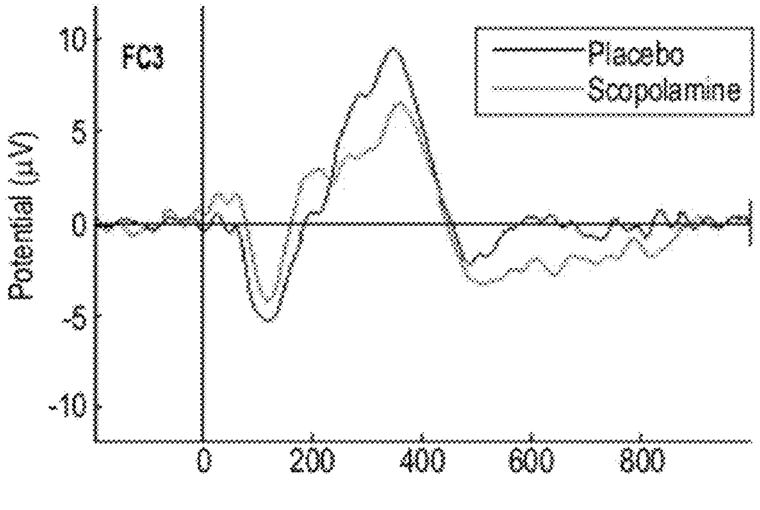

FIG. 29A shows the characteristic BNA pattern for this pattern, and FIG. 29B shows the characteristic activities in the F7, F3 and FC3 electrodes (first, second and third row, respectively), for the placebo (left column) and scopolamine (right column) groups. FIGS. 29C-D show the ERPs as a function of time for the placebo and scopolamine groups measured by the F7 and FC3 electrodes, respectively. Units, format of presentation and color codes are the same as in FIGS. 27A-D.

Working Memory Test

The BNA pattern analysis of the present embodiments successfully revealed distinguishing patterns of electrode activity both during the encoding process (namely while the subject was presented with the cue) and during the retrieval process (namely while the subject was presented with the probe).

FIGS. 10B and 30A-C present an example of a retrieval placebo DIFF BNA pattern. Such pattern was observed in 14 subjects in the placebo group during the retrieval process, and was therefore used for distinguishing this group. This pattern thus had a group-subject value of 14. One scopolamine subjects fulfilled the complete set of requirements for this pattern, leading to a pattern differentiation level of 13.

This pattern involved electrodes: F7, AF7, Fp1, Fpz, Fp2, AF8, F8, AF3, AFz, AF4, F1, Fz, F2, F6, F8, FCz, FC2, P9, P10, Iz at theta frequency and electrodes: Fp1, Fp2, AF4, PO7, PO8, P8, P10, Oz, O2, Iz at alpha frequency. FIG. 10B shows the characteristic BNA pattern for this pattern, and FIG. 30A shows the emergence of this pattern over time in five time points (110 ms, 150 ms, 170 ms, 206 ms and 292 ms after probe presentation). FIGS. 30B-C show the characteristic activities in the P8 electrode, for the placebo (FIG. 30B) and scopolamine (FIG. 30C) groups. Units, format of presentation and color codes are the same as in FIGS. 27A-D.

FIGS. 10D and 31A-E present an example of a retrieval scopolamine DIFF BNA pattern. Such pattern was observed in 15 subjects in the scopolamine group during the retrieval process, and was therefore used for distinguishing this group. This pattern thus had a group-subject value of 15. One placebo subjects fulfilled the complete set of requirements for this pattern, leading to a pattern differentiation level of 14.

Figure 31A:
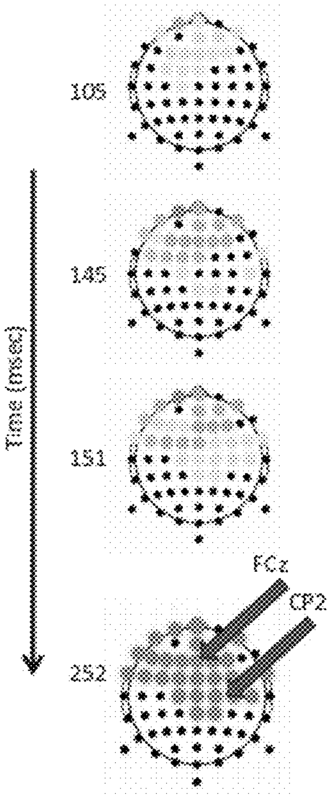
Figure 31B:
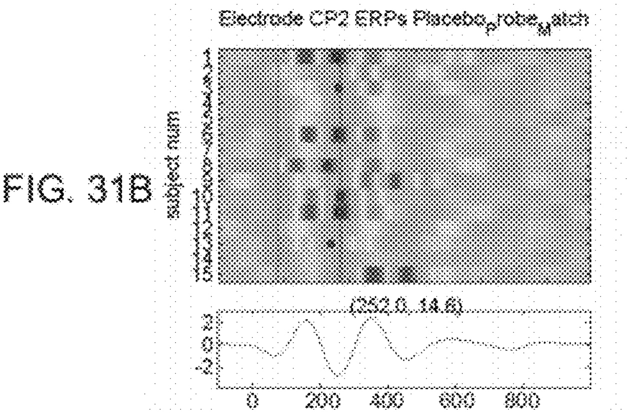
Figure 31C:
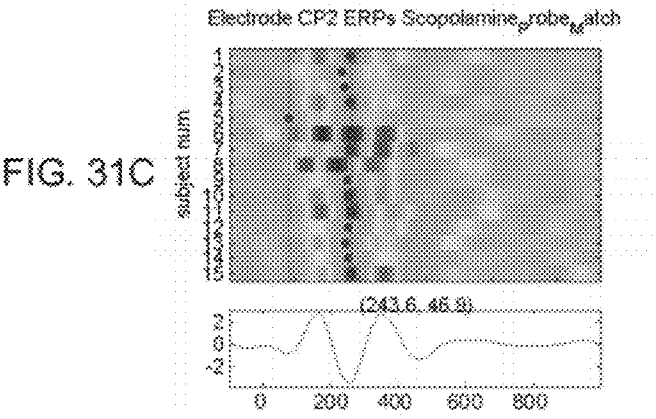
Figure 31D:
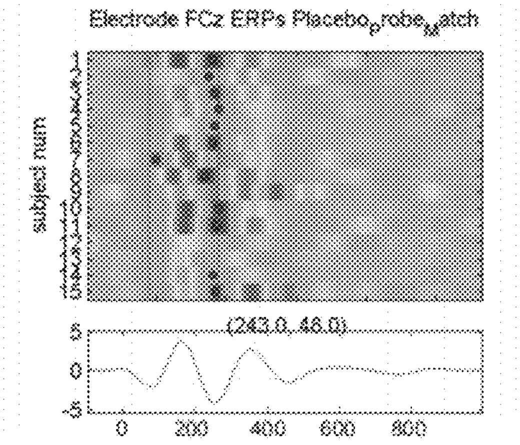
Figure 31E:
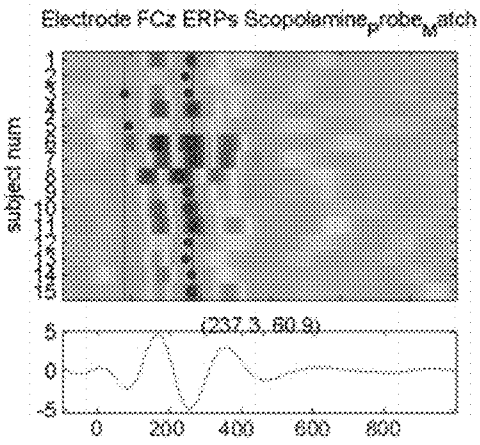

This pattern involved electrodes: Fp1, Fpz, AF7, AFz, AF4, AF8, Fz, F1, F2, F3, F4, F5, F7, FCz, FC1, FC2, FC3, FC4, FC5, FC6, FT7, FT8, Cz, C1, C2, C4, C6, CPz, CP2 at theta frequency. FIG. 10D shows the characteristic BNA pattern for this pattern, and FIG. 31A shows the emergence of this pattern over time in four time points (105 ms, 145 ms, 151 ms and 252 ms after probe presentation). FIGS. 31B-E show the characteristic activities in the CP2 (FIGS. 31B-C)

and FCZ (FIGS. 31D-E) electrodes, for the placebo (FIGS. 31B and 31D) and scopolamine (FIGS. 31C and 31E) groups. Units, format of presentation and color codes are the same as in FIGS. 27A-D.

FIGS. 10A, 32A-B, 33A-F and 34A-B present an example of an encoding placebo DIFF BNA pattern. Such pattern was observed in 13 subjects in the placebo group during the encoding process, and was therefore used for distinguishing this group. This pattern thus had a group-subject value of 13. Two scopolamine subjects fulfilled the complete set of requirements for this pattern, leading to a pattern differentiation level of 13−2=11. This pattern involved four nodes: IZ (latency about 166 ms, predominantly theta waves), P9 (latency about 170-175 ms, predominantly Alpha and theta waves), P10 (latency about 170-175 ms, predominantly alpha waves) and F6 (latency about 266 ms, predominantly theta waves). FIG. 10A shows the characteristic BNA pattern for this pattern. FIGS. 32A-B show the characteristic activities in the IZ electrode for the placebo (FIG. 32A) and scopolamine (FIG. 32B) groups. FIGS. 33A-D show the characteristic activities of theta waves (FIGS. 33A-B) and alpha waves (FIGS. 33C-D) in the P9 electrode for the placebo (FIGS. 33A and 33C) and scopolamine (FIGS. 33B and 33D) groups. FIGS. 33E-F show the characteristic activities in the P10 electrode for the placebo (FIG. 33E) and scopolamine (FIG. 33F) groups. FIGS. 34A-B show the characteristic activities in the F6 electrode for the placebo (FIG. 34A) and scopolamine (FIG. 34B) groups. Units, format of presentation and color codes are the same as in FIGS. 27A-D.

FIGS. 10C and 35A-B present an example of an encoding scopolamine DIFF BNA pattern. Such pattern was observed in 13 subjects in the scopolamine group during the encoding process, and was therefore used for distinguishing this group. This pattern thus had a group-subject value of 13. Three placebo subjects fulfilled the complete set of requirements for this pattern, leading to a pattern differentiation level of 1a−3=10. This pattern involved electrodes: Fp1, Fpz, Fp2, AF7, AF3, AFz, AF4, AF8, F2, F5, F7, Fz, FCz, FC1, FC2, FC3, FC4, Cz, C1, C2, C3, CP1, CP2, CP3, CP4, Pz, P2 at theta frequency. FIG. 10C shows the characteristic BNA pattern for this pattern, and FIGS. 35A-B show the characteristic activities in the F4 electrode for the placebo (FIG. 35A) and scopolamine (FIG. 35B) groups.

Results pertaining to BNA patterns of the ALL type are shown in FIGS. 41-43.

FIGS. 41A-D, show results obtained when a first group was defined as encoding placebo (namely, data were collected during the encoding process from subjects treated with placebo), and a second group was defined as retrieval placebo (namely, data were collected during the encoding process from subjects treated with placebo). FIG. 41A presents an example of an encoding placebo BNA pattern, and FIG. 41B presents an example of retrieval BNA pattern. The encoding placebo BNA pattern included electrodes Fpz, AF3, AFz, AF4, F1, Fz, F2, F4, F6, FC1, FCz, FC2, FC4, C5, C3, C1, Cz, C2, CP1, CPz, CP2, Iz, O2, PO8, P8, P9, P10 at theta frequency, electrodes: P9, P10 at alpha frequency, and electrode O1 at low beta frequency. Retrieval placebo BNA pattern included electrodes AF3, AFz, AF4, F3, F1, Fz, F2, F4, F6, F8, FC3, FC1, FCz, FC2, FC4, C1, Iz, P9, P10 at theta frequency, and electrodes Fpz, Fp2, AF4, F4, P9, P10, PO7 at alpha frequency. FIG. 41C shows an evolution of the encoding placebo (left column) and retrieval placebo (right column) BNA patterns, and FIG. 41D is a bar graph showing summarizing the characteristic BNA scores for these groups. The corresponding p value according to the Wilcoxon test was $3.05\times10^{-5}$.

Figure 42A:
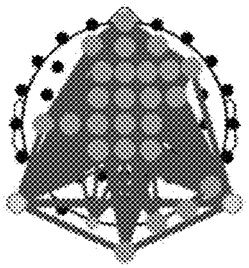
Figure 42B:
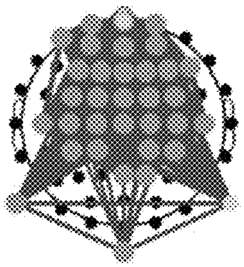
Figure 42C:
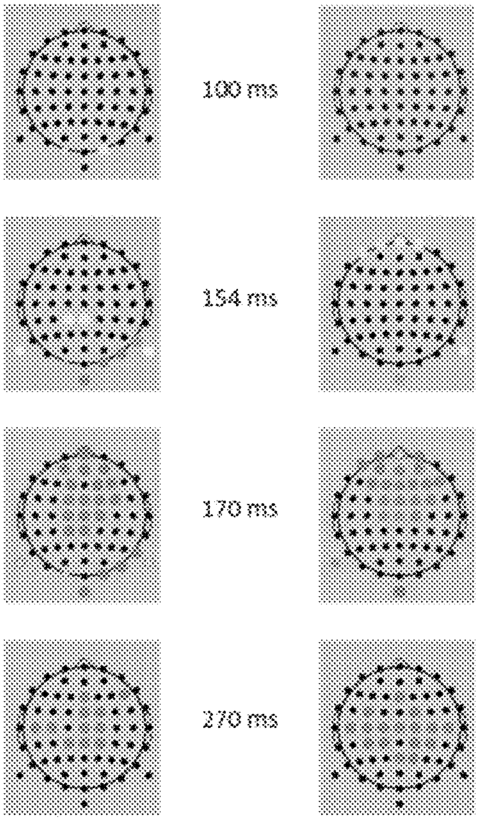
Figure 42D:
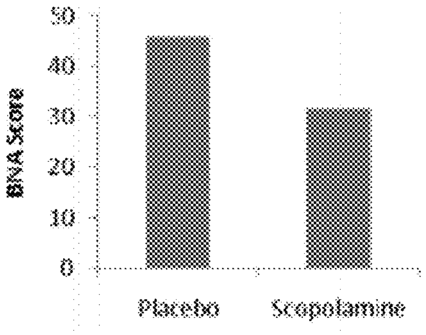

FIGS. 42A-D, show results obtained when a first group was defined as encoding placebo, and a second group was defined as encoding Scopolamine. FIG. 42A presents an example of an encoding placebo BNA pattern, and FIG. 42B presents an example of encoding Scopolamine BNA pattern. The encoding placebo BNA pattern included electrodes Fpz, AF3, AFz, AF4, F1, Fz, F2, F4, F6, FC1, FCz, FC2, FC4, C5, C3, C1, Cz, C2, CP1, CPz, CP2, Iz, O2, PO8, P8, P9, P10 at theta frequency, electrodes: P9, P10 at alpha frequency, and electrode O1 at low beta frequency. The encoding Scopolamine BNA pattern included electrodes Fp1, Fpz, Fp2, AF7, AF3, AFz, AF4, F3, F1, Fz, F2, F4, F6, FC3, FC1, FCz, FC2, FC4, C5, C3, C1, Cz, C2, C4, C6, CP3, CP1, CP2, CP4, Pz, P2, P9, Iz at theta frequency, and electrodes Fpz and P9 at alpha frequency. FIG. 42C shows an evolution of the encoding placebo (left column) and encoding Scopolamine (right column) BNA patterns, and FIG. 42D is a bar graph showing summarizing the characteristic BNA scores for these groups. The corresponding p value according to the Wilcoxon test was $9.16\times10^{-5}$.

FIGS. 43A-D, show results obtained when a first group was defined as retrieval placebo, and a second group was defined as retrieval Scopolamine. FIG. 43A presents an example of an retrieval placebo BNA pattern, and FIG. 43B presents an example of retrieval Scopolamine BNA pattern. The retrieval placebo BNA pattern included electrodes AF3, AFz, AF4, F3, F1, Fz, F2, F4, F6, F8, FC3, FC1, FCz, FC2, FC4, C1, Iz, P9, P10 at theta frequency, and electrodes Fpz, Fp2, AF4, F4, P9, P10, PO7 at alpha frequency. The retrieval Scopolamine BNA pattern included electrodes Fpz, AFz, F1, Fz, F2, F4, F8, FC3, FCz, FC2, FC4, FT8, C1, Cz, C2, C4, C6, CPz, CP2, Oz, O2, PO8, P9, P10 at theta frequency and electrodes Fp1, Fpz, Fp2, P9, PO7, O1, Oz, Iz, O2, PO4, PO8, P8, P10 at alpha frequency. FIG. 43C shows an evolution of the retrieval placebo (left column) and retrieval Scopolamine (right column) BNA patterns, and FIG. 43D is a bar graph showing summarizing the characteristic BNA scores for these groups. The corresponding p value according to the Wilcoxon test was $3.05\times10^{-5}$.

Conclusions

Although the above example concerns with analysis of pharmacologically induced memory deficiency, it is recognized by the present inventors that the BNA pattern technique of the present embodiments can also be used for analyzing induced memory deficiency, even when not induced by a pharmacological or other intervention. The study described in this example demonstrated the ability of the BNA pattern technique of the present embodiments to discriminate among varying levels of induced memory deficiency. Such discrimination is optionally and preferably provided by means of likelihood values expressed as similarities between a subject-specific BNA pattern and a group BNA pattern. The likelihood values can be transmitted to a computer readable medium or displayed graphically or otherwise.

Example 5

BNA Pattern of Subjects with Mild Cognitive Impairment and Alzheimer's Disease Alzheimer's disease (AD) is the most widespread progressive degenerative disease in the elderly population.

Symptomatic treatment of this disease is provided by acetylcholinesterase inhibitors, e.g., tacrine, donepezil, rivastigmine and galantamine. It is recognized, however, that the therapeutic benefits obtained are modest at the very mode. Since effective therapeutic strategies against AD are limited, the discovery of new treatments using molecules with a different mode of action to that of the molecules currently available in clinical practice and capable of treating or delaying the progression of the disease is therefore desirable.

Diagnosticians have long sought a means to definitively identify AD during the lifetime of demented patients, as opposed to histopathological examination of brain tissue, which is the only present means available for rendering an ultimate diagnosis of AD. AD is the most common form of dementia. Early on, patients complaining of slight memory loss and confusion are characterized as suffering from mild cognitive impairment (MCI), which in some instances advances to the classical symptoms of Alzheimer's disease resulting in severe impairment of intellectual and social abilities.

Adding to the controversy surrounding AD and its diagnosis, is the problem of discerning AD patients from those suffering from other forms of cognitive decline, particularly decline which is broadly characterized as MCI. Such decline is insidious in that it often is diagnosed with only transient symptoms of memory loss or confusion, wherein cognitive abilities have not diminished to a point where they are indicated as a reduction in performance on tests such as the Mini Mental State Examination (MMSE) and thus are often dismissed and under-treated.

The diagnosis of MCI is difficult. The term "mild cognitive impairment" has been coined to describe a condition that may or may not eventually lead to dementia. Some studies have shown that patients with MCI had a more rapid decline in cognitive function than control patients, but a less rapid decline than patients with mild Alzheimer's disease.

MCI, while being characterized as a condition associated with mild recent memory loss without dementia or significant impairment of other cognitive functions to an extent that is beyond that expected for age or educational background, nevertheless progresses to AD in many patients. While figures vary as to the number of individuals with MCI who go on to develop AD, a number frequently seen in the literature is that up to about 40% of patients diagnosed with MCI will develop AD in about three years time.

Embodiments of the present invention have been employed to analyze EEG data acquired from subjects suffering from MCI and subjects suffering from AD.

Methods 14 adult subjects participated in the study. 7 subjects were diagnosed with AD and 7 subjects were diagnosed with MCI.

All subjects underwent auditory oddball target detection test. Recording of cognitive ERPs was done according to the auditory oddball paradigm. Patients lay down on an examination bed, with eyes opened, in a soundproof, darkened room. Tones (60 dB SPL, 100-ms duration) were presented binaurally through a headset up to a total of 150 stimuli. Patients were instructed to identify the odd 2000 Hz high-pitched stimuli (target sounds), which had a 20% occurrence probability among the standard 1000 Hz low-pitched stimuli (common sounds). The cognitive task required paying attention to the odd stimuli and counting them. The stimulus order of appearance was random and there was at least a 1140-ms gap between each stimulus. Three tests were recorded with a 2-minute pause followed by repeated instructions. The test was stopped once the 90 target stimuli have been played out and the patient was asked to give out his/her count of the oddest sounds.

Electrical brain activities were recorded from four scalp derivations (frontal: Fz, central: Cz, parietal: Pz, occipital: Oz) according to the international 10/20 standards, with, as a reference, two linked electrodes attached to the right and left earlobes (A1-A2). Impedances were less than 5 KΩ. EEG activities (sampling rate of 512 Hz) were amplified with a 40,000 gain, processed with band pass filters of 0.5 to 150 Hz and visualized on the screen of an ERP machine. The recording started 100 ms before the stimulation to serve as a baseline and kept going 900 ms after that. The EEG sequences distorted by ocular movements were automatically rejected.

Two group BNA patterns were constructed according to the teachings of the present embodiments as described in Example 1 above. One group BNA pattern was constructed using data acquired from the AD group, and the other BNA pattern was constructed using data acquired from the MCI group.

Results

The BNA pattern analysis of the present embodiments successfully revealed distinguishing patterns of electrode activity.

FIGS. 36A-C present an example of an AD pattern. Such pattern was observed in all subjects in the AD group, and was therefore used for distinguishing this group. This pattern thus had a group-subject value of 7. 0 MCI subjects fulfilled the complete set of requirements for this pattern, leading to a pattern differentiation level of 7. This pattern involved parietal and occipital electrodes (Pz and Oz respectively) in the delta, theta an alpha frequency bands. FIG. 36A shows the characteristic BNA pattern for this pattern, and FIGS. 36B-C show the characteristic activities in the Oz electrode, for the AD (FIG. 36B) and MCI (FIG. 36C) groups. Units, format of presentation and color codes are the same as in FIGS. 27A-D.

FIGS. 37A-C present an example of an MCI pattern. Such pattern was observed in all subjects in the MCI group, and was therefore used for distinguishing this group. This pattern thus had a group-subject value of 7. 0 AD subjects fulfilled the complete set of requirements for this pattern, leading to a pattern differentiation level of 7. This pattern involved electrodes Oz, Pz, Cz and Fz, in the delta, theta and alpha frequency bands. FIG. 37A shows the characteristic BNA pattern for this pattern, and FIGS. 37B-C show the characteristic activities in the Oz electrode, for the AD (FIG. 37B) and MCI (FIG. 37C) groups. Units, format of presentation and color codes are the same as in FIGS. 27A-D.

As shown in FIGS. 36A and 37B there is a significant difference between the characteristic patterns of AD and MCI, which are manifested by the respective BNA patterns for these groups. Thus, this Example demonstrates that the BNA pattern comparison technique of the present embodiments can be used to assess, for a particular subject, whether the likelihood for AD is higher or lower than MCI.

Conclusions

The BNA pattern technique of the present embodiments can discriminate AD subjects from MCI subjects as well as among varying levels of AD and/or MCI. Such discrimination can optionally and preferably be provided by means of likelihood values expressed as similarities between a subject-specific BNA pattern and a group BNA pattern. The likelihood values can be transmitted to a computer readable medium or displayed graphically or otherwise.

While the above example concerns with AD and MCI, it is recognized by the present inventors that the BNA pattern comparison technique of the present embodiments is useful also for distinguishing between many types of cognitive disorders, including, without limitation, mild cognitive disorder, age-associated cognitive decline and MCI.

REFERENCES

Association A P. Diagnostic and statistical manual of mental disorders. (4th Text Revision ed.) Washington, D.C. 2000.

Alexander D M, Hermens D F, Keage H A, Clark C R, Williams L M, Kohn M R, et al. Event-related wave activity in the EEG provides new marker of ADHD. Clin Neurophysiol 2008; 119:163-179.

Alexander D M, Trengove C, Wright J J, Boord P R, Gordon E. Measurement of phase gradients in the EEG. J Neurosci Methods 2006; 156:111-128.

Ashtari M, Kumra S, Bhaskar S L, Clarke T, Thaden E, Cervellione K L, et al. Attention-deficit/hyperactivity disorder: a preliminary diffusion tensor imaging study. Biol Psychiatry 2005; 57:448-455.

Barkley R A. Behavioral inhibition, sustained attention, and executive functions: constructing a unifying theory of ADHD. Psychol Bull 1997; 121:65-94.

Barry R J, Clarke A R, Johnstone S J. A review of electrophysiology in attention-deficit/hyperactivity disorder: I. Qualitative and quantitative electroencephalography. Clin Neurophysiol 2003; 114:171-183.

Barry R J, Johnstone S J, Clarke A R. A review of electrophysiology in attention-deficit/hyperactivity disorder: II. Event-related potentials. Clin Neurophysiol 2003; 114: 184-198.

Basar E, Basar-Eroglu C, Karakas S, Schurmann M. Gamma, alpha, delta, and theta oscillations govern cognitive processes. Int J Psychophysiol 2001; 39:241-248.

Basar-Eroglu C, Basar E, Demiralp T, Schurmann M. P30000-response: possible psychophysiological correlates in delta and theta frequency channels. A review. Int J Psychophysiol 1992; 13:161-179.

Bassett D S, Bullmore E. Small-world brain networks. Neuroscientist 2006; 12:512-23.

Bassett D S, Bullmore E, Verchinski B A, Mattay V S, Weinberger D R, Meyer-Lindenberg A. Hierarchical organization of human cortical networks in health and schizophrenia. J Neurosci 2008; 28:9239-9248.

Bokura H, Yamaguchi S, Kobayashi S. Electrophysiological correlates for response inhibition in a Go/NoGo task. Clin Neurophysiol 2001; 112:2224-2232.

Bullmore E, Sporns O. Complex brain networks: graph theoretical analysis of structural and functional systems. Nat Rev Neurosci 2009; 10:186-198.

Buzsaki G, Draguhn A. Neuronal oscillations in cortical networks. Science 2004; 304:1926-1929.

Cao F, Ester M, Qian W, Zhou A. Density-based clustering over an evolving data stream with noise. Proceedings of the Sixth SIAM International Conference on Data Mining Bethesda, Md.; 2006; p. 328-39.

Castellanos F X, Margulies D S, Kelly C, Uddin L Q, Ghaffari M, Kirsch A, et al. Cingulate-precuneus interactions: a new locus of dysfunction in adult attention-deficit/hyperactivity disorder. Biol Psychiatry 2008; 63:332-337.

Castellanos F X, Sonuga-Barke E J, Milham M P, Tannock R. Characterizing cognition in ADHD: beyond executive dysfunction. Trends Cogn Sci 2006; 10:117-123.

Clark L, Blackwell A D, Aron A R, Turner D C, Dowson J, Robbins T W, et al. Association between response inhibition and working memory in adult ADHD: a link to right frontal cortex pathology? Biol Psychiatry 2007; 61:1395-1401.

Corbetta M, Shulman G L. Control of goal-directed and stimulus-driven attention in the brain. Nat Rev Neurosci 2002; 3:201-215.

De Vico Fallani F, Astolfi L, Cincotti F, Mattia D, Tocci A, Salinari S, et al. Brain network analysis from high-resolution EEG recordings by the application of theoretical graph indexes. IEEE Trans Neural Syst Rehabil Eng 2008; 16:442-452.

Dickstein S G, Bannon K, Castellanos F X, Milham M P. The neural correlates of attention deficit hyperactivity disorder: an ALE meta-analysis. J Child Psychol Psychiatry 2006; 47:1051-1062.

Eldawlatly S, Jin R, Oweiss K G. Identifying functional connectivity in large-scale neural ensemble recordings: a multiscale data mining approach. Neural Comput 2009; 21:450-477.

Engel A K, Fries P, Singer W. Dynamic predictions: oscillations and synchrony in top-down processing. Nat Rev Neurosci 2001; 2:704-716.

Feldt S, Waddell J, Hetrick V L, Berke J D, Zochowski M. Functional clustering algorithm for the analysis of dynamic network data. Phys Rev E Stat Nonlin Soft Matter Phys 2009; 79:056104 (19 pp.).

Frank M J, Santamaria A, O'Reilly R C, Willcutt E. Testing computational models of dopamine and noradrenaline dysfunction in attention deficit/hyperactivity disorder. Neuropsychopharmacology 2007; 32:1583-1599.

Fries P. A mechanism for cognitive dynamics: neuronal communication through neuronal coherence. Trends Cogn Sci 2005; 9:474-480.

Garavan H, Ross T J, Murphy K, Roche R A, Stein E A. Dissociable executive functions in the dynamic control of behavior: inhibition, error detection, and correction. Neuroimage 200; 17:1820-1829.

Geva A B. Bioelectric sources estimation using spatio-temporal matching pursuit. Appl Sig Proces 1998; 5:195-208.

Guy W: ECDEU Assessment Manual for Psychopharmacology revised. Bethesda, Md.: United States Department of Health, Education, and Welfare (1976).

Haig A R, Gordon E, Rogers G, Anderson J. Classification of single-trial ERP sub-types: application of globally optimal vector quantization using simulated annealing. Electroencephalogr Clin Neurophysiol 1995; 94:288-297.

Harmony T, Fernandez T, Silva J, Bernal J, Diaz-Comas L, Reyes A, et al. EEG delta activity: an indicator of attention to internal processing during performance of mental tasks. Int J Psychophysiol 1996; 24:161-171.

Hill D E, Yeo R A, Campbell R A, Hart B, Vigil J, Brooks W. Magnetic resonance imaging correlates of attention-deficit/hyperactivity disorder in children. Neuropsychology 2003; 17:496-506.

Huang Y, Erdogmus D, Mathan S, Pavel M. A fusion approach for image triage using single trial ERP detection. CNE 2007 3rd International IEEE/EMBS Conference on Neural Engineering 2007; p. 473-476.

Hynd G W, Semrud-Clikeman M, Lorys A R, Novey E S, Eliopulos D, Lyytinen H. Corpus callosum morphology in attention deficit-hyperactivity disorder: morphometric analysis of MRI. J Learn Disabil 1991; 24:141-146.
Johnstone S J, Barry R J, Anderson J W. Topographic distribution and developmental timecourse of auditory event-related potentials in two subtypes of attention-deficit hyperactivity disorder. Int J Psychophysiol 2001; 42:73-94.
Johnstone S J, Barry R J, Dimoska A. Event-related slow-wave activity in two subtypes of attention-deficit/hyperactivity disorder. Clin Neurophysiol 2003; 114:504-514.
Johnstone S J, Dimoska A, Smith J L, Barry R J, Pleffer C B, Chiswick D, et al. The development of stop-signal and Go/Nogo response inhibition in children aged 7-12 years: performance and event-related potential indices. Int J Psychophysiol 2007; 63:25-38.
Jung T P, Makeig S, Westerfield M, Townsend J, Courchesne E, Sejnowski T J. Analysis and visualization of single-trial event-related potentials. Hum Brain Mapp 2001; 14:166-185.
Karakas S, Erzengin O U, Basar E. The genesis of human event-related responses explained through the theory of oscillatory neural assemblies. Neurosci Lett. 2000 5; 285:45-48.
Kessler R C, Adler L, Barkley R, Biederman J, Conners C K, Demler O, et al. The prevalence and correlates of adult ADHD in the United States: results from the National Comorbidity Survey Replication. Am J Psychiatry 2006; 163:716-723.
Klimesch W. EEG alpha and theta oscillations reflect cognitive and memory performance: a review and analysis. Brain Res Brain Res Rev 1999; 29:169-195.
Krieger S, Timmer J, L is S, Olbrich H M. Some considerations on estimating event-related brain signals. J Neural Transm Gen Sect 1995; 99:103-129.
Liddle P F, Kiehl K A, Smith A M. Event-related fMRI study of response inhibition. Hum Brain Mapp 2001; 12:100-109.
Liu Y, Liang M, Zhou Y, He Y, Hao Y, Song M, et al. Disrupted small-world networks in schizophrenia. Brain. 2008; 131 (Pt 4):945-961.
Makeig S, Bell A J, Jung T P, Sejnowski T J. Independent component analysis of electroencephalographic data. Advances in Neural Information Processing Systems. 1996; 8:145-151.
Matousek M, Petersen I. Automatic evaluation of EEG background activity by means of age-dependent EEG quotients. Electroencephalogr Clin Neurophysiol 1973; 35:603-612.
Melloni L, Molina C, Pena M, Tones D, Singer W, Rodriguez E. Synchronization of neural activity across cortical areas correlates with conscious perception. J. Neurosci. 2007 14; 27:2858-2865.
Michel C M, Murray M M., Lantz G, Gonzalez S, Spinelli L, Grave de Peralta R. EEG source imaging. Clin Neurophysiol 2004; 115:2195-2222.
Murias M, Swanson J M, Srinivasan R. Functional connectivity of frontal cortex in healthy and ADHD children reflected in EEG coherence. Cereb Cortex 2007; 17:1788-1799.
Murphy K R, Adler L A. Assessing attention-deficit/hyperactivity disorder in adults: focus on rating scales. J Clin Psychiatry 2004; 65 Suppl 3:12-17.
Parra L C, Spence C D, Gerson A D, Sajda P. Recipes for the linear analysis of EEG. Neuroimage 2005; 28:326-341.
Pascual-Marqui R D, Esslen M, Kochi K, Lehmann D. Functional imaging with low-resolution brain electromagnetic tomography (LORETA): a review. Methods Find Exp Clin Pharmacol 2002; 24 Suppl C:91-95.
Pliszka S R, Liotti M, Woldorff M G Inhibitory control in children with attention-deficit/hyperactivity disorder: event-related potentials identify the processing component and timing of an impaired right-frontal response-inhibition mechanism. Biol Psychiatry 2000; 48:238-246.
Posner M I, Rothbart M K. Research on attention networks as a model for the integration of psychological science. Annu Rev Psychol 2007; 58:1-23.
Santosh M, Deniz E, Yonghong H, Misha P, Patricia V, James C, et al. Rapid image analysis using neural signals. CHI '08 extended abstracts on human factors in computing systems. Florence, Italy: ACM 2008.
Satterfield J H, Schell A M, Backs R W, Hidaka K C. A cross-sectional and longitudinal study of age effects of electrophysiological measures in hyperactive and normal children. Biol Psychiatry 1984; 19:973-990.
Sekihara K, Nagarajan S S, Poeppel D, Marant A and Miyashita Y. Reconstructing spatio-temporal activities of neural sources using an MEG vector beamformer technique. IEEE Trans Biomed Engin 2001; 48:760-771.
Semrud-Clikeman M, Filipek P A, Biederman J, Steingard R, Kennedy D, Renshaw P, et al. Attention-deficit hyperactivity disorder: magnetic resonance imaging morphometric analysis of the corpus callosum. J Am Acad Child Adolesc Psychiatry 1994; 33:875-881.
Smith A B, Taylor E, Brammer M, Toone B, Rubia K. Task-specific hypoactivation in prefrontal and temporoparietal brain regions during motor inhibition and task switching in medication-naive children and adolescents with attention deficit hyperactivity disorder. Am J Psychiatry 2006; 163:1044-1051.
Smith J L, Johnstone S J, Barry R J Inhibitory processing during the Go/NoGo task: an ERP analysis of children with attention-deficit/hyperactivity disorder. Clin Neurophysiol 2004; 115:1320-1331.
Sonuga-Barke E J. The dual pathway model of AD/HD: an elaboration of neuro-developmental characteristics. Neurosci Biobehav Rev 2003; 27:593-604.
Spencer T et al. Diagnostic approaches to adult ADHD. Prim Psychiatry 2004. 11:49-56.
Stam C J, Jones B F, Nolte G, Breakspear M, Scheltens P. Small-world networks and functional connectivity in Alzheimer's disease. Cereb Cortex 2007; 17:92-99.
Supekar K, Menon V, Rubin D, Musen M, Greicius M D. Network analysis of intrinsic functional brain connectivity in Alzheimer's disease. PLoS Comput Biol 2008; 4:e1000100.
Tian L, Jiang T, Wang Y, Zang Y, He Y, Liang M, et al. Altered resting-state functional connectivity patterns of anterior cingulate cortex in adolescents with attention deficit hyperactivity disorder. Neurosci Lett 2006; 400: 39-43.
Wang L, Zhu C, He Y, Zang Y, Cao Q, Zhang H, et al. Altered small-world brain functional networks in children with attention-deficit/hyperactivity disorder. Hum Brain Mapp 2009; 30:638-649.
Wigfield A, Eccles J S, Schiefele U, Roeser R, Davis-Kean P. Development of achievement motivation. In: Damon W and Lerner R M, editors. Handbook of child psychology: Vol. 3. Social, emotional and personality development. Hoboken, N.J.: Wiley; 2006. p. 993-1002.
Wodka E L, Mahone E M, Blankner J G, Larson J C, Fotedar S, Denckla M B, et al. Evidence that response inhibition is a primary deficit in ADHD. J Clin Exp Neuropsychol 2007; 29:345-356.

Womelsdorf T, Schoffelen J M, Oostenveld R, Singer W, Desimone R, Engel A K, et al. Modulation of neuronal interactions through neuronal synchronization. Science 2007; 316:1609-1612.

Yabe H, Saito F, Fukushima Y. Median method for detecting endogenous event-related brain potentials. Electroencephalogr Clin Neurophysiol 1993; 87:403-407.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of diagnosing and treating a brain related disorder or condition, the method comprising:

operating a measuring device placed on a scalp of a subject for collecting neurophysiological data from a brain of the subject; and operating a data processor for:

determining activity-related features in the data by identifying patterns of peaks in the data, and expressing each activity-related feature as a vector of data characteristics;

clustering said vectors to provide a plurality of clusters;

calculating for at least one pairs of clusters, at least two properties selected from the group consisting of (i) a number of vectors in said pair of clusters; (ii) a variability among numbers of vectors in said pair of clusters; (iii) a latency difference separating said pair of clusters; (iv) amplitude of a signal associated with said pair of clusters; and (v) frequency of a signal associated with said pair of clusters;

constructing a brain network activity (BNA) pattern for said subject, said BNA pattern having a plurality of nodes representing said plurality of clusters; and for each pair of nodes in said BNA pattern, calculating a connectivity weight to said pair of nodes and assigning said connectivity weight to said pair of nodes, thereby providing a weighted BNA pattern, wherein said calculation of said connectivity weight comprises calculating a weight index based on said at least one cluster property;

calculating a BNA pattern similarity between said BNA pattern of said subject and a reference BNA pattern previously annotated as corresponding to the brain related disorder or condition, based on the values of the connectivity weights of the BNA patterns, and diagnosing said subject with the brain related disorder or condition responsively to said calculated BNA pattern similarity; and treating the subject for the brain related disorder or condition by at least one of: a surgical intervention, a rehabilitative treatment, phototherapy, hyperbaric therapy neural feedback, EMG biofeedback, EEG neurofeedback, transcranial magnetic stimulation, and direct electrode stimulation, so as to enhance a similarity calculated between said BNA pattern of said subject and a reference BNA pattern annotated as normal, based on the values of the connectivity weights of the BNA patterns.

2. The method according to claim 1, wherein for each cluster, each vector of data characteristics corresponds to data obtained from a different subject.

3. The method according to claim 1, wherein for each cluster, all vectors of data characteristics correspond to data obtained from the same subject but in response to a separate stimulus.

4. A method of determining a brain related disorder or condition, the method comprising:

operating a measuring device placed on a scalp of a subject for collecting neurophysiological data from a brain of the subject; and operating a data processor for:

determining features and relations among features in the data by identifying patterns of peaks in the data;

comparing said features and said relations among features to features and relations among features of reference neurophysiological data so as to identify activity-related features in the data of the subject, and expressing each activity-related feature as a vector of data characteristics;

clustering said vectors to provide a plurality of clusters;

calculating for at least one pairs of clusters, at least one cluster property selected from the group consisting of (i) a number of vectors in said pair of clusters; (ii) a variability among numbers of vectors in said pair of clusters; (iii) a latency difference separating said pair of clusters; (iv) amplitude of a signal associated with said pair of clusters; and (v) frequency of a signal associated with said pair of clusters;

constructing a brain network activity (BNA) pattern having a plurality of nodes representing said plurality of clusters; and for each pair of nodes in said BNA pattern, calculating a connectivity weight to said pair of nodes and assigning said connectivity weight to said pair of nodes, thereby providing a weighted BNA pattern, wherein said calculation of said connectivity weight comprises calculating a weight index based on said at least two cluster properties;

calculating a BNA pattern similarity between said BNA pattern and a reference BNA pattern previously annotated as corresponding to the brain related disorder or condition, based on the values of the connectivity weights of the BNA patterns;

diagnosing said subject with the brain related disorder or condition responsively to said calculated BNA pattern similarity; and treating the subject for the brain related disorder or condition by at least one of: pharmacological treatment, surgical intervention, a rehabilitative treatment, phototherapy, hyperbaric therapy, neural feedback, EMG biofeedback, EEG neurofeedback, transcranial magnetic stimulation, and direct electrode stimulation, so as to enhance similarity between said BNA pattern of said subject and a reference BNA pattern annotated as normal.

5. The method according to claim 4, wherein said reference neurophysiological data corresponds to data acquired from a group or a sub-group of subjects.

6. The method according to claim 4, wherein said reference neurophysiological data corresponds to history data previously acquired from the same subject.

7. The method according to claim 4, wherein said features and relations among features of said reference data are provided as at least one previously annotated BNA pattern.

8. The method according to claim 7, wherein said at least one previously annotated BNA pattern is at least one entry in a database of previously annotated BNA patterns, and the method further comprises constructing a BNA pattern in relation to each entry of said database.

9. The method according to claim 4, further comprising extracting prognostic information regarding a brain condition, responsively to a comparison between said BNA pattern of the subject and said reference BNA pattern.

10. The method according to claim 7, wherein said at least one previously annotated BNA pattern comprises at least one BNA pattern annotated as normal, and at least one BNA pattern annotated as abnormal.

11. The method according to claim 9, further comprising:
- acquiring said neurophysiological data from the brain of the subject, before, during and/or after the subject is performing or conceptualizing performing a task, and
- presenting to the subject a feedback regarding similarity between said BNA pattern of said subject and said previously annotated BNA pattern.

12. The method according to claim 10, further comprising acquiring said neurophysiological data from the brain of the subject, before, during and/or after the subject is performing or conceptualizing performing a task, and the method further comprises stimulating said brain so as to enhance similarity between said BNA pattern of said subject and said BNA pattern annotated as normal.

13. The method according to claim 7, wherein said at least one previously annotated BNA pattern comprises a set of annotated BNA pattern.

14. The method according to claim 7, wherein said at least one previously annotated BNA pattern is a baseline annotated BNA pattern characterizing a group of subjects identified as having the same brain disorder.

15. The method according to claim 7, wherein said at least one previously annotated BNA pattern is a baseline annotated BNA pattern characterizing a group of subjects identified as having normal brain function.

16. The method according to claim 7, wherein said at least one previously annotated BNA pattern comprises at least one BNA pattern annotated as corresponding to a treated brain related disorder, and at least one baseline BNA pattern annotated as corresponding to an untreated brain related disorder.

17. The method according to claim 7, wherein said at least one previously annotated BNA pattern is a baseline annotated BNA pattern being larger than said constructed BNA pattern in terms of at least one of: (i) an order, and (ii) a size of said BNA pattern.

18. The method according to claim 4, further comprising calculating BNA pattern similarity based on said connectivity weights.

19. The method according to claim 18, further comprising determining a brain-disorder index responsively to said BNA pattern similarity, wherein said brain-disorder corresponds to said annotation.

20. The method according to claim 19, wherein said brain-disorder is ADHD.

21. The method according to claim 4, further comprising comparing said BNA pattern to at least one previously constructed BNA pattern of the same individual, and using said comparison for determining presence, absence and/or level of neural plasticity.

22. The method according to claim 4, wherein said connectivity weight comprises a statistical score characterizing a relation between said pair and corresponding features in said reference data, said relation pertaining to at least one of latency, latency difference, amplitude and frequency.

23. The method according to claim 4, further comprising constructing several BNA patterns corresponding to different time intervals, and displaying said BNA patterns on a time axis.

24. A method of assessing a likelihood of presence of attention deficit hyperactivity disorder (ADHD), comprising:
- operating a measuring device placed on a scalp of a subject for collecting neurophysiological data from a brain of the subject; and
- operating a data processor for:
- determining activity-related features in the neurophysiological data by identifying patterns of peaks in the data, and expressing each activity-related feature as a vector of data characteristics;
- clustering said vectors to provide a plurality of clusters;
- calculating for at least one pairs of clusters, at least one cluster property selected from the group consisting of (i) a number of vectors in said pair of clusters; (ii) a variability among numbers of vectors in said pair of clusters; (iii) a latency difference separating said pair of clusters; (iv) amplitude of a signal associated with said pair of clusters; and (v) frequency of a signal associated with said pair of clusters;
- constructing a brain network activity (BNA) pattern having a plurality of nodes representing said plurality of clusters;
- for each pair of nodes in said BNA pattern, calculating a connectivity weight to said pair of nodes and assigning said connectivity weight to said pair of nodes, thereby providing a weighted BNA pattern, wherein said calculation of said connectivity weight comprises calculating a weight index based on at least one cluster property; and
- calculating a BNA pattern similarity describing a comparison between said constructed weighted BNA pattern and a baseline BNA pattern, based on the values of the connectivity weights of the BNA patterns, said baseline BNA pattern having nodes representing event related potentials, predominantly at theta and alpha frequency bands, at a plurality of frontocentral and/or parietal locations within a characteristic time window of from about 100 ms to about 200 ms;
- diagnosing said subject with ADHD when said BNA pattern similarity is above a predetermined threshold; and
- treating the subject for ADHD by at least one treatment selected from the group consisting of a surgical intervention, a rehabilitative treatment, phototherapy, hyperbaric therapy neural feedback, EMG biofeedback, EEG neurofeedback, transcranial magnetic stimulation, and direct electrode stimulation so as to enhance said BNA pattern similarity.

25. The method according to claim 4, wherein said neurophysiological data comprises data acquired before, during and/or after said treatment.

26. The method according to claim 25, further comprising assessing the effect of said treatment by comparing a BNA pattern corresponding to data acquired before a treatment to a BNA pattern corresponding to data acquired during and/or after a treatment.

27. The method according to claim 25, wherein said treatment comprises a pharmacological treatment employing an active agent and a placebo treatment employing a placebo agent, and wherein the method comprises assessing the effect of said pharmacological treatment by comparing a BNA pattern corresponding to data acquired during and/or after said a placebo treatment to a BNA pattern corresponding to data acquired during and/or after said pharmacological treatment.

28. The method according to claim 27, wherein said active agent is selected from the group consisting of scopolamine, ketamine, methylphenidate, a neuroleptic agent, donepezil, physostigmine, tacrine, fluoxetine, carbamazepine, amantadine, apomorphine, bromocriptine, levodopa, pergolide, ropinirole, selegiline, trihexyphenidyl, atropine, scopolamine, glycopyrrolate, baclofen, diazepam, tizanidine and dantrolene.

29. The method according to claim 25, wherein said treatment comprises at least one treatment selected from the group consisting of a surgical intervention, a rehabilitative treatment, phototherapy, hyperbaric therapy neural feedback, EMG biofeedback, EEG neurofeedback, transcranial magnetic stimulation (TMS) and direct electrode stimulation.

30. The method according to claim 4, further comprising acquiring said neurophysiological data from the brain of the subject, before, during and/or after the subject is performing or conceptualizing performing a task, and the method further comprises stimulating said brain so as to change said BNA pattern of said subject.

31. The method according to claim 1, wherein said calculating said weight index comprises using at least two cluster properties selected from said group.

32. The method according to claim 4, wherein said calculating said weight index comprises using at least two cluster properties selected from said group.

* * * * *